United States Patent
Price et al.

(10) Patent No.: US 9,727,052 B2
(45) Date of Patent: Aug. 8, 2017

(54) IN-SITU SPECTROSCOPY FOR MONITORING FABRICATION OF INTEGRATED COMPUTATIONAL ELEMENTS

(71) Applicant: Halliburton Energy Services, Inc., Houston, TX (US)

(72) Inventors: James M Price, The Woodlands, TX (US); Aditya B. Nayak, Humble, TX (US); David L. Perkins, The Woodlands, TX (US)

(73) Assignee: Halliburton Energy Services, Inc., Houston, TX (US)

(*) Notice: Subject to any disclaimer, the term of this patent is extended or adjusted under 35 U.S.C. 154(b) by 466 days.

(21) Appl. No.: 14/414,653

(22) PCT Filed: Feb. 14, 2014

(86) PCT No.: PCT/US2014/016603
§ 371 (c)(1),
(2) Date: Jan. 13, 2015

(87) PCT Pub. No.: WO2015/122923
PCT Pub. Date: Aug. 20, 2015

(65) Prior Publication Data
US 2016/0224016 A1    Aug. 4, 2016

(51) Int. Cl.
*G01J 3/00*    (2006.01)
*G05B 19/4099*    (2006.01)
(Continued)

(52) U.S. Cl.
CPC ...... *G05B 19/4099* (2013.01); *B29D 11/0073* (2013.01); *B32B 3/266* (2013.01);
(Continued)

(58) Field of Classification Search
CPC ...... G05B 19/4099; G05B 2219/49023; B29D 11/0073; B32B 3/266; B32B 2307/40;
(Continued)

(56) References Cited

U.S. PATENT DOCUMENTS

| | | |
|---|---|---|
| 5,075,550 A | 12/1991 | Miller et al. |
| 5,399,229 A | 3/1995 | Stefani et al. |

(Continued)

FOREIGN PATENT DOCUMENTS

| | | |
|---|---|---|
| WO | WO 2004/015364 | 2/2004 |
| WO | WO 2006/031733 | 3/2006 |

(Continued)

OTHER PUBLICATIONS

Extended European Search Report, European Application No. EP13884957.5, dated Jun. 17, 2015, 7 pages.

(Continued)

*Primary Examiner* — Hina F Ayub
(74) *Attorney, Agent, or Firm* — Benjamin Fite; Parker Justiss, P.C.

(57) ABSTRACT

Technologies are described for monitoring characteristics of layers of integrated computational elements (ICEs) during fabrication using an in-situ spectrometer operated in step-scan mode in combination with lock-in or time-gated detection. As part of the step-scan mode, a wavelength selecting element of the spectrometer is discretely scanned to provide spectrally different instances of probe-light, such that each of the spectrally different instances of the probe-light is provided for a finite time interval. Additionally, an instance of the probe-light interacted during the finite time interval with the ICE layers includes a modulation that is being detected by the lock-in or time-gated detection over the finite time interval.

49 Claims, 22 Drawing Sheets

(51) Int. Cl.
  *G01J 3/28* (2006.01)
  *G01N 21/31* (2006.01)
  *B29D 11/00* (2006.01)
  *G01N 21/84* (2006.01)
  *G02B 5/28* (2006.01)
  *B32B 3/26* (2006.01)

(52) U.S. Cl.
  CPC ............. *G01J 3/28* (2013.01); *G01N 21/31* (2013.01); *G01N 21/8422* (2013.01); *G02B 5/285* (2013.01); *G02B 5/287* (2013.01); *B32B 2307/40* (2013.01); *B32B 2307/418* (2013.01); *B32B 2307/732* (2013.01); *B32B 2551/00* (2013.01); *G01N 2021/8438* (2013.01); *G05B 2219/49023* (2013.01)

(58) Field of Classification Search
  CPC ........ B32B 2307/418; B32B 2307/732; B32B 2551/00; G01J 3/28; G02B 5/285; G02B 5/287; G01N 2021/8438; G01N 21/31; G01N 21/8422
  USPC ........................................................ 356/300
  See application file for complete search history.

(56) References Cited

U.S. PATENT DOCUMENTS

| | | |
|---|---|---|
| 5,453,716 A | 9/1995 | Person et al. |
| 5,537,479 A | 7/1996 | Kreisel et al. |
| 5,619,366 A | 4/1997 | Rhoads et al. |
| 6,078,389 A | 6/2000 | Zetter |
| 6,154,550 A | 11/2000 | Beyer |
| 6,163,259 A | 12/2000 | Barsumian et al. |
| 6,198,531 B1 | 3/2001 | Myrick et al. |
| 6,213,250 B1 | 4/2001 | Wisniewski et al. |
| 6,217,720 B1 | 4/2001 | Sullivan et al. |
| 6,529,276 B1 | 3/2003 | Myrick |
| 6,646,753 B2 | 11/2003 | Zhang et al. |
| 6,777,684 B1 | 8/2004 | Volkov et al. |
| 6,804,060 B1 | 10/2004 | Tsai et al. |
| 6,905,578 B1 | 6/2005 | Moslehi et al. |
| 6,965,431 B2 | 11/2005 | Vo-Dinh et al. |
| 7,138,156 B1 | 11/2006 | Myrick et al. |
| 7,163,901 B2 | 1/2007 | Downey |
| 7,332,044 B2 | 2/2008 | Sidorin et al. |
| 7,679,563 B2 | 3/2010 | Werner et al. |
| 7,697,141 B2 | 4/2010 | Jones et al. |
| 7,753,847 B2 | 7/2010 | Greenleaf et al. |
| 7,777,870 B2 | 8/2010 | Hayes et al. |
| 7,792,644 B2 | 9/2010 | Kotter et al. |
| 7,828,929 B2 | 11/2010 | Lee et al. |
| 7,911,605 B2 | 3/2011 | Myrick et al. |
| 7,920,258 B2 | 4/2011 | Myrick et al. |
| 8,054,212 B1 | 11/2011 | Holly et al. |
| 8,106,850 B1 | 1/2012 | Gregoire et al. |
| 8,164,061 B2 | 4/2012 | Pawlak et al. |
| 8,216,161 B2 | 7/2012 | Darlington et al. |
| 8,252,112 B2 | 8/2012 | Ovshinsky |
| 2002/0090650 A1 | 7/2002 | Empedocles et al. |
| 2005/0054928 A1 | 3/2005 | Cerofolini |
| 2008/0212168 A1 | 9/2008 | Olmstead et al. |
| 2009/0182693 A1 | 7/2009 | Fulton et al. |
| 2009/0213381 A1 | 8/2009 | Appel et al. |
| 2010/0004773 A1 | 1/2010 | Kochergin |
| 2010/0089906 A1 | 4/2010 | Plantamura |
| 2010/0149537 A1* | 6/2010 | Myrick ............... G01J 3/02 356/436 |
| 2010/0153048 A1 | 6/2010 | Myrick et al. |
| 2010/0245096 A1 | 9/2010 | Jones et al. |
| 2010/0245819 A1 | 9/2010 | Li |
| 2012/0150451 A1 | 6/2012 | Skinner et al. |
| 2012/0268744 A1 | 10/2012 | Wolf et al. |
| 2013/0032338 A1 | 2/2013 | Kalia et al. |
| 2013/0035262 A1 | 2/2013 | Freese et al. |
| 2013/0083320 A1 | 4/2013 | Gao |
| 2013/0284894 A1 | 10/2013 | Freese et al. |
| 2013/0284895 A1 | 10/2013 | Freese et al. |
| 2013/0284896 A1 | 10/2013 | Freese et al. |
| 2013/0284897 A1 | 10/2013 | Freese et al. |
| 2013/0284898 A1 | 10/2013 | Freese et al. |
| 2013/0284899 A1 | 10/2013 | Freese et al. |
| 2013/0284900 A1 | 10/2013 | Freese et al. |
| 2013/0284901 A1 | 10/2013 | Freese et al. |
| 2013/0284904 A1 | 10/2013 | Freese et al. |
| 2013/0286398 A1 | 10/2013 | Freese et al. |
| 2013/0286399 A1 | 10/2013 | Freese et al. |
| 2013/0287061 A1 | 10/2013 | Freese et al. |
| 2013/0323484 A1 | 12/2013 | Pelletier et al. |

FOREIGN PATENT DOCUMENTS

| | | |
|---|---|---|
| WO | WO 2007/015115 | 2/2007 |
| WO | WO 2011/103066 | 8/2011 |
| WO | WO 2013/022556 | 2/2013 |

OTHER PUBLICATIONS

Soyemi et al. "Design and Testing of a Multivariate Optical Element: The First Demonstration of Multivariate Optical Computing for Predictive Spectroscopy", Analytical Chemistry, American Chemical Society, XP001063566, Mar. 15, 2001, pp. 1069-1079.
Sullivan et al., "Manufacture of Complex Optical Multilayer Filters using an Automated Deposition System", XP002951089, vol. 51, No. 4, Published in 1998, pp. 647-654.
Haibach et al., "On-Line Reoptimization of Filter Designs for Multivariate Optical Elements", Applied Optics, Optical Society of America, XP001152469, vol. 42, No. 10, Apr. 1, 2003, pp. 1833-1838.
International Search Report and Written Opinion of the International Searching Authority issued in International Application No. PCT/US2014/016603 dated Nov. 13, 2014; 9 pages.
Authorized Officer Han, Joong Sub in International Search Report and Written Opinion in International Application No. PCT/US2013/077686, dated Sep. 24, 2014, 14 pages.
Authorized Officer Kim, Seong Woo in International Search Report and Written Opinion in International Application No. PCT/US2013/077687, dated Sep. 23, 2014, 11 pages.
Authorized Officer Kim, Seong Woo in International Search Report and Written Opinion in International Application No. PCT/US2013/077690, dated Sep. 22, 2014, 10 pages.
Authorized Officer Lee, Dong Yun in International Search Report and Written Opinion in International Application No. PCT/US2013/077688, dated Sep. 25, 2014, 11 pages.
Bossard et al., "The Design and fabrication of planar multiband metallodielectric frequency selective surfaces for infrared applications", IEEE Trans. on Antennas and Propagation, v. 50, No. 4, Apr. 2006, 12 pages.
Eastwood et al., "Field applications of stand-off sensing using visible/NIR multivariate optical computing," Department of Chemistry and Biochemistry, University of South Carolina, SPE vol. 4199, 2001, 10 pages.
Frey et al., "Temperature-dependent refractive index of silicon and germanium," NASA Goodard Space Flight Center, Greenbelt, MD, 2006, 10 pages.
Grader et al., "Fourier transform infrared spectroscopy of a single aerosol particle," J. Chem. Phys. 86 (11), Jun. 1, 1987, 7 pages.
Haibach et al., "Precision in multivariate optical computing," Applied Optics, vol. 43, No. 10, Apr. 1, 2004, 11 pages.
J.A. Woollam Co., Inc., Characterizing Processes with EASE® In Situ Applications, Application Note, 2009, 3 pages.
Li, "Refractive Index of Silicon and Germanium and Its Wavelength and Temperature Derivatives," Center for Information and Numerical Data Analysis and Synthesis, Purdue University, J. Phys. Chem. Ref. Data, vol. 9, No. 3, 1980, 98 pages.
Morton et al., "Optical Monitoring of Thin-films Using Spectroscopic Ellipsometry," Society of Vacuum Coaters, 45th Annual Technical Conference Proceedings, 2002, 7 pages.

(56) References Cited

OTHER PUBLICATIONS

Myrick et al., "A single-element all-optical approach to chemometric prediction," Vibrational Spectroscopy 28, 2002, 9 pages.
Myrick et al., "Application of multivariate optical computing to simple near-infrared point measurements," SPIE vol. 4574, Department of Chemistry and biochemistry, University of South Carolina, 2002, 8 pages.
Myrick et al., "Spectral tolerance determination for multivariate optical element design," Fresenius J Anal Chem, 369, 2001, 5 pages.
Myrick, "Multivariate optical elements simplify spectroscopy," Laser Focus World, Mar. 1, 2002, access date Feb. 28, 2013, 3 pages http://www.laserfocusworld.com/articles/print/volume-38/issue-3/features/spectroscopy/multivariate-optical-elements-simplify-spectroscopy.html.
Paul et al., "Fabrication of mid-infrared frequency-selective surfaces by soft lithography", Applied Optics, v. 40, No. 25, Sep. 2001, 5 pages.
Priore et al., "Novel Imaging Systems: Multivariate Optical Computing in the UV-VIS," Department of Chemistry and Biochemistry, University of South Carolina, 2003, 5 pages.
Rabady et al., "High-resolution photometric optical monitoring for thin-film deposition," Applied Optics, Optical Society of America, vol. 43, No. 1, Jan. 1, 2004, 6 pages.
Soyemi et al., "Novel Filter Design Algorithm for Multivariate Optical Computing," Advanced Environmental and Chemical Sensing Technology, SPIE vol. 4205, 2001, 12 pages.
Telemark, "Model 820 In-Situ Spectroscopic Optical Monitor," Dec. 2010, 4 pages.
Woollam et al., "Overview of Variable Angle Spectroscopic Ellipsometer (VASE), Part 1: Basic Theory and Typical Applications," Society of Photo-Optical Instrumentation Engineers, Critical Reviews of Optical Science Technology CR72, 1999, 28 pages.
Zoeller et al., "Substantial progress in optical monitoring by intermittent measurement technique," SPIE, Published in the processing of the OSD, Jena 2005, vol. 5963-13, 9 pages.

* cited by examiner

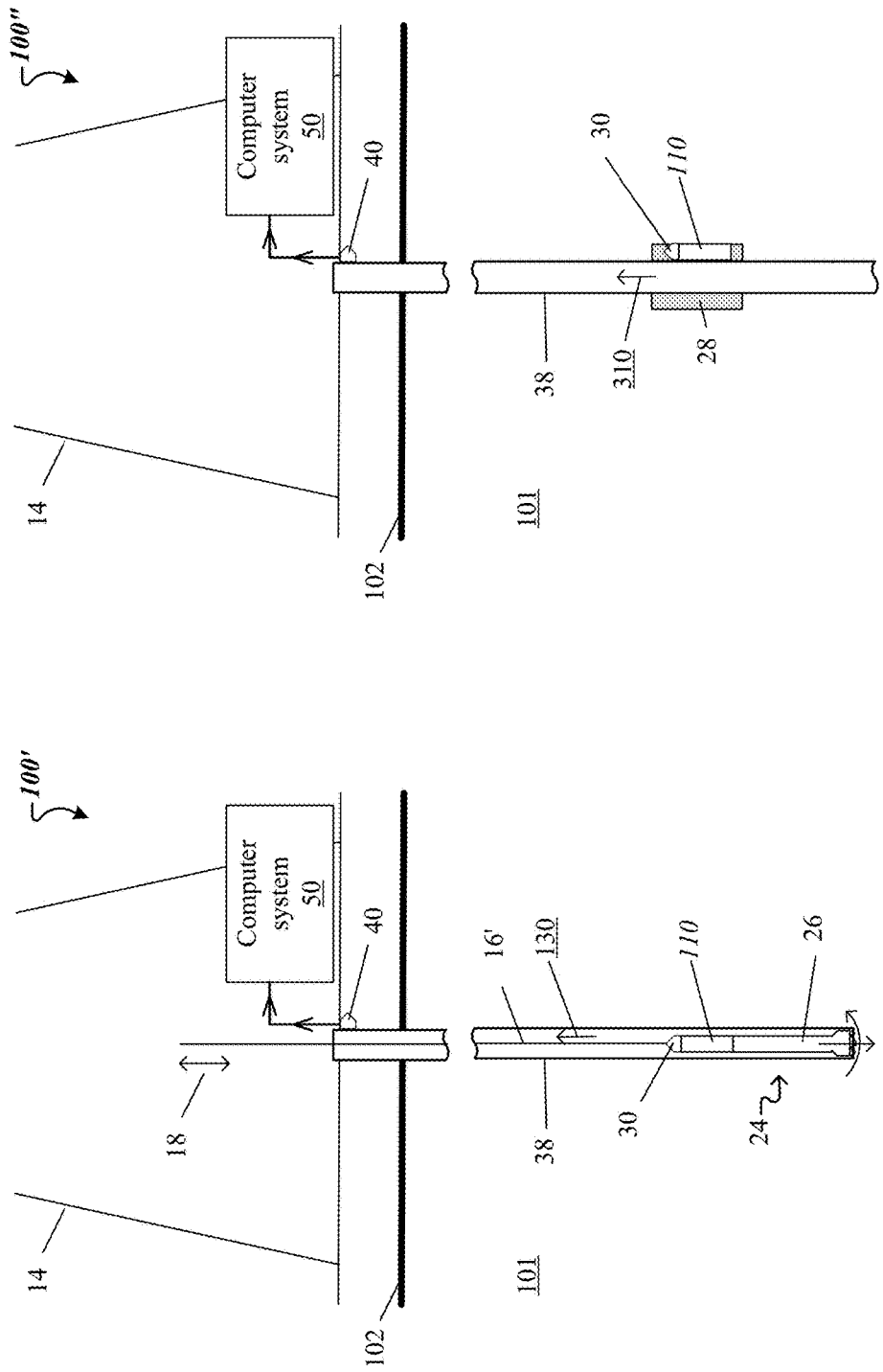

IN-SITU SPECTROSCOPY FOR MONITORING FABRICATION OF INTEGRATED COMPUTATIONAL ELEMENTS

CLAIM OF PRIORITY

This application is a U.S. National Stage of International Application No. PCT/US2014/016603, filed Feb. 14, 2014.

BACKGROUND

The subject matter of this disclosure is generally related to fabrication of an integrated computational element (ICE) used in optical analysis tools for analyzing a substance of interest, for example, crude petroleum, gas, water, or other wellbore fluids. For instance, the disclosed ICE fabrication uses in-situ spectroscopy performed in step-scan mode in combination with lock-in or time-gated detection for monitoring the ICE fabrication.

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

Integrated computational elements (ICEs) enable the measurement of various chemical or physical characteristics through the use of regression techniques. An ICE selectively weights, when operated as part of optical analysis tools, light modified by a sample in at least a portion of a wavelength range such that the weightings are related to one or more characteristics of the sample. An ICE can be an optical substrate with multiple stacked dielectric layers (e.g., from about 2 to about 50 layers), each having a different complex refractive index from its adjacent layers. The specific number of layers, N, the optical properties (e.g. real and imaginary components of complex indices of refraction) of the layers, the optical properties of the substrate, and the physical thickness of each of the layers that compose the ICE are selected so that the light processed by the ICE is related to one or more characteristics of the sample. Because ICEs extract information from the light modified by a sample passively, they can be incorporated in low cost and rugged optical analysis tools. Hence, ICE-based downhole optical analysis tools can provide a relatively low cost, rugged and accurate system for monitoring quality of wellbore fluids, for instance.

Errors in fabrication of some constituent layers of an ICE design can degrade the ICE's target performance. In most cases, deviations of <0.1%, and even 0.01% or 0.0001%, from point by point design values of the optical characteristics (e.g., complex refractive indices), and/or physical characteristics (e.g., thicknesses) of the formed layers of the ICE can reduce the ICE's performance, in some cases to such an extent, that the ICE becomes operationally useless. Complex refractive indices and thicknesses of layers of the ICEs being fabricated are determined by performing in-situ measurements during the ICE fabrication. The determined complex refractive indices and layer thicknesses of the formed layers of the ICEs within the fabrication batch are used to adjust forming of remaining layers of the ICEs based on comparisons between determined values of complex refractive indices and layer thicknesses of the fabricated ICEs' layers and their respective target values. Those familiar or currently practicing in the art will readily appreciate that the ultra-high accuracies required by ICE designs challenge the state of the art in thin film measurement techniques. In-situ measurements used for monitoring the ICE fabrication includes spectroscopy for acquiring spectra of formed ICE layers. Conventionally, the spectra are acquired by continuously scanning a wavelength selecting element of a spectrometer to provide spectrally different instances of probe-light. Spectra, acquired using this conventional acquisition mode, typically are affected from noise contributed by various noise sources present in the ICE fabrication environment.

DESCRIPTION OF DRAWINGS

FIGS. 1A-1C show multiple configurations of an example of a system for analyzing wellbore fluids that uses a well logging tool including an ICE.

Like reference symbols in the various drawings indicate like elements.

DETAILED DESCRIPTION

Figure 1A:
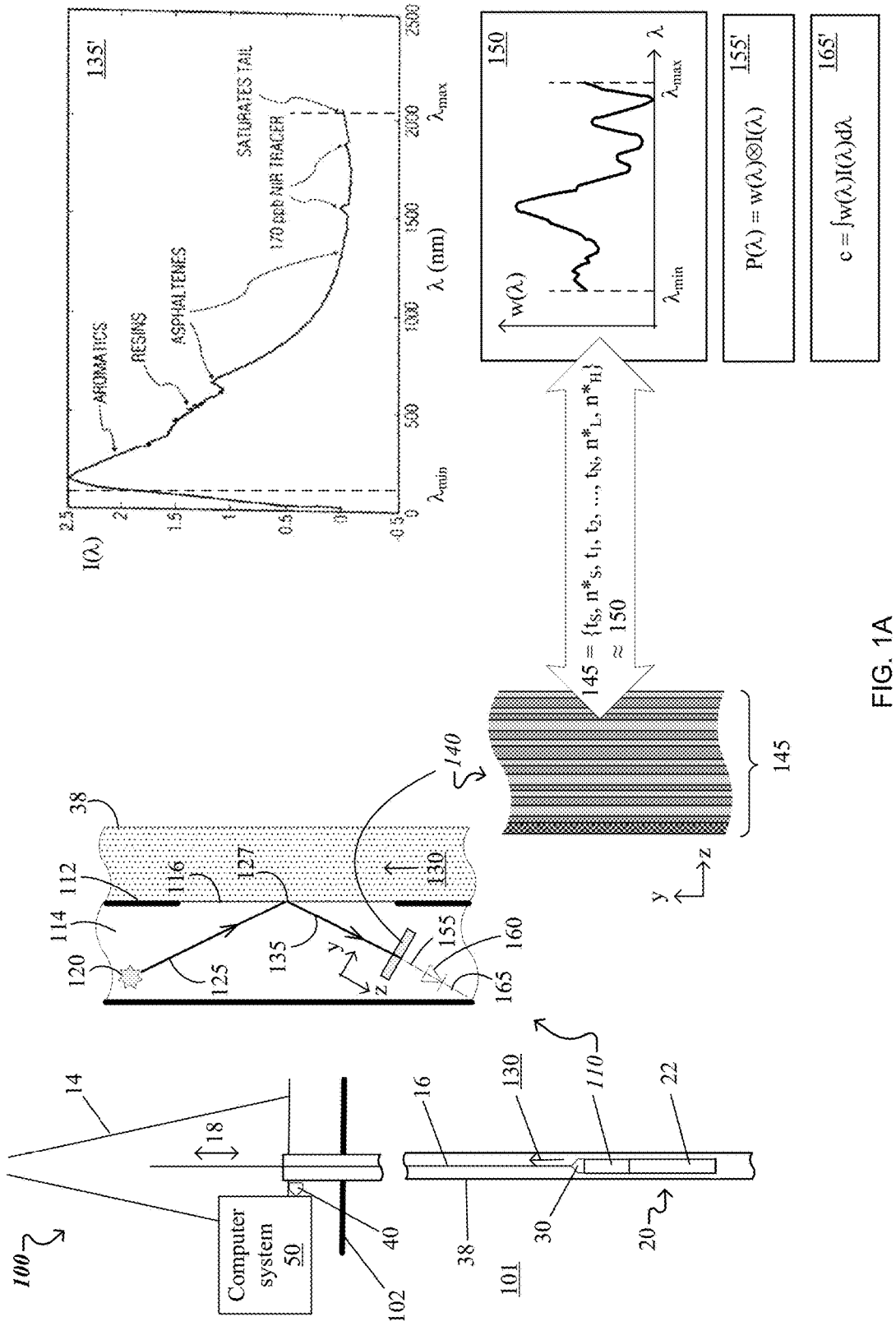

Technologies are described for monitoring characteristics of ICEs during fabrication using an in-situ spectrometer operated in step-scan mode in combination with lock-in or time-gated detection. As part of the step-scan mode, a wavelength selecting element of the spectrometer is discretely scanned to provide spectrally different instances of probe-light, such that each of the spectrally different instances of the probe-light is provided for a finite time interval. Additionally, an instance of the probe-light interacted during the finite time interval with the ICE layers includes a modulation that is being detected by the lock-in or time-gated detection over the finite time interval. Note that probe-light represents any type of electromagnetic radiation having probe wavelengths from an appropriate region of the electromagnetic spectrum.

In some implementations in which the lock-in detection is used, a timing of the modulation references the lock-in detection. Here, the instance of the probe-light that illuminates the ICE layers is modulated, and also the illuminated ICE layers are at rest relative to the modulated instance of the probe-light beam. For example, the instance of the probe-light is modulated with an optical chopper, e.g., a chopper wheel, a shutter, etc., placed upstream relative to the ICE layers. As another example, a source emits pulse-modulated probe-light, which is then used to prepare the instance of the probe-light. In this case, the prepared instance of the probe-light inherits the modulation of the emitted pulse-modulated probe-light. In other implementations in which the time-gated detection is used, the timing of the modulation is used to gate the time-gated detection. Here, the modulation is provided to an un-modulated instance of the probe-light by alternately transmitting the latter through the ICE layers and through an aperture of a support that supports the ICE layers. This is accomplished by periodically moving the ICE layers in-and-out of the instance of the probe-light beam while moving the aperture out-and-in of the instance of the probe-light beam.

Modulations, detected with lock-in or time-gated detection in the spectrally different instances of the probe-light that interacted with the ICE layers, are used to generate a spectrum of the ICE layers. Because a frequency of the modulation detected in the spectrally different instances of the probe-light that interacted with the ICE layers is chosen to be different from frequencies or harmonics of noise sources present in the ICE fabrication environment (e.g., IR lamps disposed within a deposition chamber and used for heating the ICE layers to a target fabrication temperature, a target annealing temperature, etc.), the spectra generated based on results of the disclosed monitoring techniques are unaffected by the noted noise sources. This is in contrast with conventional spectroscopy for monitoring ICE fabrication—that is carried out in continuous scanning mode, without using lock-in or time-gated detection—which typically produces spectra that are affected by noise contributed by various noise sources present in the ICE fabrication environment.

The spectra generated based on results of the disclosed monitoring techniques can be used to determine optical properties (e.g., complex refractive indices) and physical properties (e.g., thicknesses) of the ICE layers. The determined complex refractive indices and layer thicknesses of the formed layers of the ICEs within a fabrication batch are used to adjust forming of remaining layers of the ICEs based on comparisons between determined values and their respective target values.

Prior to describing example implementations of the disclosed technologies for ICE fabrication, the following technologies are described below: in Section (1)—optical analysis tools based on ICE along with examples of their use in oil/gas exploration, and in Section (2)—techniques for designing an ICE.

(1) ICE-Based Analysis of Wellbore Fluids

FIGS. 1A-1C show multiple configurations 100, 100', 100" of an example of a system for analyzing wellbore fluids 130, such that analyses are generated from measurements taken with a well logging tool 110 configured as an ICE-based optical analysis tool. The disclosed system also is referred to as a well logging system.

Each of the configurations 100, 100', 100" of the well logging system illustrated in FIGS. 1A-1C includes a rig 14 above the ground surface 102 and a wellbore 38 below the ground surface. The wellbore 38 extends from the ground surface into the earth 101 and generally passes through multiple geologic formations. In general, the wellbore 38 can contain wellbore fluids 130. The wellbore fluids 130 can be crude petroleum, mud, water or other substances and combinations thereof. Moreover, the wellbore fluids 130 may be at rest, or may flow toward the ground surface 102, for instance. Additionally, surface applications of the well logging tool 110 may include water monitoring and gas and crude transportation and processing.

FIG. 1A shows a configuration 100 of the well logging system which includes a tool string 20 attached to a cable 16 that can be lowered or raised in the wellbore 38 by draw works 18. The tool string 20 includes measurement and/or logging tools to generate and log information about the wellbore fluids 130 in the wellbore 38. In the configuration 100 of the well logging system, this information can be generated as a function of a distance (e.g., a depth) with respect to the ground surface 102. In the example illustrated in FIG. 1A, the tool string 20 includes the well logging tool 110, one or more additional well logging tool(s) 22, and a telemetry transmitter 30. Each of the well logging tools 110 and 22 measures one or more characteristics of the wellbore fluids 130. In some implementations, the well logging tool 110 determines values of the one or more characteristics in real time and reports those values instantaneously as they occur in the flowing stream of wellbore fluids 130, sequentially to or simultaneously with other measurement/logging tools 22 of the tool string 20.

FIG. 1B shows another configuration 100' of the well logging system which includes a drilling tool 24 attached to a drill string 16'. The drilling tool 24 includes a drill bit 26, the ICE-based well logging tool 110 configured as a measurement while drilling (MWD) and/or logging while drilling (LWD) tool, and the telemetry transmitter 30. Drilling mud is provided through the drill string 16' to be injected into the borehole 38 through ports of the drill bit 26. The injected drilling mud flows up the borehole 38 to be returned above the ground level 102, where the returned drilling mud can be resupplied to the drill string 16' (not shown in FIG. 1B). In this case, the MWD/LWD-configured well logging tool 110 generates and logs information about the wellbore fluids 130 (e.g., drilling mud in this case) adjacent the working drill bit 26.

FIG. 1C shows yet another configuration 100" of the well logging system which includes a permanent installation adjacent to the borehole 38. In some implementations, the permanent installation is a set of casing collars that reinforce the borehole 38. In this case, a casing collar 28 from among the set of casing collars supports the well logging tool 110 and the telemetry transmitter 30. In this manner, the well logging tool 110 determines and logs characteristics of the wellbore fluids 130 adjacent the underground location of the casing collar 28.

In each of the above configurations 100, 100' and 100" of the well logging system, the values of the one or more characteristics measured by the well logging tool 110 are provided (e.g., as a detector signal 165) to the telemetry transmitter 30. The latter communicates the measured values to a telemetry receiver 40 located above the ground surface 102. The telemetry transmitter 30 and the telemetry receiver 40 can communicate through a wired or wireless telemetry channel. In some implementations of the system configurations 100, 100' illustrated in FIGS. 1A and 1B, e.g., in slickline or coiled tubing applications, measurement data generated by the well logging tool 110 can be written locally to memory of the well logging tool 110.

The measured values of the one or more characteristics of the wellbore fluids 130 received by the telemetry receiver 40 can be logged and analyzed by a computer system 50 associated with the rig 14. In this manner, the measurement values provided by the well logging tool 110 can be used to generate physical and chemical information about the wellbore fluids 130 in the wellbore 38.

Referring again to FIG. 1A, the well logging tool 110 includes a light source 120, an ICE 140 and an optical transducer 160. The well logging tool 110 has a frame 112 such that these components are arranged in an enclosure 114 thereof. A cross-section of the well logging tool 110 in a plane perpendicular to the page can vary, depending on the space available. For example, the well logging tool's cross-section can be circular or rectangular, for instance. The well logging tool 110 directs light to the sample 130 through an optical interface 116, e.g., a window in the frame 112. The well logging tool 110 is configured to probe the sample 130 (e.g., the wellbore fluids stationary or flowing) in the wellbore 38 through the optical interface 116 and to determine an amount (e.g., a value) of a given characteristic (also referred to as a characteristic to be measured) of the probed sample 130. The characteristic to be measured can be any one of multiple characteristics of the sample 130 including concentration of a given substance in the sample, a gas-oil-ratio (GOR), pH value, density, viscosity, etc.

The light source 120 outputs light with a source spectrum over a particular wavelength range, from a minimum wavelength $\lambda_{min}$ to a maximum wavelength $\lambda_{max}$. In some implementations, the source spectrum can have non-zero intensity over the entire or most of the wavelength range $\lambda_{max}$-$\lambda_{min}$. In some implementations, the source spectrum extends through UV-vis (0.2-0.8 μm) and near-IR (0.8-2.5 μm) spectral ranges. Alternatively, or additionally, the source spectrum extends through near-IR and mid-IR (2.5-25 μm) spectral ranges. In some implementations, the source spectrum extends through near-IR, mid-IR and far-IR (25-100 μm) spectral ranges. In some implementations, the light source 120 is tunable and is configured in combination with time resolved signal detection and processing.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The light modified by the sample has a modified spectrum $I(\lambda)$ 135' over the particular wavelength range. In the reflective configuration of the well logging tool 110 illustrated in FIG. 1A (i.e., where the light to be analyzed reflects at the sample/window interface), the modified spectrum $I(\lambda)$ 135' is a reflection spectrum associated with the sample 130. In a transmission configuration of the well logging tool 110 (not shown in FIG. 1A), the probe beam is transmitted through the sample as modified light, such that the modified spectrum $I(\lambda)$ 135' is a transmission spectrum associated with the sample.

In general, the modified spectrum $I(\lambda)$ 135' encodes information about multiple characteristics associated with the sample 130, and more specifically the encoded information relates to current values of the multiple characteristics. In the example illustrated in FIG. 1A, the modified spectrum 135' contains information about one or more characteristics of the wellbore fluids 130.

With continued reference to FIG. 1A, and the Cartesian coordinate system provided therein for reference, the ICE 140 is arranged to receive a beam 135 of the sample modified light, and is configured to process it and to output a beam 155 of processed light. The beam 135 of sample modified light is incident on a first surface of the ICE 140 along the z-axis, and the beam 155 of processed light is output along the z-axis after transmission through the ICE 140. Alternatively or additionally, the beam 155 (or an additional reflected beam) of processed light can be output after reflection off the first surface of the ICE 140. The ICE 140 is configured to process the sample modified light by weighting it in accordance with an optical spectrum $w(\lambda)$ 150 associated with a characteristic to be measured.

The optical spectrum $w(\lambda)$ 150 is determined offline by applying conventional processes to a set of calibration spectra $I(\lambda)$ of the sample which correspond to respective known values of the characteristic to be measured. As illustrated by optical spectrum $w(\lambda)$ 150, optical spectrums generally may include multiple local maxima (peaks) and minima (valleys) between $\lambda_{min}$ and $\lambda_{max}$. The peaks and valleys may have the same or different amplitudes. For instance, an optical spectrum $w(\lambda)$ can be determined through regression analysis of $N_c$ calibration spectra $I_j(\lambda)$ of a sample, where j=1, . . . , $N_c$, such that each of the calibration spectra $I_j(\lambda)$ corresponds to an associated known value of a given characteristic for the sample. A typical number $N_c$ of calibration spectra $I_j(\lambda)$ used to determine the optical spectrum $w(\lambda)$ 150 through such regression analysis can be $N_c$=10, 40 or 100, for instance. The regression analysis outputs, within the $N_c$ calibration spectra $I_j(\lambda)$, a spectral pattern that is unique to the given characteristic. The spectral pattern output by the regression analysis corresponds to the optical spectrum $w(\lambda)$ 150. In this manner, when a value of the given characteristic for the sample is unknown, a modified spectrum $I_u(\lambda)$ of the sample is acquired by interacting the probe beam 125 with the sample 130, then the modified spectrum $I_u(L)$ is weighted with the ICE 140 to determine a magnitude of the spectral pattern corresponding to the optical spectrum $w(\lambda)$ 150 within the modified spectrum $I_u(\lambda)$. The determined magnitude is proportional to the unknown value of the given characteristic for the sample.

For example, the sample can be a mixture (e.g., the wellbore fluid 130) containing substances X, Y and Z, and the characteristic to be measured for the mixture is concentration $c_X$ of substance X in the mixture. In this case, $N_c$ calibration spectra $I_j(\lambda)$ were acquired for $N_c$ samples of the mixture having respectively known concentration values for each of the substances contained in the $N_c$ samples. By applying regression analysis to the $N_c$ calibration spectra $I_j(\lambda)$, a first spectral pattern that is unique to the concentration $c_X$ of the X substance can be detected (recognized), such that the first spectral pattern corresponds to a first optical spectrum $w_{cX}(\lambda)$ associated with a first ICE, for example. Similarly, second and third spectral patterns that are respectively unique to concentrations $c_Y$ and $c_Z$ of the Y and Z substances can also be detected, such that the second and third spectral patterns respectively correspond to second and third optical spectra $w_{cY}(\lambda)$ and $w_{cZ}(\lambda)$ respectively associated with second and third ICEs. In this manner, when a new sample of the mixture (e.g., the wellbore fluid 130) has an unknown concentration $c_X$ of the X substance, for instance, a modified spectrum $I_u(\lambda)$ of the new sample can be acquired by interacting the probe beam with the mixture, then the modified spectrum $Iu(\lambda)$ is weighted with the first ICE to determine a magnitude of the first spectral pattern within the modified spectrum $I_u(\lambda)$. The determined magnitude is proportional to the unknown value of the concentration $c_X$ of the X substance for the new sample.

Referring again to FIG. 1A, the ICE 140 includes N layers of materials stacked on a substrate, such that complex refractive indices of adjacent layers are different from each other. The total number of stacked layers can be between 6 and 50, for instance. The substrate material can be BK7, diamond, Ge, ZnSe (or other transparent dielectric material), and can have a thickness in the range of 0.02-2 mm, for instance, to insure structural integrity of the ICE 140.

Throughout this specification, a complex index of refraction (or complex refractive index) n* of a material has a complex value, $Re(n^*)+iIm(n^*)$. $Re(n^*)$ represents a real component of the complex index of refraction responsible for refractive properties of the material, and $Im(n^*)$ represents an imaginary component of the complex index of refraction (also known as extinction coefficient κ) responsible for absorptive properties of the material. In this specification, when it is said that a material has a high complex index of refraction $n^*_H$ and another material has a low complex index of refraction $n^*_L$, the real component $Re(n^*_H)$ of the high complex index of refraction $n^*_H$ is larger than the real component $Re(n^*_L)$ of the low complex index of refraction $n^*_L$, $Re(n^*_H) > Re(n^*_L)$. Materials of adjacent layers of the ICE are selected to have a high complex index of refraction $n^*_H$ (e.g., Si), and a low complex index of refraction $n^*_L$ (e.g., $SiO_2$). Here, $Re(n^*_{Si}) \approx 2.4 > Re(n^*_{SiO2}) \approx 1.5$. For other material pairings, however, the difference between the high complex refractive index $n^*_H$ and low complex refractive index $n^*_L$ may be much smaller, e.g., $Re(n^*_H) \approx 1.6 > Re(n^*_L) \approx 1.5$. The use of two materials for fabricating the N layers is chosen for illustrative purposes only. For example, a plurality of materials having different complex indices of refraction, respectively, can be used. Here, the materials used to construct the ICE are chosen to achieve a desired optical spectrum $w(\lambda)$ 150.

A set of design parameters 145—which includes the total number of stacked layers N, the complex refractive indices $n^*_H$, $n^*_L$ of adjacent stacked layers, and the thicknesses of the N stacked layers $t(1), t(2), \ldots, t(N-1), t(N)$—of the ICE 140 can be chosen (as described below in connection with FIG. 2) to be spectrally equivalent to the optical spectrum $w(\lambda)$ 150 associated with the characteristic to be measured. As such, an ICE design includes a set 145 of thicknesses $\{t(i), i=1, \ldots, N\}$ of the N layers stacked on the substrate that correspond to the optical spectrum $w(\lambda)$ 150.

In view of the above, the beam 155 of processed light output by the ICE 140 has a processed spectrum $P(\lambda) = w(\lambda) \otimes I(\lambda)$ 155' over the wavelength range $\lambda_{max}-\lambda_{min}$, such that the processed spectrum 155' represents the modified spectrum $I(\lambda)$ 135' weighted by the optical spectrum $w(\lambda)$ 150 associated with the characteristic to be measured.

The beam 155 of processed light is directed from the ICE 140 to the optical transducer 160, which detects the processed light and outputs an optical transducer signal 165. A value (e.g., a voltage) of the optical transducer signal 165 is a result of an integration of the processed spectrum 155' over the particular wavelength range and is proportional to the unknown value "c" 165' of the characteristic to be measured for the sample 130.

In some implementations, the well logging tool 110 can include a second ICE (not shown in FIG. 1A) associated with a second ICE design that includes a second set of thicknesses $\{t'(i), i=1, \ldots, N'\}$ of a second total number N' of layers, each having a different complex refractive index from its adjacent layers, the complex refractive indices and the thicknesses of the N' layers corresponding to a second optical spectrum $w'(\lambda)$. Here, the second optical spectrum $w'(\lambda)$ is associated with a second characteristic of the sample 130, and a second processed spectrum represents the modified spectrum $I(\lambda)$ 135' weighted by the second optical spectrum $w'(\lambda)$, such that a second value of a second detector signal is proportional to a value of the second characteristic for the sample 130.

In some implementations, the determined value 165' of the characteristic to be measured can be logged along with a measurement time, geo-location, and other metadata, for instance. In some implementations, the detector signal 165, which is proportional to a characteristic to be measured by the well logging tool 110, can be used as a feedback signal to adjust the characteristic of the sample, to modify the sample or environmental conditions associated with the sample, as desired.

Characteristics of the wellbore fluids 130 that can be related to the modified spectrum 135' through the optical spectra associated with the ICE 140 and other ICEs (not shown in FIG. 1A) are concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

(2) Aspects of ICE Design

Aspects of a process for designing an ICE associated with a characteristic to be measured (e.g., one of the characteristics enumerated above) are described below. Here, an input of the ICE design process is a theoretical optical spectrum $w_{th}(\lambda)$ associated with the characteristic. An output of the ICE design process is an ICE design that includes specification of (1) a substrate and a number N of layers to be formed on the substrate, each layer having a different complex refractive index from its adjacent layers; and (2) complex refractive indices and thicknesses of the substrate and layers that correspond to a target optical spectrum $w_t(\lambda)$. The target optical spectrum $w_t(\lambda)$ is different from the theoretical optical spectrum $w_{th}(\lambda)$ associated with the characteristic, such that the difference between the target and theoretical optical spectra cause degradation of a target performance relative to a theoretical performance of the ICE within a target error tolerance. The target performance represents a finite accuracy with which an ICE having the target optical spectrum $w_t(\lambda)$ is expected to predict known values of the characteristic corresponding to a set of validation spectra of a sample with a finite (non-zero) error. Here, the predicted values of the characteristic are obtained through integration of the validation spectra of the sample respectively weighted by the ICE with the target optical spectrum $w_t(\lambda)$. The theoretical performance represents the maximum accuracy with which the ICE—if it had the theoretical optical spectrum $w_{th}(\lambda)$—would predict the known values of the characteristic corresponding to the set of validation spectra of the sample. Here, the theoretically predicted values of the characteristic would be obtained through integration of the validation spectra of the sample respectively weighted by the ICE, should the ICE have the theoretical optical spectrum $w_{th}(\lambda)$.

Figure 2:
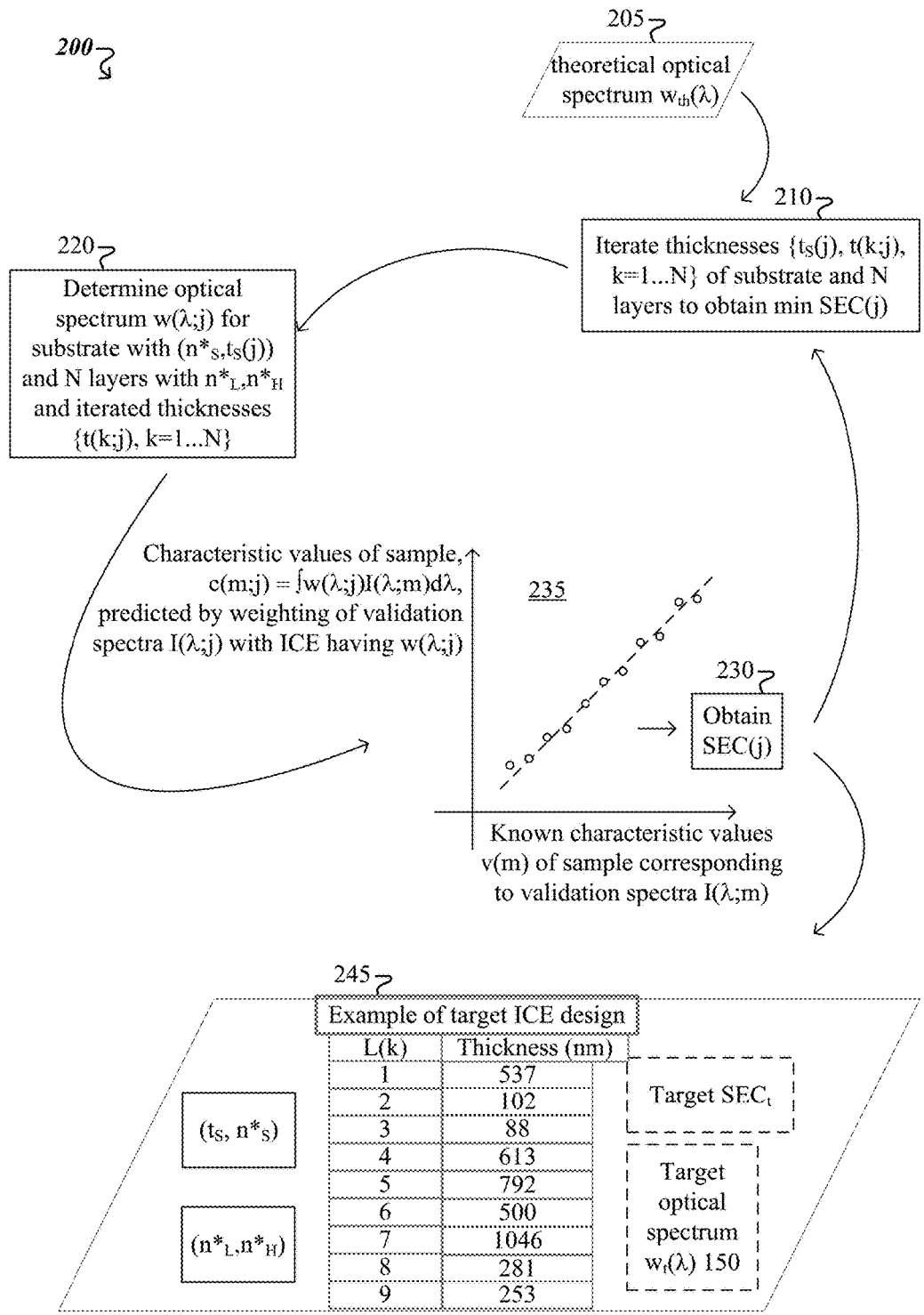
FIG. 2 is a flowchart showing an example of a process for designing an ICE.

FIG. 2 is a flow chart of an example of a process 200 for generating an ICE design. One of the inputs to the process 200 is a theoretical optical spectrum $w_{th}(\lambda)$ 205. For instance, to design an ICE for measuring concentration of a substance X in a mixture, a theoretical optical spectrum $w_{th}(\lambda)$, associated with the concentration of the substance X in the mixture, is accessed, e.g., in a data repository. As described above in this specification, the accessed theoretical optical spectrum $w_t(\lambda)$ corresponds to a spectral pattern detected offline, using a number $N_c$ of calibration spectra of the mixture, each of the $N_c$ calibration spectra corresponding to a known concentration of the substance X in the mixture. An additional input to the process 200 is a specification of materials for a substrate and ICE layers. Materials having different complex refractive indices, respectively, are specified such that adjacent ICE layers are formed from materials with different complex refractive indices. For example, a first material (e.g., Si) having a high complex refractive index $n^*_H$ and a second material (e.g., $SiO_x$) having a low complex refractive index $n^*_L$ are specified to alternately form the ICE layers. As another example, a layer can be made from high index material (e.g., Si), followed by a layer made from low index material (e.g., $SiO_x$), followed by a layer made from a different high index material (e.g., Ge), followed by a layer made from a different low index material ($MgF_2$), etc. The iterative design process 200 is performed in the following manner.

At 210 during the $j^{th}$ iteration of the design process 200, thicknesses $\{t_S(j), t(1;j), t(2;j), \ldots, t(N-1;j), t(N;j)\}$ of the substrate and a number N of layers of the ICE are iterated.

At 220, a $j^{th}$ optical spectrum $w(\lambda;j)$ of the ICE is determined corresponding to complex refractive indices and previously iterated thicknesses $\{t_S(j), t(1;j), t(2;j), \ldots, t(N-1;j), t(N;j)\}$ of the substrate and the N layers, each having a different complex refractive index from its adjacent layers. The iterated thicknesses of the substrate and the N layers are used to determine the corresponding $j^{th}$ optical spectrum $w(\lambda;j)$ of the ICE in accordance with conventional techniques for determining spectra of thin film interference filters.

At 230, performance of the ICE, which has the $j^{th}$ optical spectrum $w(\lambda;j)$ determined at 220, is obtained. To do so, a set of validation spectra of a sample is accessed, e.g., in a data repository. Respective values of a characteristic of the sample are known for the validation spectra. For instance, each of $N_v$ validation spectra $I(\lambda;m)$ corresponds to a value v(m) of the characteristic of the sample, where m=1, ..., $N_v$. In the example illustrated in FIG. 2, $N_v$=11 validation spectra, respectively corresponding to 11 known values of the characteristic to be measured for the sample, are being used.

Graph 235 shows (in open circles) values c(m;j) of the characteristic of the sample predicted by integration of the validation spectra $I(\lambda;m)$ weighted with the ICE, which has the $j^{th}$ optical spectrum $w(\lambda;j)$, plotted against the known values v(m) of the characteristic of the sample corresponding to the validation spectra $I(\lambda;m)$. The predicted values c(m;1) of the characteristic are found by substituting, in formula 165' of FIG. 1A, (1) the spectrum $I(\lambda)$ 135' of sample modified light with the respective validation spectra $I(\lambda;m)$ and (2) the target spectrum $w_t(\lambda)$ 150 with the $j^{th}$ optical spectrum $w(\lambda;j)$. In this example, performance of the ICE, which has the $j^{th}$ optical spectrum $w(\lambda;j)$, is quantified in terms of a weighted measure of distances from each of the open circles in graph 235 to the dashed-line bisector between the x and y axes. This weighted measure is referred to as the standard calibration error (SEC) of the ICE. For instance, an ICE having the theoretical spectrum $w_{th}(\lambda)$ has a theoretical $SEC_{th}$ that represents a lower bound for the SEC(j) of the ICE having the $j^{th}$ spectrum $w(\lambda;j)$ determined at 220 during the $j^{th}$ iteration of the design process 200: $SEC(j) > SEC_{th}$.

In this specification, the SEC is chosen as a metric for evaluating ICE performance for the sake of simplicity. Note that there are other figures of merit that may be used to evaluate performance of ICE, as is known in the art. For example, sensitivity—which is defined as the slope of characteristic change as a function of signal strength—can also be used to evaluate ICE performance. As another example, standard error of prediction (SEP)—which is defined in a similar manner to the SEC except it uses a different set of validation spectra—can be used to evaluate ICE performance. Any of the figure(s) of merit known in the art is/are evaluated in the same general way by comparing theoretical performance with that actually achieved. Which figure(s) of merit or combinations are used to evaluate ICE performance is determined by the specific ICE design.

The iterative design process 200 continues by iterating, at 210, the thicknesses of the substrate and the N layers. The iterating is performed such that a $(j+1)^{th}$ optical spectrum $w(\lambda;j+1)$—determined at 220 from the newly iterated thicknesses—causes, at 230, improvement in performance of the ICE, to obtain SEC(j+1)<SEC(j). In some implementations, the iterative design process 200 is stopped when the ICE's performance reaches a local maximum, or equivalently, the SEC of the ICE reaches a local minimum. For example, the iterative process 200 can be stopped at the $(j+1)^{th}$ iteration when the current SEC(j+1) is larger than the last SEC(j), SEC(j+1)>SEC(j). In some implementations, the iterative design process 200 is stopped when, for a given number of iterations, the ICE's performance exceeds a specified threshold performance for a given number of iterations. For example, the iterative design process 200 can be stopped at the $j^{th}$ iteration when three consecutive SEC values decrease monotonously and are less than a specified threshold value: $SEC_0 > SEC(j-2) > SEC(j-1) > SEC(j)$.

In either of these cases, an output of the iterative process 200 represents a target ICE design 245 to be used for fabricating an ICE 140, like the one described in FIG. 1A, for instance. The ICE design 245 includes specification of (1) a substrate and N layers, each having a different complex refractive index from its adjacent layers, and (2) complex refractive indices $n^*_S$, $n^*_H$, $n^*_L$ and thicknesses $\{t_S(j), t(1;j), t(2;j), t(N-1;j), t(N)\}$ of the substrate and N layers corresponding to the $j^{th}$ iteration of the process 200. Additional components of the ICE design are the optical spectrum $w(\lambda;j)$ and the SEC(j)—both determined during the $j^{th}$ iteration based on the thicknesses $\{t_S(j), t(1;j), t(2;j), t(N-1;j), t(N)\}$. As the ICE design 245 is used as input for fabrication processes described herein, the iteration index j—at which the iterative process 200 terminates—is dropped from the notations used for the components of the ICE design.

In this manner, the thicknesses of the substrate and the N layers associated with the ICE design 245 are denoted $\{t_S, t(1), t(2), t(N-1), t(N)\}$ and are referred to as the target thicknesses. The optical spectrum associated with the ICE design 245 and corresponding to the target thicknesses is referred to as the target optical spectrum $w_t(\lambda)$ 150. The SEC associated with the ICE design 245—obtained in accordance with the target optical spectrum $w_t(\lambda)$ 150 corresponding to the target thicknesses—is referred to as the target $SEC_t$. In the example illustrated in FIG. 2, the ICE design 245 has a total of N=9 alternating Si and $SiO_2$ layers, with complex refractive indices $n_{Si}$, $n_{SiO2}$, respectively. The layers' thicknesses (in nm) are shown in the table. An ICE fabricated based on the example of ICE design 245 illustrated in FIG. 2 is used to predict value(s) of concentration of substance X in wellbore fluids 130.

(3) ICE Fabrication Monitored with In-Situ Spectroscopy

As described above in connection with FIG. 2, an ICE design specifies a number of material layers, each having a different complex refractive index from its adjacent layers. An ICE fabricated in accordance with the ICE design has (i) a target optical spectrum $w_t(\lambda)$ and (ii) a target performance $SEC_t$, both of which corresponding to the complex refractive indices and target thicknesses of a substrate and a total number of layers specified by the ICE design. Performance of the ICE fabricated in accordance with the ICE design can be very sensitive to actual values of the complex refractive indices and thicknesses obtained during deposition. For a wide variety of reasons, the actual values of the complex refractive indices of materials to be deposited and/or the rate(s) of the deposition may drift within a fabrication batch or batch-to-batch, or may be affected indirectly by errors caused by measurement systems used to control the foregoing fabrication parameters. For example, materials used for deposition (Si, $SiO_2$) may be differently contaminated, or react differently due to different chamber conditions (e.g., pressure or temperature). For some layers of the ICE design 245, a small error, e.g., 0.1% or 0.001%, in the thickness of a deposited layer can result in a reduction in the performance of an ICE associated with the ICE design 245 below an acceptable threshold.

Actual values of complex refractive indices or thicknesses of deposited layers can be different from their target values due to deposition rate drifts (i) during fabrication of one or more layers of the ICEs fabricated within a batch, or (ii) from batch-to-batch. For example, deposition rate changes may be caused by contamination of materials used for deposition (Si, $SiO_2$), or by modifications of deposition chamber conditions (e.g., pressure or temperature). The deposition rate changes can lead to changes in thicknesses and/or complex refractive indices of the deposited layers compared to their respective targets, which in turn result in degradation of the fabricated ICEs' performance with respect to a target performance. The foregoing process changes can be corrected or prevented altogether by in-situ monitoring the ICE fabrication.

For instance, in-situ spectroscopy for monitoring the ICE fabrication is used to generate a spectrum of one or more of the ICEs being fabricated. The generated spectrum is used next to determine optical characteristics (e.g., complex refractive indices) or physical characteristics (e.g., thicknesses) of deposited layers of the ICEs. Differences between the determined and target complex refractive indices and thicknesses of the formed layers are used to obtain new target thicknesses for the layers that remain to be deposited. The foregoing steps of these in-situ spectroscopic measurements and optimizations are repeated after deposition of at least some of sub-layers or layers of the ICEs being fabricated.

Typically, an in-situ spectrometer used for monitoring deposition of ICE layers has a normal incidence transmission configuration. In this configuration, a source providing probe-light is typically placed outside of a deposition chamber. For example, the probe-light can be provided to the deposition chamber through a sapphire input window having about 85% transmission. The probe-light is directed through the deposition chamber onto a witness sample (e.g., one or more of the ICEs being fabricated). For example, about 5% of the probe-light incident on a typical ICE is transmitted through it. The probe-light transmitted through the witness sample is directed to exit the bottom of the deposition chamber. For example, the probe-light transmitted through the witness sample can exit the deposition chamber through a sapphire exit window having about 85% transmission. Once outside the deposition chamber, the probe-light transmitted through the witness sample can be steered to a detector by a mirror assembly. For example, a reflective surface of the mirror assembly can be gold-coated with a reflectance of about 95%.

Noise contributions that may affect a detector signal and, thus, the accuracy of the spectrum—generated by the spectrometer based on the detector signal—include a length of and a number/arrangement of optical components within the optical path of the probe-light/transmitted probe-light described above.

Other noise contributions that may affect a detector signal and, thus, the accuracy of the spectrum—generated by the spectrometer based on the detector signal—include extraneous IR light sources (or light sources different from the spectrometer's light source) such as, e.g., in-situ halogen lamp(s), ion-source(s), E-beam gun, etc. For example, the deposition chamber may have multiple halogen lamps for heating the ICES' substrates while depositing the layers of the ICES up to 300° C., such that the fabricated ICES can be annealed in-situ. If the ICES were removed from the deposition chamber without having been annealed, their optical response would change due to moisture absorption and/or temperature variation. By annealing the ICES in the deposition chamber during fabrication, the fabricated ICES will have reduced or no variability of their optical response during operation.

There are several factors that can contribute to the reduction of signal-to-noise ratio (S/N) of spectroscopy of the ICES performed during fabrication. Such factors have been addressed in conventional ICE fabrication systems to mitigate their contributions to overall measurement noise, in the following manner. For example, a decrease in path length from source to detector causes a reduction in S/N. The current optical path length of a conventional ICE fabrication system has been reduced, as much as possible, to approximately 5' (or 152 cm.) As another example, reflection and transmission properties of individual optical elements along the path of the probe-light beam—including sapphire windows and gold mirrors—were chosen such that losses are minimized within spectroscopic windows of interest (e.g., near-IR and IR) for ICE applications. As yet another example, while heating the ICE substrates up to 300° C., the lamps disposed inside the deposition chamber emit IR radiation. This radiative source is one of the most influential factors for noise contribution. To mitigate this, collimated tubes can be coupled to the bottom of the deposition chamber adjacent the exit window(s) to shield the extraneous IR light emitted by the lamps.

Moreover, increasing either the number of overall ICE layers and/or their thicknesses will decrease the transmissivity of the ICEs, and therefore S/N of conventional in-situ spectroscopy. For an ICE design with a large number of layers and thicknesses, optical monitoring in the UV-visible spectral range is less useful than an IR spectroscopic measurement. Improving S/N of in-situ spectroscopy in the IR spectral range by filtering out the extraneous IR light contributions to the detector signal would maximize the accuracy of the generated IR spectra. IR spectra generated in this manner may be crucial for accurately determining thicknesses and optical constants of ICEs with larger number of layers and thicknesses.

To improve the S/N of the detector signal of an in-situ spectrometer, the detector output can be temporally synchronized with a modulation of the probe-light such that all noise contributions from other IR sources collected by the spectrometer's detector are suppressed. For example, this is accomplished by placing a chopper in the beam path of the probe-light directly after its source and connecting the detector signal to a lock-in-amplifier (because phase sensitive detection associated with the lock-in amplifier can detect small signals in the presence of a significant amount of noise). In doing so, an AC component (also referred to as a modulation) of the detected signal that is in phase with a modulation provided by the chopper can now be isolated, while suppressing all other DC and out-of-phase AC contributions from the (previously described) various sources of noise present in the ICE fabrication environment.

This approach can be used for improving S/N of a spectrum acquired with a spectrometer operated in "single-shot" mode. For instance, a broadband ("white") probe-light beam is modulated prior to illuminating the witness sample; the probe-light transmitted through the witness sample is spectrally-spread (e.g., using a grating or prism) over the probe-light's wavelength range; and the spectrally-spread transmitted probe-light is detected with a photo-sensitive array, where elements of the photo-sensitive array correspond to wavelengths of the probe-light's wavelength range. Magnitudes of AC components of signals output by the elements of the photo-sensitive array are measured using lock-in detection (referenced by the modulation of the probe-light). The measured values of the AC components are proportional to respective values of transmissivity of the witness sample at the wavelengths corresponding to the elements of the photo-sensitive array.

The above approach for improving S/N of a spectrum acquired with a spectrometer operated in "single-shot" mode must be modified when the spectrum is acquired with an FTIR spectrometer (or with any other spectrometer operated in scanning mode as opposed to single-shot mode.) Optical path length difference of an interferometer of the FTIR spectrometer is scanned to generate broadband IR spectra. Conventionally, this is accomplished by continuously moving a mirror within the interferometer. Typical rapid-scan mirror velocities are v=0.2-1.2 cm/s. This is often expressed as a Fourier frequency, $f=2v\tilde{v}$, where $\tilde{v}$ is a wavenumber of the reference laser (e.g., 15800 $cm^{-1}$.) Thus, the frequency is $f \leq 40$ kHz. Since the conventional continuous scanning of the optical path length difference would interfere with the chopper frequency, the disclosed technologies use an interferometer operated in discrete-scanning mode, also referred to as step-scan mode. For example, a given optical path length difference can be set for a certain position of the mirror of the interferometer and held fixed while the chopper and lock-in-amplifier measure interferogram intensity. Once the intensity is measured for the given optical path length difference, the mirror can be moved to the next optical path length where it will be held fixed while the chopper and lock-in-amplifier measure the intensity again. This discrete scan would then continue for the full range available of the optical path length. At the end of the scan, the phase-sensitive measured intensity, as a function of optical path length difference, can be recombined and Fourier-transformed in order to obtain the IR spectrum of the probe-light transmitted through the witness sample in the frequency domain.

In some implementations, two choppers operating at different frequencies can be used in conjunction with the disclosed spectroscopies. In other implementations, a rotating planetary motion of substrate holders used to hold substrates of multiple ICES within a batch can be used to time-gate the detection. This would replace the need for a chopper inserted before the spectrometer. In some implementations, a monochromator-based interferometer is used instead of the FTIR interferometer. Here, a relative orientation between a wavelength selecting element (e.g., a grating or a prism) and a slit (also referred to as an output port) of the monochromator is scanned in step-scan mode, in accordance with the disclosed technologies. Although slower than conventional spectroscopy performed in continuous scan mode without lock-in or time-gated detection, the disclosed phase sensitive or time-gated spectroscopies performed in step-scan mode can filter out noise contributions from the ICE fabrication environment. Hence, the disclosed spectroscopies have larger S/N and, thus, are more accurate than conventional spectroscopy.

In accordance with the disclosed technologies, in-situ spectroscopy of a witness sample is performed in step-scan mode while the witness sample is at rest relative to the probe-light beam and a modulation is induced in the probe-light illuminating the witness sample, in some implementations. Here, a timing of the modulation is used for referencing lock-in detection. In other implementations, the in-situ spectroscopy of the witness sample is performed in step-scan mode while the witness sample undergoes a periodic motion relative to the probe-light beam. Here, time-gated detection is based on a timing of the periodic motion. Results of the lock-in detection or the time-gated detection are used to generate a spectrum of the probe-light that interacted with the witness sample. Moreover, the generated spectrum is used to determine in near-real time complex refractive indices and thicknesses (and/or other characteristics) of layers of the current instance of the ICEs. Throughout this specification, determining a complex refractive index n* of a layer means that both the real component Re(n*) and the imaginary component Im(n*) of the complex refractive index are being determined. The determined complex refractive indices and thicknesses of the layers of the current instance of the ICEs are used to control deposition of the current layer and layers remaining to be formed.

Particular implementations of the disclosed technologies can be configured so as to realize one or more of the following potential advantages.

Fabrication of ICEs includes processes that reduce variations in an ICE's optical spectrum over various environmental conditions like temperature. Following fabrication at relatively low temperatures, a given ICE is annealed ex-situ from the deposition chamber to allow operation at elevated temperatures. To allow for in-situ annealing, halogen lamps are used for heating an ICE's substrate while depositing the layers of the ICE. However, the halogen lamps inadvertently emit radiation in the IR portion of the ICE's optical spectrum and contribute to background noise during in-situ IR spectroscopic measurements. The disclosed technologies using FTIR or monochromator-based spectrometers operated in step-scan mode in combination with lock-in or time-gated detection allow for in-situ monitoring of ICE fabrication in an environment that includes heat sources that emit IR radiation.

Further, high volume ICE fabrication is performed in a deposition chamber big enough to accommodate a large number of substrates to manufacture ICEs in large quantities. As a result of using the large deposition chamber, the optical path length of an in-situ spectrometer is increased considerably from conventional spectrometers, and hence, the disclosed spectroscopies are beneficial to increase the S/N to collect accurate spectra during ICE fabrication. As such, the disclosed technologies using FTIR or monochromator-based spectrometers operated in step-scan mode in combination with lock-in or time-gated detection allow for in-situ monitoring of ICE fabrication in manufacturing-scale, large deposition chambers.

Furthermore, ion-assist E-beam deposition offers many advantages including consistent thin-film properties and rapid thin-film growth. However, the advantages gained by ion-assist e-beam deposition come at the price of more process variables to monitor and control. Variability of these process variables can impact the ICE transmission profile which, in turn, directly affects the ICE performance. It is highly desirable to be able to accurately monitor the as-deposited transmission profile during fabrication to aid in controlling the process variables. The accuracy of the IR spectral measurements will be greatly improved with higher S/N. As such, the disclosed technologies using FTIR or monochromator-based spectrometers operated in step-scan mode in combination with lock-in or time-gated detection allow for in-situ monitoring of ion-assist E-beam fabrication of ICEs.

In general, fabrication and analysis of ICEs necessitates the use of accurate and rapid characterization methods in order to re-optimize the filter design on-line. Conventional approaches to reduce S/N, such as co-averaging spectra generated by a scanning monochromator, or FTIR spectrometer, would not serve the purpose and functionality as well as implementing the disclosed spectroscopies that can filter out contributions of noise sources from the ICE fabrication environment without considerable increase in (data acquisition) time.

Details of one or more of the foregoing embodiments are described below.

(3.1) System for ICE Fabrication Equipped with an Interferometer-Based Spectrometer Operated in Step-Scan Mode in Combination with Lock-in Detection A target ICE design can be provided to an ICE fabrication system in which multiple ICEs are fabricated based on the target ICE design. Technologies for in-situ monitoring of ICE fabrication using spectra of current instances of ICEs being fabricated are described below, such that the spectra are generated from results of step-scan spectroscopy performed with an interferometer-based spectrometer in combination with lock-in detection.

Figure 3A:
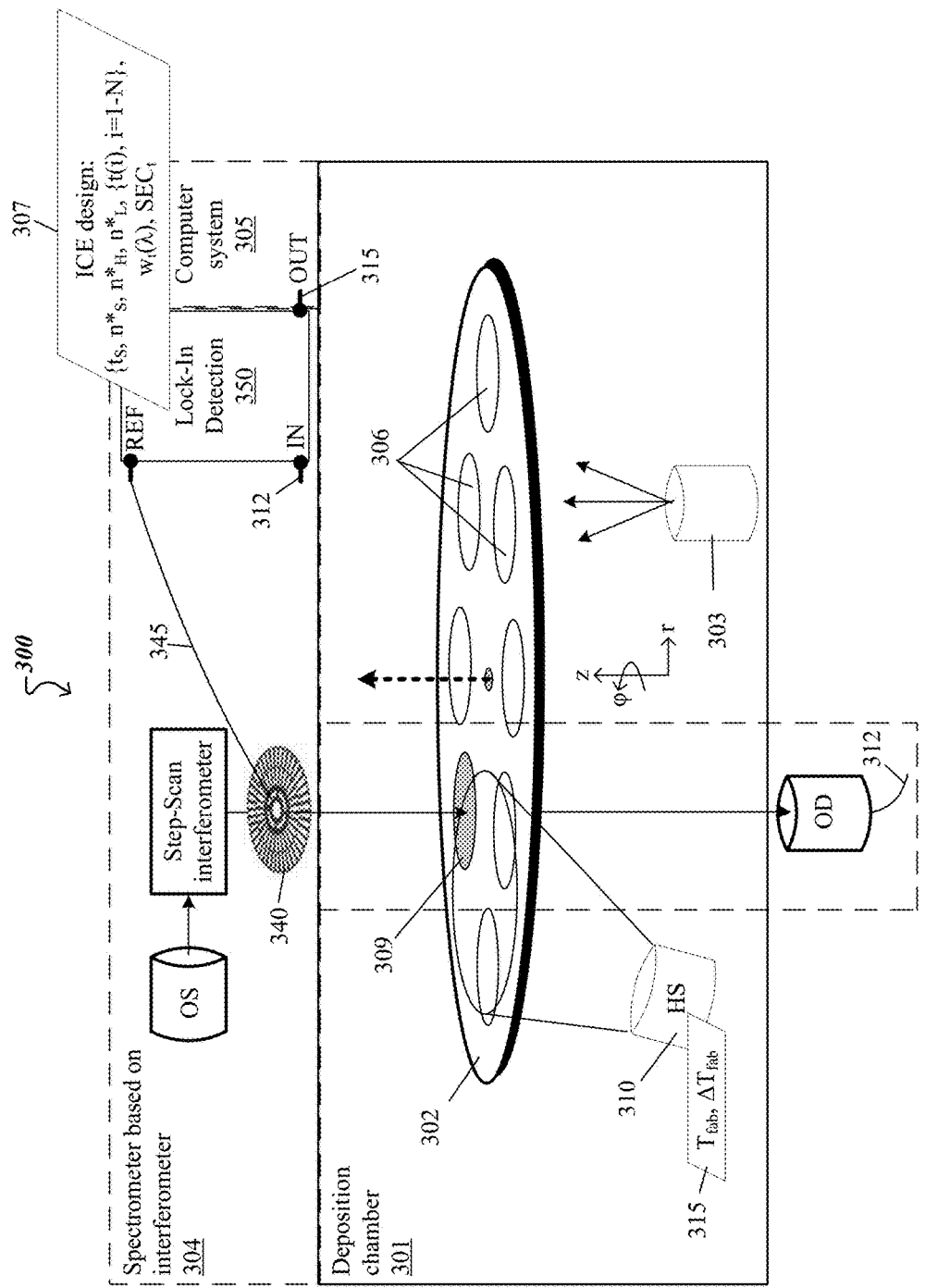
FIGS. 3A-3G show aspects of an implementation of a system for fabricating ICEs that uses an in-situ interferometer-based spectrometer operated in step-scan mode—to provide probe-light modulated with an optical chopper to illuminate witness samples—in combination with a lock-in detection module—that detects the modulation of probe-light that interacts with the witness samples—to monitor fabrication of the ICEs.

FIG. 3A shows an example of an ICE fabrication system 300. The ICE fabrication system 300 includes a deposition chamber 301 to fabricate one or more ICEs 306, a spectrometer 304 to acquire spectra of probe-light that interacts with formed layers of the ICEs while the ICEs are being fabricated, and a computer system 305 to control the fabrication of the one or more ICEs based at least in part on the acquired spectra.

The deposition chamber 301 includes one or more deposition sources 303 to provide materials with a low complex index of refraction $n^*_L$ and a high complex index of refraction $n^*_H$ used to form layers of the ICEs 306. Substrates on which layers of the ICEs 306 will be deposited are placed on a substrate support 302, such that the ICEs 306 are within the field of view of the deposition source(s) 303. The substrates have a thickness $t_S$ and a complex refraction index $n^*_S$ specified by a target ICE design 307, e.g., ICE design 145 or 245.

Various physical vapor deposition (PVD) techniques can be used to form a stack of layers of each of the ICEs 306 based on the target ICE design 307. In accordance with PVD techniques, the layers of the ICEs are formed by condensation of a vaporized form of material(s) of the source(s) 305, while maintaining vacuum in the deposition chamber 301. One such example of PVD technique is electron beam (E-beam) deposition, in which a beam of high energy electrons is electromagnetically focused onto material(s) of the deposition source(s) 303, e.g., either Si, or $SiO_2$, to evaporate atomic species. In some cases, E-beam deposition is assisted by ions, provided by ion-sources (not shown in FIG. 3A), to clean or etch the ICE substrate(s); and/or to increase the energies of the evaporated material(s), such that they are deposited onto the substrates more densely, for instance. Other examples of PVD techniques that can be used to form the stack of layers of each of the ICEs 306 are: cathodic arc deposition, in which an electric arc discharged at the material(s) of the deposition source(s) 303 blasts away some into ionized vapor to be deposited onto the ICEs 306 being formed; evaporative deposition, in which material(s) included in the deposition source(s) 303 is(are) heated to a high vapor pressure by electrically resistive heating; pulsed laser deposition, in which a laser ablates material(s) from the deposition source(s) 303 into a vapor; or sputter deposition, in which a glow plasma discharge (usually localized around the deposition source(s) 303 by a magnet—not shown in FIG. 3A) bombards the material(s) of the source(s) 303 sputtering some away as a vapor for subsequent deposition.

A relative orientation of and separation between the deposition source(s) 303 and the substrate support 302 are configured to provide desired deposition rate(s) and spatial uniformity across the ICEs 306 disposed on the substrate support 302. As a spatial distribution of a deposition plume provided by the deposition source(s) 303 is non-uniform along at least a first direction, the substrate support 302 is periodically moved with respect to the deposition source 303 along the first direction (e.g., rotated along an azimuthal direction "φ" about an axis laterally offset from the deposition source(s) 303 that passes through the center of the substrate support 302) to obtain reproducibly uniform layer deposition of the ICEs 306 within a batch. For instance, the substrate support 302 (also referred to as a platen) that has a diameter of 13" (or about 330 mm) can support 66 ICEs 306, each of which has a diameter of 1" (or about 25 mm). In some implementations, one or more substrate supports 302 are mounted on a mount. In such cases, the mount rotates relative to the deposition source(s) 303 with a first period $T_1$ around the center of the mount, and each substrate support 302 rotates relative to the mount with a second period $T_2$ around the center of the substrate support 302.

A heating source 310 provides heat to the current instances of the ICEs 306 distributed on the substrate support 302 to maintain their temperature within a target fabrication temperature range $\Delta T_{fab}$ around a target fabrication temperature $T_{fab}$. The target fabrication temperature $T_{fab}$ and range $\Delta T_{fab}$ depend on whether the ICEs 306 are fabricated to be used in an annealed state or an un-annealed state. An ICE is irreversibly annealed when heated at least through an upper bound of an annealing temperature range associated with the ICE design 307. For example, a finite (non-zero) annealing temperature range associated with the ICE design 307 is bound by an annealing temperature $T_{AL}$ of a layer material with low complex refractive index $n^*_L(T)$ and an annealing temperature $T_{AH}$ of an adjacent layer material with high complex refractive index $n^*_H(T)$. Here, a constituent material of the ICE with low/high complex refractive index $n^*_L(T)/n^*_H(T)$ irreversibly transitions from a stressed state to an annealed (stress-relieved) state when heated through the annealing temperature $T_{AL}/T_{AH}$. As another example, the foregoing annealing temperature range collapses to a single annealing temperature $T_A$ associated with the ICE design 307 if the stress is relieved—not in the bulk of the individual materials of the adjacent layers of the ICE, but—at the interface between the adjacent layers having complex refractive indices $n^*_L(T)$ and $n^*_H(T)$. Here the ICE irreversibly transitions from an interface-stressed state to an interface-annealed (stress-relieved) state when heated through the annealing temperature $T_A$.

A process parameter 315 that includes the target fabrication temperature $T_{fab}$ and the target fabrication temperature range $\Delta T_{fab}$ is accessed by the computer system 305 and used to control the temperature of current instances of ICEs 306 during fabrication of ICEs associated with the ICE design 307. In some implementations, the heating source 310 includes an IR emitter placed apart from the substrate support 302 and focused on, at least, a portion of the substrate support 302. Here, the IR emitter can be a halogen lamp or an IR laser, for instance. A radiation flux (intensity per unit area) provided by the IR emitter onto the substrate support 302 is adjusted in conjunction with a period of rotation of the substrate support 302 to maintain the current instances of ICEs 306 across the substrate support 302 at the target fabrication temperature $T_{fab}$.

Power provided to the source(s) 303, its(their) arrangement relative to the one or more substrate supports 302, etc., are used to control deposition rate(s) R of the source(s) 303. For instance, if an ICE design specifies that a $j^{th}$ layer L(j) of the N layers of an ICE is a Si layer with a target thickness t(j), a stack including the previously formed ICE layers L(1), . . . , L(j−1) is exposed to a Si source—from among the deposition sources 303—for a duration $\Delta T(j)=t(j)/R_{Si}$, where the $R_{Si}$ is a deposition rate of the Si source. In accordance with the disclosed technologies, the actual complex refractive indices and thicknesses of the deposited layers L(1), . . . , L(j−1), L(j) can be determined when the deposition of the current layer L(j) is interrupted, e.g., with 10% left of the duration T(j), or when the deposition is completed at the end of the duration T(j). The complex refractive indices and thicknesses of the formed layers are determined in near real-time from a spectrum S(λ;j) of probe-light that interacts with the formed layers L(1), . . . , L(j−1), L(j) acquired by the spectrometer 304.

The spectrometer 304 includes an optical source (OS) to emit probe-light having a wavelength range from $\lambda_{min}$ to $\lambda_{max}$, and an interferometer to receive the emitted probe-light and to provide spectrally different instances of the probe-light corresponding to different optical path differences of the interferometer. Here, the interferometer is operated in step-scan mode, such that each of the instances of the probe-light is provided for a finite (non-zero) time interval. As in this example the interferometer is operated in step-scan mode, it will also be referred to as a step-scan interferometer (SSI). Further, spectrometer 304 includes an optical chopper 340 to modulate the instances of the probe-light over the finite time interval with a modulation 345. The modulated instances of the probe-light are provided through an entry port associated with the spectrometer 304 into the deposition chamber 301 to illuminate a witness sample 309. Here, the witness sample 309 is supported on the substrate support 302 along with the ICEs 306 being fabricated in the deposition chamber 301, so the witness sample 309 experiences the same periodic motion with respect to the deposition source(s) 303 as the ICEs 306 during deposition. In the example implementation illustrated in FIG. 3A, the substrate support 302, and thus the witness sample 309, is maintained at rest while the spectrometer 304 acquires a spectrum S(λ;j). The modulated instances of the probe-light transmitted through the witness sample 309 are output from the deposition chamber 301 through an exit port associated with the spectrometer 304.

Furthermore, the spectrometer 304 includes an optical detector (OD) to collect light that exits the deposition chamber through the exit port, where the collected light includes the modulated instances of the probe-light transmitted through the witness sample 309, and light emitted by various noise sources, e.g., the heat source(s) 310, from the deposition chamber 310 or elsewhere in the environment of the ICE fabrication system 300. The detector OD converts the collected light to a detector signal 312. Additionally, the spectrometer 304 includes a lock-in detection module 350—synchronized with the modulation 345 induced by the chopper 340 in the instances of the probe-light—to process the detector signal 312. A lock-in signal 315 of the lock-in detection module 350 (also referred to as a measurement signal 315) is proportional to a spectral amplitude of the detector signal 312 at a frequency of the modulation 345. In this manner, the measurement signal 315 represents an average of amplitudes of the instances of the probe-light transmitted through the witness sample 309 over at least a portion of the finite time interval.

The computer system 305 uses a set of values of the measurement signal 315 corresponding to the different spectral instances of the probe-light to generate a spectrum $S(\lambda;j)$ of probe-light transmitted through the formed layers $L(1), \ldots, L(j-1), L(j)$ of the witness sample 309. The generated spectrum $S(\lambda;j)$, over the wavelength range from $\lambda_{min}$ to $\lambda_{max}$, can be used by the computer system 305 to determine the complex refractive indices and thicknesses of each of the formed layers in the stack: $n^*_{SiO2}$, $t'(1)$, $t'(2)$, $t'(j-1)$, $t'(j)$. The computer system 305 makes this determination by solving Fresnel's equations for propagating the interacted probe-light through the formed layers in the stack.

The formed layers of any one or more of the current instances of the ICEs 306 can be used as a witness sample by the spectrometer 304 to monitor ICE layer deposition in the deposition chamber 301. As the witness sample 309 is placed at predetermined locations on the substrate support 302 among the ICEs 306 being fabricated in the deposition chamber 301 to move with respect to the deposition source(s) 303 along a path similar to the paths of the ICEs 306, the witness sample 309 experiences similar deposition conditions in the deposition chamber 301 as the ICEs 306, so properties of the witness sample 309 (e.g., complex refractive indices and thicknesses of layers of the witness sample) are similar to the corresponding properties of the fabricated ICEs 306.

In some implementations, an area of the witness samples 309 may be larger than the area of the other ICEs 306, e.g., "P" times larger. In such cases, at the end of the ICE fabrication, the witness sample 309 may be cut into (up to) P pieces to use the resulting P ICEs—along with the other ICEs 306 from the same fabrication batch—in logging tools. For example, the ICEs 306 have a diameter of 1" (about 25 mm) while each witness sample 309 placed on a substrate support 302 has a diameter of 3" (about 76 mm). Here P=9. When deposition of the N layers of the ICE design is completed, the 3"-witness sample can be cut into 9 ICEs that have a size similar to the size of the fabricated ICEs 306. In other implementations, any one or more of the ICEs 306 (without having different sizes) can be used as the one or more witness samples 309.

Various components of the spectrometer 304 and their corresponding functions are now described in detail.

Figure 3B:
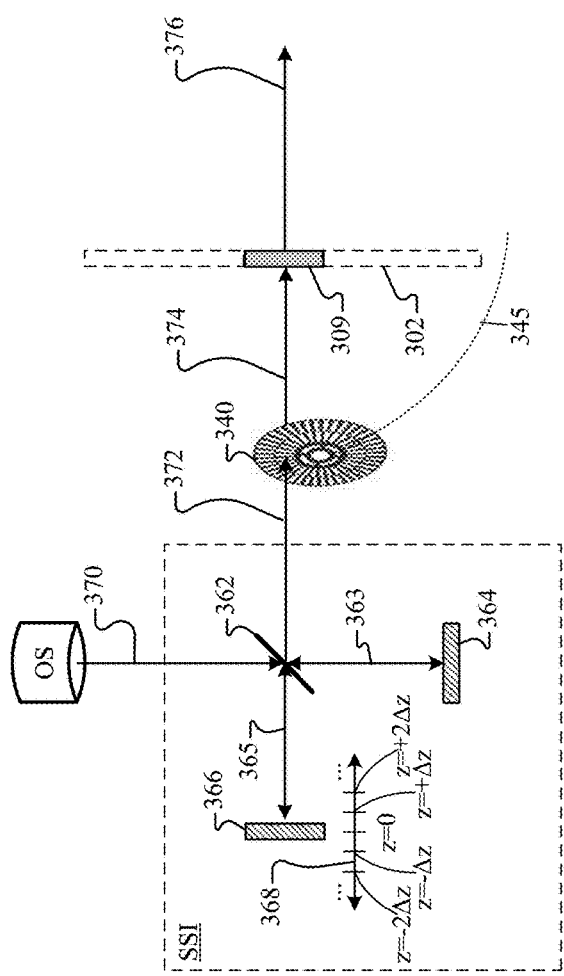

FIG. 3B shows a portion of the optical path of the spectrometer 304 upstream relative to the witness sample 309. Note that the portion illustrated in FIG. 3B represents a corresponding portion of FIG. 3A. The source OS of the spectrometer 304 outputs the probe-light 370 over the wavelength range from $\lambda_{min}$ to $\lambda_{max}$. The wavelength range $[\lambda_{min},\lambda_{max}]$ of the probe-light 370 is also referred to as measurement spectral range. The interferometer includes a beam-splitter 362 that transmits a first portion of the probe-light 370 and reflects a second portion of the probe-light 370. The interferometer further includes a first, fixed mirror 364 that reflects the first portion of the probe-light 370 back to the beam-splitter 362. An optical path 363 of the first portion of the probe-light 370, along which the first portion propagates from the beam-splitter 362 to the first mirror 364 and back to the beam-splitter 362, is referred to as a fixed arm 363 of the interferometer. Furthermore, the interferometer includes a second mirror 366 mounted on a translation stage 368. A position "z" along the translation stage 368 of the second mirror 366 can be varied in a discrete manner, e.g., in increments of $\pm\Delta z$. The second mirror 366 reflects the second portion of the probe-light 370 back to the beam-splitter 362. An optical path 365 of the second portion of the probe-light 370, along which the second portion propagates from the beam-splitter 362 to the second mirror 366 and back to the beam-splitter 362, is referred to as a variable arm 365 of the interferometer.

The first and second portions of the probe-light impinging on the beam-splitter 362 after propagation respectively along the fixed 363 and variable 365 arms of the interferometer have wavelengths spanning the measurement spectral range $[\lambda_{min},\lambda_{max}]$. Moreover, the beam-splitter 362 combines the first and second portions of the probe-light impinging on the beam-splitter 362 into combined light 372 that includes a subset of the wavelengths of the measurement spectral range $[\lambda_{min},\lambda_{max}]$. Specifically, the combined light 372 includes those wavelengths of the measurement spectral range $[\lambda_{min},\lambda_{max}]$ that interfere constructively for a current optical path difference between the fixed 363 and variable 365 arms of the interferometer, and lacks those wavelengths of the measurement spectral range $[\lambda_{min},\lambda_{max}]$ that interfere destructively for the current optical path difference. The combined light 372 represents (and is referred to as) an instance of the probe-light 370 output by the interferometer for the current optical path difference. In this manner, a plurality of spectrally-different instances 372 of the probe-light corresponding to a plurality of different optical path differences of the interferometer can be provided by discretely scanning the location of the second mirror 366 along the translation stage 368. When the optical path difference is zero (or equivalently, when the fixed 363 and variable 365 arms of the interferometer are equal), an instance 372-0 of the probe-light that has the same wavelengths as the probe-light 370 is provided by the interferometer. When the optical path difference is $+\Delta z$ (or equivalently, when the fixed 363 arm is longer than the variable arm 365 by $\Delta z$), a first instance 372-1 of the probe-light— that is spectrally different than the probe-light 370 is provided by the interferometer. When the optical path difference is $+2\Delta z$ (or equivalently, when the fixed 363 arm is longer than the variable arm 365 by $2\Delta z$), a second instance 372-2 of the probe-light—that is spectrally different than the probe-light 370 and the first instance 372-1 of the probe-light—is provided by the interferometer. And so on, other instances 372-$m$ of the probe-light—that are spectrally different from each other—are provided by the interferometer for corresponding optical path differences of $\pm m\Delta z$, where $m=0, \pm 1, \ldots, \pm m_{max}$.

Each instance 372 of the probe-light provided by the interferometer is modulated with the optical chopper 340. The optical chopper 340 can be an opto-mechanical shutter, a chopper wheel, an acusto-optic modulator or any other optical modulator. The optical chopper 340 imparts a modulation 345 to each instance 372 of the probe-light and outputs a modulated instance 374 of the probe-light. The modulation 345 can be amplitude modulation (e.g., the optical chopper can alternatively block or pass each instance 372 of the probe-light 370, or can periodically attenuate each instance 372 of the probe-light.) In other implementations, the modulation 345 can be frequency or phase modulation. A timing of the modulation 345 is used as a reference signal by the lock-in detection module 350 as described in detail below.

Figure 3C:
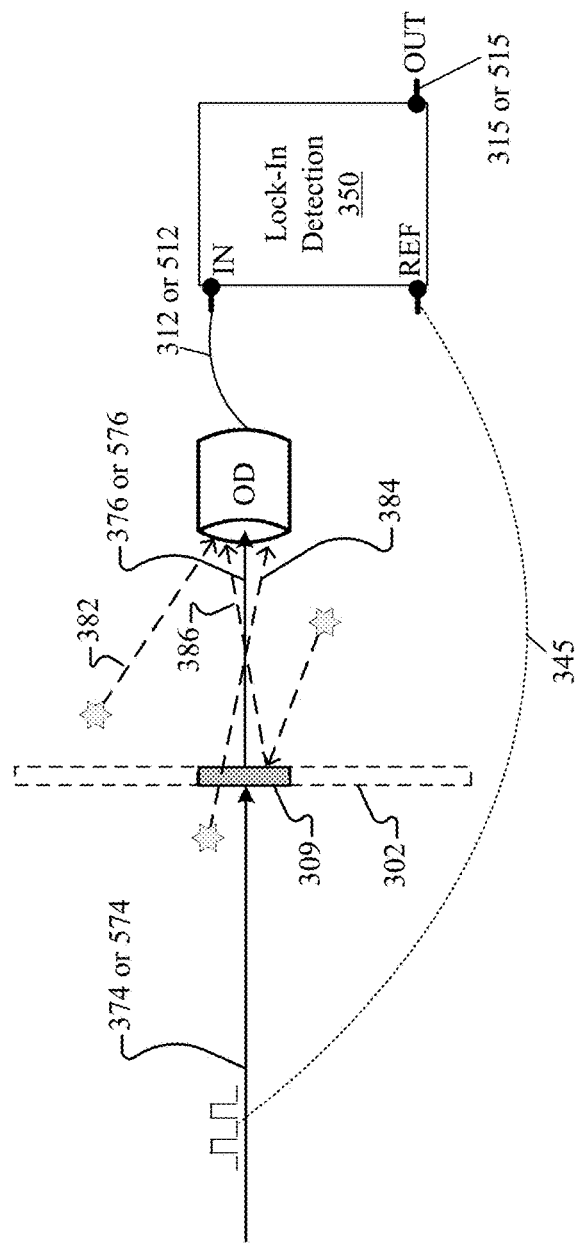

FIGS. 3B and 3C show that each modulated instance 374 of the probe-light is directed into the deposition chamber 301 through an input port associated with the spectrometer 304 (not shown in FIGS. 3B-3C) to illuminate the witness sample 309 supported by the substrate support 302, which is at rest, in this example. Each modulated instance of the probe-light transmitted through the witness sample 309, referenced as 376, is directed outside the deposition chamber

301 through an exit port associated with the spectrometer 304 (not shown in FIGS. 3B-3C) to be collected by the detector OD.

FIG. 3C shows an optical path of the spectrometer 304 downstream relative to the witness sample 309. Note that the portion illustrated in FIG. 3C represents a corresponding portion of FIG. 3A. In addition to the modulated instance of the probe-light transmitted through the witness sample 309, referenced as 376, the detector OD collects light emitted by noise sources within the deposition chamber (e.g., the heating sources 310 described above) or from elsewhere within the environment of the ICE fabrication system 300. For example, a first portion 382 of the light emitted by the noise sources is collected by the detector OD after direct propagation from the noise sources. As another example, a second portion 384 of the light emitted by the noise sources is collected by the detector OD after propagation from the noise sources by transmission through the witness sample 309. As yet another example, a third portion 386 of the light emitted by the noise sources is collected by the detector OD after propagation from the noise sources by reflection off the witness sample 309.

The light collected by the detector OD, including the modulated light 376 and the noise light 378, 384 or 386, is converted into detector signal 312. The lock-in detection module 350 is referenced by a timing of the modulation 345 and receives as input the detector signal 312. For a current optical path difference $m\Delta z$, where m is one of $0, \pm 1, \pm 2, \ldots, \pm m_{max}$, intensity variation of the detector signal 312 can include the modulation 345 of the modulated instance of the probe-light transmitted through the witness sample 309, referenced as 376, and intensity changes of the noise light 382, 384 or 386. A frequency of the modulation 345 is selected to be different from frequencies and tones at which the changes of the noise light 382, 384 and 386 can occur. The frequency of the modulation 345 can be of order 100 Hz, 1 kHz, or 10 kHz, for instance. Moreover, at the current optical path difference, the amplitude of the modulation 345 of the modulated instance of the probe-light transmitted through the witness sample 309, referenced as 376, is constant for constant emission of probe-light 370 by the source OS. As such, the lock-in signal 315 (also referred to as the measurement signal 315) is proportional to spectral amplitude of the detector signal 312 at a frequency of the reference signal 345. In this manner, the measurement signal 315 represents an average over multiple modulation periods of the intensity of the modulated instance of the probe-light transmitted through the witness sample 309, referenced as 376.

Figure 3D:
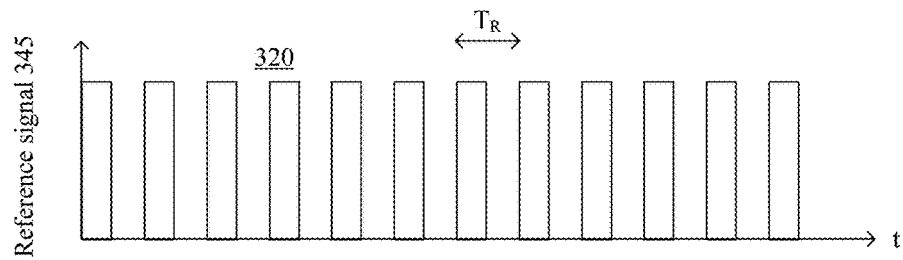
Figure 3E:
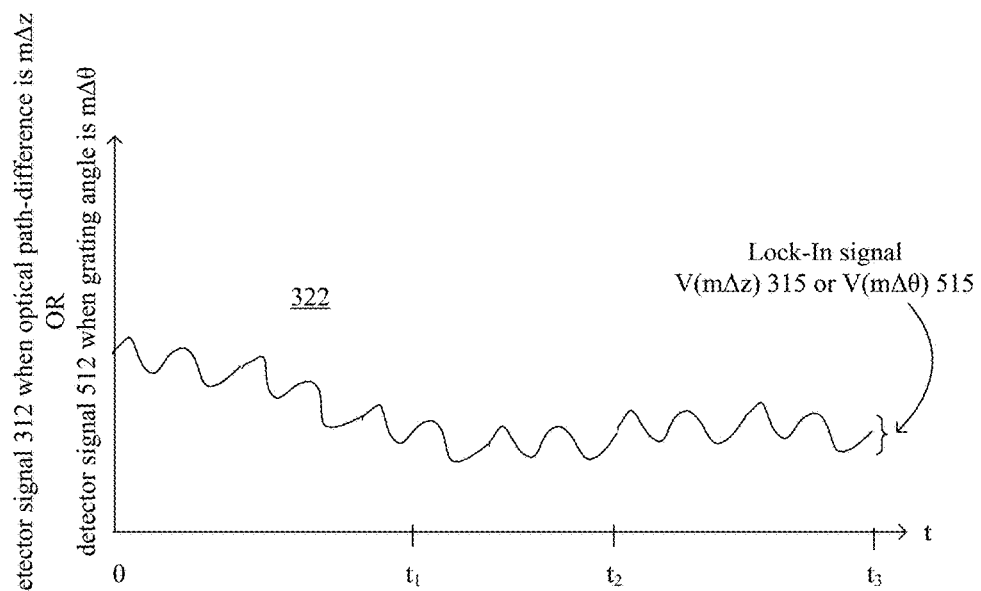

FIG. 3D shows a graph 320 that illustrates an example of a reference signal of the lock-in detection module 350 corresponding to the modulation 345 imparted by the chopper 340 to each instance 372 of the probe-light. Here, the modulation 345 is a square ON/OFF signal. The period of the modulation 345 can be of order 0.1 ms, 1 ms, or 10 ms, for instance. Rectangular ON/OFF modulations (having duty-cycles different from 50%-50%) also can be used to modulate each instance 372 of the probe-light. FIG. 3E shows a graph 322 that illustrates the detector signal 312 for a finite time interval $0$-$t_3$ over which the optical path difference $m\Delta z$ is maintained constant, where m is one of $0, \pm 1, \pm 2, \ldots, \pm m_{max}$. Although a level of contributions from noise light 382, 384 or 386 decreases before $t_1$, remains constant at a low level between $t_1$ and $t_2$, and jumps to a higher level after $t_2$, the amplitude of the modulation of the modulated instance of the probe-light transmitted through the witness sample 309, referenced as 376, remains relatively constant over the entire time interval $0$-$t_3$ over which light is collected by the detector OD, for the current optical path difference $m\Delta z$ of the interferometer. As such, the measurement signal $V(m\Delta z)$ 315 for the current optical path difference $m\Delta z$ of the interferometer—which is proportional to the amplitude of the spectral component of the detector signal 312 at the modulation 345's frequency—is approximately constant over the measurement time interval $0$-$t_3$.

To obtain a new measurement signal $V((m+1)\Delta z)$ 315 for a subsequent optical path difference $(m+1)\Delta z$ of the interferometer, the second mirror 366 of the interferometer is translated on the translation stage 368 to a subsequent location $z_0+(m+1)\Delta z$ to change the optical path difference of the interferometer by $\Delta z$ relative to previous optical path difference $m\Delta z$ maintained during the previous measurement point. The new optical path difference $(m+1)\Delta z$ corresponds to a new instance 372 of the probe-light output by the interferometer that is spectrally different from the instance used to take the previous measurement point. The new instance 372 of the probe-light is modulated with the chopper 340 to obtain a new modulated instance 374 of the probe-light that illuminates the witness sample 309 for the finite measurement time interval, e.g., $0$-$t_3$. The new modulated instance of the probe-light transmitted through the witness sample 309, referenced as 376, is collected with the detector OD, along with the noise light 382, 384 or 386, and converted into a new detector signal 312 corresponding to the new optical path difference $(m+1)\Delta z$ of the interferometer. The new measurement signal $V((m+1)\Delta z)$ 315 for the current optical path difference $(m+1)\Delta z$ of the interferometer is the output of the lock-in detection module 350, referenced by the timing of the modulation 345 shown in FIG. 3D, and is proportional to the amplitude of the spectral component of the detector signal 312 at the modulation 345's frequency over the measurement time interval $0$-$t_3$.

Figure 3F:
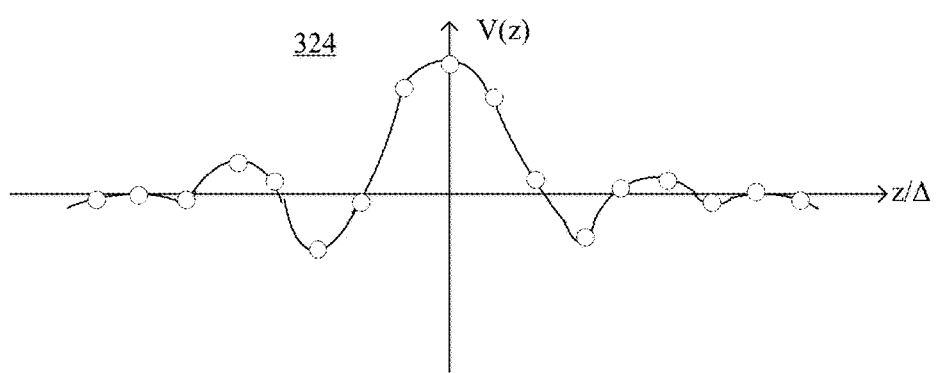

Using the above step-scan mode, the computer system 305 records a set of values $\{V(-m_{max}\Delta z), \ldots, V(-2\Delta z), V(-\Delta z), V(0), V(+\Delta z), V(+2\Delta z), \ldots, V(+m_{max}\Delta z)\}$ of the lock-in signal 315 output by the spectrometer 304 to represent amplitudes of the modulation of the modulated instances of the probe-light transmitted through the witness sample 309, referenced as 376, for the corresponding optical path differences $\{-m_{max}\Delta z, \ldots, -2\Delta z, -\Delta z, 0, +\Delta z, +2\Delta z, \ldots, +m_{max}\Delta z\}$ of the interferometer. FIG. 3F shows a graph 324 in which the recorded set of values $\{V(m\Delta z), m=0, \pm 1, \pm 2, \ldots, \pm m_{max}\}$ is represented as open circles as a function of optical path difference (using normalized units for the optical path difference, $z/\Delta z$.) The computer system 305 fits the set of values represented in graph 324 to obtain, represented in solid line, the amplitude $V(z)$ of the modulation of the modulated instances of the probe-light transmitted through the witness sample 309, referenced as 376, as a function of optical path difference of the interferometer. For example, the fit $V(z)$ is obtained by interpolating the recorded finite set of values $\{V(-m_{max}\Delta z), \ldots, V(-2\Delta z), V(-\Delta z), V(0), V(+\Delta z), V(+2\Delta z), \ldots, V(+m_{max}\Delta z)\}$ for optical path differences z between $[-m_{max}\Delta z, +m_{max}\Delta z]$, and extrapolating the recorded values for optical path differences $z<-m_{max}\Delta z$, and $z>+m_{max}\Delta z$.

Figure 3G:
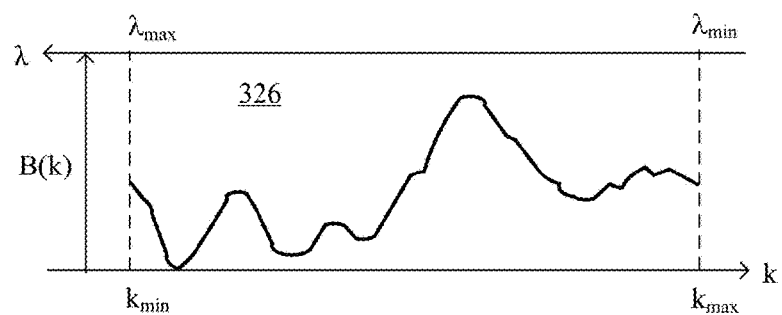

The computer system 305 can Fourier transform the obtained fit $V(z)$ to generate a spectrum $B(k)$ in wavenumber domain (also referred to as spatial frequency domain) for probe-light—with wavelengths in the measurement spectral range $[\lambda_{min}, \lambda_{max}]$—transmitted through the witness sample 309. FIG. 3G shows a graph 326 in which the generated spectrum $B(k)$ is represented, in solid line, only between a minimum wave-number $k_{min}=2\pi/\lambda_{max}$ and a maximum wave-number $k_{max}=2\pi/\lambda_{min}$ corresponding to respective maximum and minimum bounds of the measurement spectral range $[\lambda_{min},\lambda_{max}]$. The generated spectrum B(k) can also be expressed as a function of wavelength to obtain the spectrum S(λ;j) of the probe-light transmitted through the formed layers L(1), . . . , L(j) of the witness sample 309.

Additionally, the computer system 305 can use the obtained spectrum S(λ;j), over the wavelength range from $\lambda_{min}$ to $\lambda_{max}$, along with Fresnel's equations for propagating the probe-light through the formed layers to determine the complex refractive indices and thicknesses of each of the formed layers: $n^{*'}_{Si}$, $n^{*'}_{SiO2}$, t'(1), t'(2), . . . , t'(j−1), t'(j).

The in-situ spectroscopies described above in connection with FIGS. 3A-3B use an interferometer operated in step-scan mode in combination with lock-in detection to detect a modulation of spectrally different instances 372 of probe-light transmitted through a witness sample. Here, the modulation is imparted to the instances 372 of probe-light downstream from the interferometer, but upstream from the witness sample 309. Other ways for imparting the modulation to the probe-light are described below.

Pulse-Modulated Emission of Probe-Light Used as Interferometer Input

Figure 4:
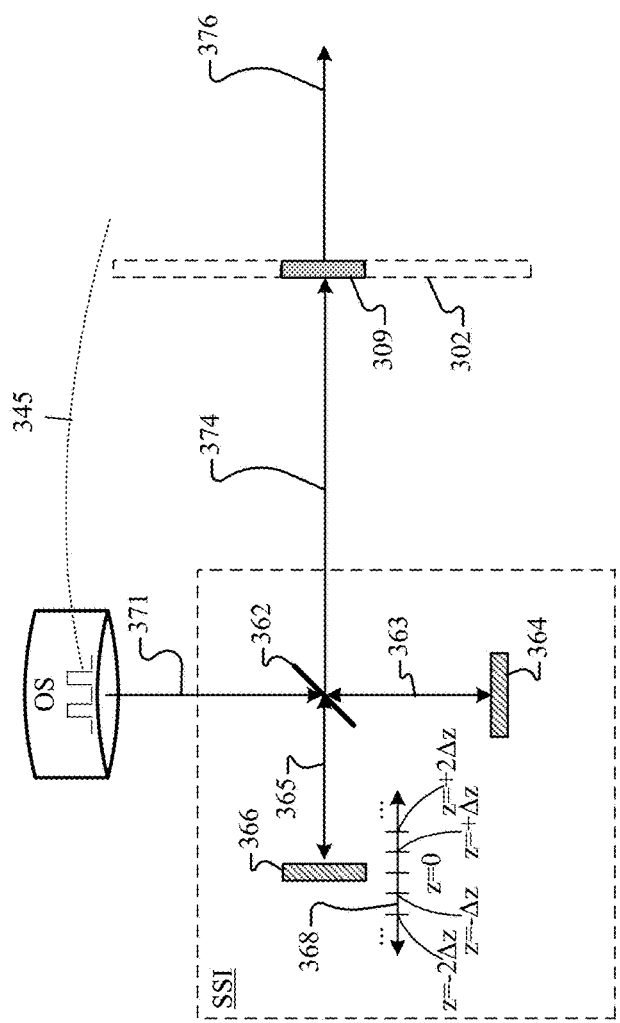
FIG. 4 shows aspects of another implementation of the system for fabricating ICEs that uses the in-situ interferometer-based spectrometer in which the probe-light is emitted as a pulse modulation.

FIG. 4 shows a portion of the optical path of the spectrometer 304 upstream relative to the witness sample 309. Note that the portion illustrated in FIG. 4 represents a modified version of the corresponding portion of FIG. 3A. For example, the optical chopper 340 shown in FIG. 3A is removed from the portion of the optical path shown in FIG. 4. Instead, the source OS outputs modulated probe-light 371 over the wavelength range from $\lambda_{min}$ to $\lambda_{max}$. In some implementations, a modulation 345 is imparted to the probe-light 371 by pulsing the power provided to the source OS to emit pulse-modulated probe-light 371. In other implementations, the probe-light is emitted by the source OS continuously and it is modulated internally, e.g., with a shutter, to output the modulated probe-light 371. Alternatively to the amplitude modulation of the probe-light 371 described above, the modulation 345 can be a frequency or phase modulation. A timing of the modulation 345 is used as a reference signal by the lock-in detection module 350 as described above in connection with FIGS. 3C-3D.

The modulated probe-light 371 output by the source OS is received by the interferometer. The beam-splitter 362 transmits a first portion of the modulated probe-light 371 and reflects a second portion of the modulated probe-light 371. The first and second portions of the modulated probe-light impinging on the beam-splitter 362 after propagation respectively along the fixed 363 and variable 365 arms of the interferometer have wavelengths spanning the measurement spectral range $[\lambda_{min},\lambda_{max}]$. Moreover, the beam-splitter 362 combines the first and second portions of the modulated probe-light impinging on the beam-splitter 362 into combined modulated light 374 that includes a subset of the wavelengths of the measurement spectral range $[\lambda_{min},\lambda_{max}]$. Specifically, the combined modulated light 374 includes those wavelengths of the measurement spectral range $[\lambda_{min},\lambda_{max}]$ that interfere constructively for a current optical path difference between the fixed 363 and variable 365 arms of the interferometer, and lacks those wavelengths of the measurement spectral range $[\lambda_{min},\lambda_{max}]$ that interfere destructively for the current optical path difference. The combined modulated light 374 represents (and is referred to as) a modulated instance 374 of the probe-light output by the interferometer for the current optical path difference. In this manner, a plurality of modulated instances 374 of the probe-light corresponding to a plurality of optical path differences of the interferometer can be provided by discretely scanning the location of the second mirror 366 along the translation stage 368.

FIGS. 4 and 3C show that each modulated instance 374 of the probe-light is directed into the deposition chamber 301 through an input port associated with the spectrometer 304 (not shown in FIGS. 4 and 3C) to illuminate the witness sample 309 supported by the substrate support 302, which is at rest, in this example. Each modulated instance of the probe-light transmitted through the witness sample 309, referenced as 376, is directed outside the deposition chamber 301 through an exit port associated with the spectrometer 304 (not shown in FIGS. 4 and 3C) to be collected by the detector OD. All other aspects of the disclosed technologies described in connection with FIGS. 3C-3G are applicable in conjunction with the aspects described above in connection with FIG. 4.

The in-situ spectroscopies described above in connection with FIGS. 3A-3B and 4 use lock-in detection to detect a modulation of spectrally different instances 376 of probe-light transmitted through a witness sample. Here, the spectrally different instances 374 of probe-light are provided using an interferometer operated in step-scan mode. Other ways for providing the spectrally different instances 374 of probe-light are described below.

(3.2) System for ICE Fabrication Equipped with a Monochromator-Based Spectrometer Operated in Step-Scan Mode in Combination with Lock-in Detection Technologies for in-situ monitoring of ICE fabrication using spectra of current instances of ICEs being fabricated are described below, such that the spectra are generated from results of step-scan spectroscopy performed with a monochromator-based spectrometer in combination with lock-in detection.

Figure 5A:
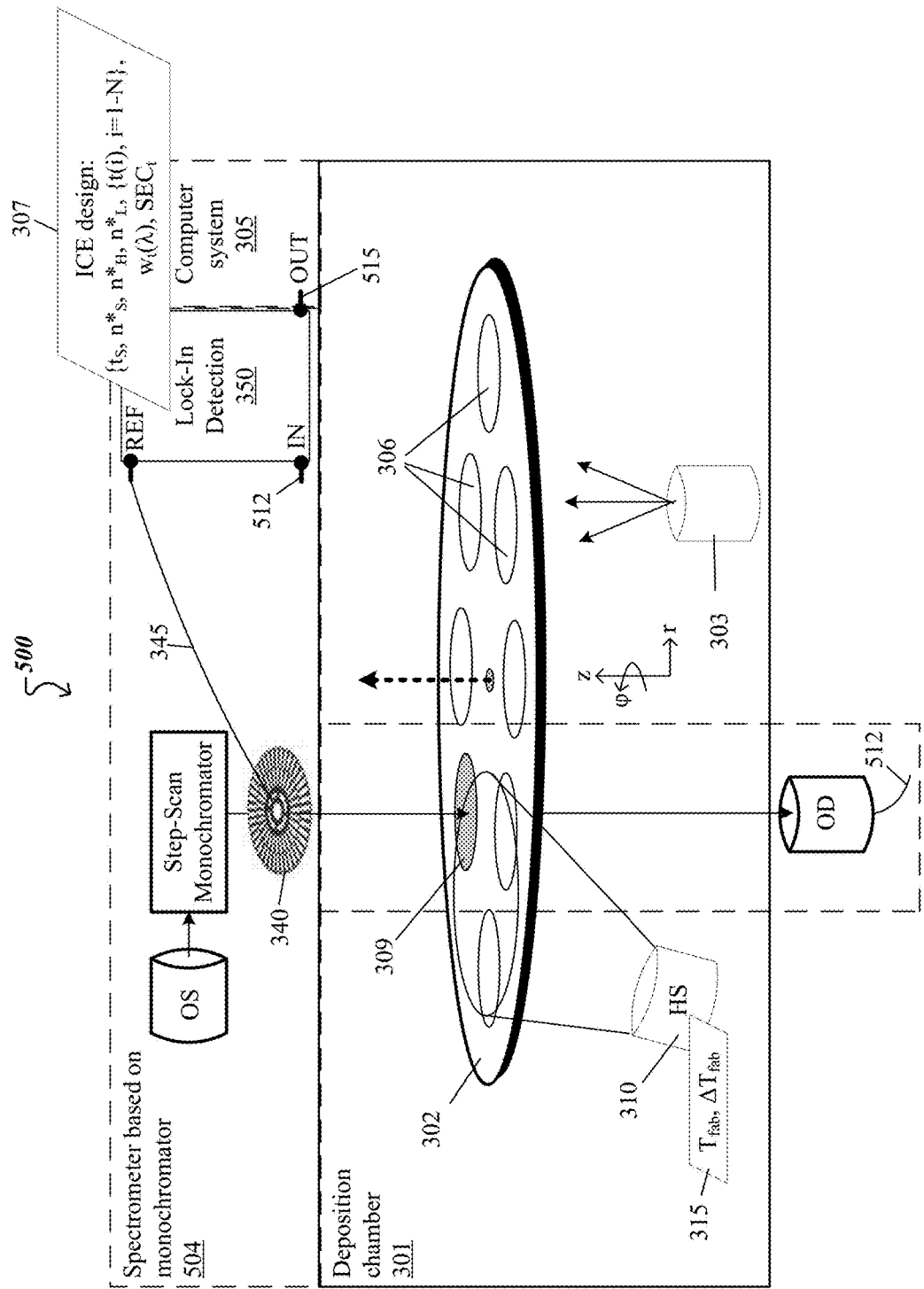
FIGS. 5A-5D show aspects of an implementation of another system for fabricating ICEs that uses an in-situ monochromator-based spectrometer operated in step-scan mode—to provide probe-light modulated with an optical chopper to illuminate witness samples—in combination with the lock-in detection module—that detects the modulation of the probe-light that interacts with the witness samples—to monitor fabrication of the ICEs.

FIG. 5A shows an example of an ICE fabrication system 500. The ICE fabrication system 500 includes a deposition chamber 301 to fabricate one or more ICEs 306, a spectrometer 504 to acquire spectra of probe-light that interacted with formed layers of the ICEs while the ICEs are being fabricated, and a computer system 305 to control the fabrication of the one or more ICEs based at least in part on the acquired spectra.

The deposition chamber 301 includes one or more deposition sources 303 to provide materials with a low complex index of refraction $n^*_L$ and a high complex index of refraction $n^*_H$ used to form layers of the ICEs 306. Substrates on which layers of the ICEs 306 will be deposited are placed on a substrate support 302, such that the ICEs 306 are within the field of view of the deposition source(s) 303. The substrates have a thickness $t_S$ and a complex refraction index $n^*_S$ specified by a target ICE design 307, e.g., ICE design 145 or 245.

A heating source 310 provides heat to the current instances of the ICEs 306 distributed on the substrate support 302 to maintain their temperature within a target fabrication temperature range $\Delta T_{fab}$ around a target fabrication temperature $T_{fab}$. A process parameter 315 that includes the target fabrication temperature $T_{fab}$ and the target fabrication temperature range $\Delta T_{fab}$ is accessed by the computer system 305 and used to control the temperature of current instances of ICEs 306 during fabrication of ICEs associated with the ICE design 307.

As described above in connection with FIG. 3A, power provided to the source(s) 303, its(their) arrangement relative to the one or more substrate supports 302, etc., are used to control deposition rate(s) R of the source(s) 303. The actual complex refractive indices and thicknesses of the deposited layers L(1), . . . , L(j−1), L(j) can be determined when the deposition of the current layer L(j) is interrupted, e.g., with 10% left of the duration T(j), or when the deposition is completed at the end of the duration T(j). The complex refractive indices and thicknesses of the formed layers are determined in near real-time from a spectrum $S(\lambda;j)$ of probe-light that interacted with the formed layers L(1), . . . , L(j−1), L(j) acquired by the spectrometer 504.

The spectrometer 504 includes an optical source (OS) to emit probe-light having a wavelength range from $\lambda_{min}$ to $\lambda_{max}$, and a monochromator to receive the probe-light and to provide spectrally different instances of the probe-light corresponding to different relative orientations of a wavelength selector and an exit slit of the monochromator. Here, the monochromator is operated in step-scan mode, such that each of the instances of the probe-light is provided for a finite (non-zero) time interval. As in this example the monochromator is operated in step-scan mode, it will also be referred to as a step-scan monochromator (SSM). Further, spectrometer 504 includes an optical chopper 340 to modulate the instances of the probe-light over the finite time interval with a modulation 345. The modulated instances of the probe-light are provided through an entry port associated with the spectrometer 504 into the deposition chamber 301 to illuminate a witness sample 309. Here, the witness sample 309 is supported on the substrate support 302 along with the ICEs 306 being formed in the deposition chamber 301, so the witness sample 309 experiences the same periodic motion with respect to the deposition source(s) 303 as the ICEs 306 during deposition. The formed layers of any one or more of the current instances of the ICEs 306 can be used as a witness sample by the spectrometer 504 to monitor ICE layer deposition in the deposition chamber 301. In the example implementation illustrated in FIG. 5A, the substrate support 302, and thus the witness sample 309, is maintained at rest while the spectrometer 504 acquires a spectrum $S(\lambda;j)$. The modulated instances of the probe-light transmitted through the witness sample 309 are output from the deposition chamber 301 through an exit port associated with the spectrometer 504.

Furthermore, the spectrometer 504 includes an optical detector (OD) to collect light that exits the deposition chamber through the exit port, where the collected light includes the modulated instances of the probe-light transmitted through the witness sample 309, and light emitted by various noise sources, e.g., the heat source(s) 310, from the deposition chamber 310 or elsewhere in the environment of the ICE fabrication system 500. The detector OD converts the collected light to a detector signal 512. Additionally, the spectrometer 504 includes a lock-in detection module 350—synchronized with the modulation 345 induced by the chopper 340 in the instances of the probe-light—to process the detector signal 512. A lock-in signal 515 of the lock-in detection module 350 (also referred to as a measurement signal 515) is proportional to a spectral amplitude of the detector signal 512 at a frequency of the modulation 345. In this manner, the measurement signal 515 represents an average of amplitudes of the instances of the probe-light transmitted through the witness sample 309 over at least a portion of the finite time interval.

The computer system 305 uses a set of values of the measurement signal 515 corresponding to the different spectral instances of the probe-light to generate a spectrum $S(\lambda;j)$ of probe-light transmitted through the formed layers L(1), . . . , L(j−1), L(j) of the witness sample 309. The generated spectrum $S(\lambda;j)$, over the wavelength range from $\lambda_{min}$ to $\lambda_{max}$, can be used by the computer system 305 to determine the complex refractive indices and thicknesses of each of the formed layers in the stack: $n^{*'}_{SiO2}$, t'(1), t'(2), . . . , t'(j−1), t'(j). The computer system 305 makes this determination by solving Fresnel's equations for propagating the interacted probe-light through the formed layers in the stack.

Various components of the spectrometer 504 and their corresponding functions are now described in detail.

Figure 5B:
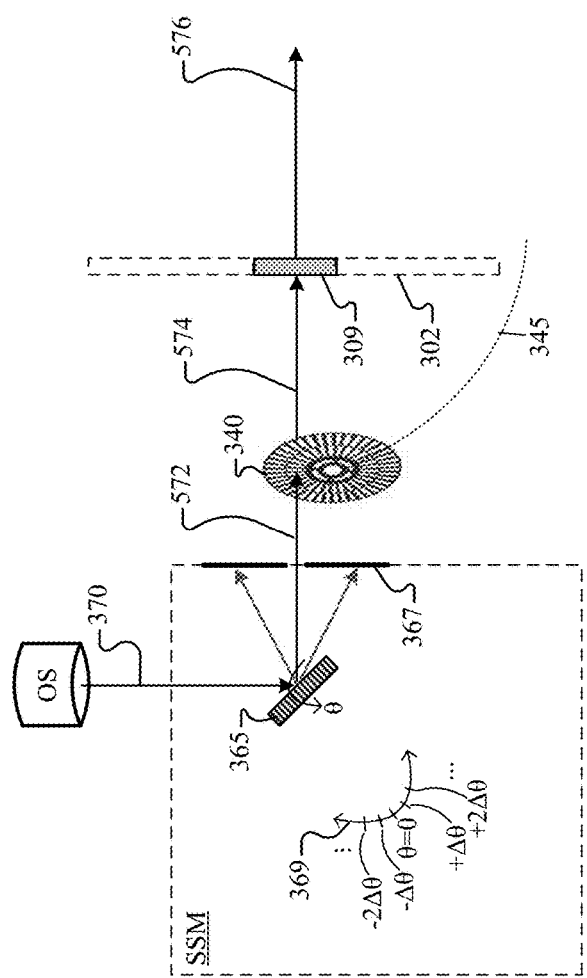

FIG. 5B shows a portion of the optical path of the spectrometer 504 upstream relative to the witness sample 309. Note that the portion illustrated in FIG. 5B represents a corresponding portion of FIG. 5A. The source OS of the spectrometer 504 outputs the probe-light 370 over a measurement spectral range $[\lambda_{min},\lambda_{max}]$. The monochromator includes a diffractive element 365 mounted on a rotation stage 369. The diffractive element 365, e.g., a grating, angularly separates the probe-light 370 into its constituent wavelengths from $\lambda_{min}$ to $\lambda_{max}$. In other implementations, another wavelength selector can be used to angularly separate the probe-light 370 into its constituent wavelengths, such as a dispersive element, e.g., a prism. An exit slit 367 (also referred to as on exit port) is placed in the path of the angularly separated probe-light to pass a quasi-monochromatic portion 572 of the angularly separated probe-light and to block the remaining angularly separated probe-light. The quasi-monochromatic portion 572 of the angularly separated probe-light passed by the exit slit 367 has wavelengths centered on a particular wavelength corresponding to a relative angular orientation $\Delta\theta$ between the diffractive element 365 and the exit slit 367, and a narrow wavelength range $\Delta\lambda$, e.g., 5, 10, or 20 nm in the visible range, or 1, 2, or 5μ in the IR range. Moreover, the quasi-monochromatic portion 572 of the angularly separated probe-light passed by the exit slit 367 represents (and is referred to as) an instance of the probe-light 370 output by the monochromator for the current relative angular orientation $\Delta\theta$ between the diffractive element 365 and the exit slit 367.

In this manner, a plurality of spectrally-different instances 572 of the probe-light corresponding to a plurality of relative angular orientations between the diffractive element 365 and the exit slit 367 can be provided by discretely scanning, along the rotation stage 369, the relative angle $\Delta\theta$ between the diffractive element 365 and the exit slit 367. When the relative angle is $\Delta\theta=0$, an instance 572-0 of the probe-light having a center-wavelength $\lambda_0$ is provided by the monochromator. When the relative angle is $+\Delta\theta$ (or equivalently, when the diffractive element 365 is rotated by an angle increment $+\Delta\theta$ relative to the exit slit 367), a first instance 572-1 of the probe-light—having a center-wavelength $\lambda_1$ different from $\lambda_0$—is provided by the monochromator. When the relative angle is $+2\Delta\theta$ (or equivalently, when the diffractive element 365 is rotated by $+2\Delta\theta$ relative to the exit slit 367), a second instance 572-2 of the probe-light—having a center-wavelength $\lambda_2$ different from $\lambda_0$ and $\lambda_1$—is provided by the monochromator. And so on, other instances 572-m of the probe-light—that are spectrally different from each other—are provided by the monochromator for corresponding relative angles of $\pm m\Delta\theta$, where m=0, ±1, . . . , $\pm m_{max}$.

Each instance 572 of the probe-light provided by the monochromator is modulated with the optical chopper 340. The optical chopper 340 imparts a modulation 345 to each instance 572 of the probe-light and outputs a modulated instance 574 of the probe-light. A timing of the modulation 345 is used as a reference signal by the lock-in detection module 350 as described in detail below.

FIGS. 5B and 3C show that each modulated instance 574 of the probe-light is directed into the deposition chamber 301 through an input port associated with the spectrometer 504 (not shown in FIGS. 5B and 3C) to illuminate the witness sample 309 supported by the substrate support 302, which is at rest, in this example. Each modulated instance of the probe-light transmitted through the witness sample 309, referenced as 576, is directed outside the deposition chamber 301 through an exit port associated with the spectrometer 504 (not shown in FIGS. 5B and 3C) to be collected by the detector OD.

Referring again to FIG. 3C, which shows an optical path of the spectrometer 504 downstream relative to the witness sample 309, it is noted that the portion illustrated in FIG. 3C represents a corresponding portion of FIG. 5A. In addition to the modulated instance of the probe-light transmitted through the witness sample 309, referenced as 576, the detector OD collects light 382, 384 or 386 emitted by noise sources within the deposition chamber (e.g., the heating sources 310 described above) or from elsewhere within the environment of the ICE fabrication system 500.

The light collected by the detector OD, including the modulated light 576 and the noise light 382, 384 or 386, is converted into detector signal 512. The lock-in detection module 350 is referenced by a timing of the modulation 345 and receives as input the detector signal 512. For a current relative orientation $m\Delta\theta$ between the diffractive element 365 and the exit slit 367, where m is one of 0, ±1, ±2, . . . , ±$m_{max}$, intensity variation of the detector signal 512 can include the modulation 345 of the modulated instance of the probe-light transmitted through the witness sample 309, referenced as 576, and intensity changes of the noise light 382, 384 or 386. Moreover, at the current relative orientation $m\Delta\theta$ between the diffractive element 365 and the exit slit 367, the amplitude of the modulation 345 of the modulated instance of the probe-light transmitted through the witness sample 309, referenced as 576, is constant for constant emission of probe-light 370 by the source OS. As such, the lock-in signal 515 (also referred to as the measurement signal 515) is proportional to spectral amplitude of the detector signal 512 at a frequency of the reference signal 345. In this manner, the measurement signal 515 represents an average over multiple modulation periods of the intensity of the modulated instance of the probe-light transmitted through the witness sample 309, referenced as 576.

FIG. 3D shows a graph 320 that illustrates an example of a reference signal of the lock-in detection module 350 corresponding to the modulation 345 imparted by the chopper 340 to each instance 572 of the probe-light. FIG. 3E shows a graph 322 that illustrates the detector signal 512 for a finite time interval $0-t_3$ over which the relative orientation $m\Delta\theta$ between the diffractive element 365 and the exit slit 367 is maintained constant, where m is one of 0, ±1, ±2, . . . , ±$m_{max}$. Although a level of contributions from noise light 382, 384 or 386 decreases before $t_1$, remains constant at a low level between $t_1$ and $t_2$, and jumps to a higher level after $t_2$, the amplitude of the modulation of the modulated instance of the probe-light transmitted through the witness sample 309, referenced as 576, remains relatively constant over the entire time interval $0-t_3$ over which light is collected by the detector OD, for the current relative orientation $m\Delta\theta$ between the diffractive element 365 and the exit slit 367. As such, the measurement signal $V(m\Delta\theta)$ 515 for the current relative orientation $m\Delta\theta$ between the diffractive element 365 and the exit slit 367—which is proportional to the amplitude of the spectral component of the detector signal 512 at the modulation 345's frequency—is approximately constant over the measurement time interval $0-t_3$.

To obtain a new measurement signal $V((m+1)\Delta\theta)$ 515 for a subsequent relative orientation $(m+1)\Delta\theta$ between the diffractive element 365 and the exit slit 367, the diffractive element 365 of the monochromator is rotated on the rotation stage 369 to a subsequent relative angular location $(m+1)\Delta\theta$ to change the relative orientation between the diffractive element 365 and the exit slit 367 by $\Delta\theta$ relative to previous relative orientation $m\Delta\theta$ maintained during the previous measurement point. The new relative orientation $(m+1)\Delta\theta$ corresponds to a new instance 572 of the probe-light output by the monochromator that is spectrally different from the instance used to take the previous measurement point. The new instance 572 of the probe-light is modulated with the chopper 340 to obtain a new modulated instance 574 of the probe-light that illuminates the witness sample 309 for the finite measurement time interval, e.g., $0-t_3$. The new modulated instance of the probe-light transmitted through the witness sample 309, referenced as 576, is collected with the detector OD, along with the noise light 382, 384 or 386, and converted into a new detector signal 512 corresponding to the new relative orientation $(m+1)\Delta\theta$ between the diffractive element 365 and the exit slit 367. The new measurement signal $V((m+1)\Delta\theta)$ 515 for the current relative orientation $(m+1)\Delta\theta$ between the diffractive element 365 and the exit slit 367 is the output of the lock-in detection module 350, referenced by the timing of the modulation 345 shown in FIG. 3D, and is proportional to the amplitude of the spectral component of the detector signal 512 at the modulation 345's frequency over the measurement time interval $0-t_3$.

Figure 5C:
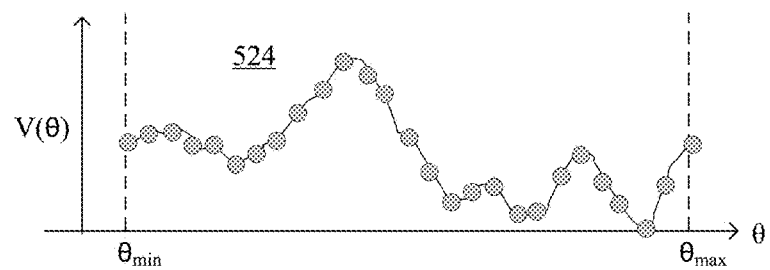

Using the above step-scan mode, the computer system 305 records a set of values $\{V(\theta_{min}), V(-2\Delta\theta), V(-\Delta\theta), V(0), V(+\Delta\theta), V(+2\Delta\theta), \ldots, V(\theta_{max})\}$ of the lock-in signal 515 output by the spectrometer 304 to represent amplitudes of the modulation of the modulated instances of the probe-light transmitted through the witness sample 309, referenced as 576, for the corresponding relative orientations $\{\theta_{min}, \ldots, -2\Delta\theta, -\Delta\theta, 0, +\Delta\theta, +2\Delta\theta, \ldots, +\theta_{max}\}$ between the diffractive element 365 and the exit slit 367. FIG. 5C shows a graph 524 in which the recorded set of values $\{V(\theta_{min}), \ldots, V(-2\Delta\theta), V(-\Delta\theta), V(0), V(+\Delta\theta), V(+2\Delta\theta), \ldots, V(\theta_{max})\}$ is represented as filled circles as a function of relative orientation between the diffractive element 365 and the exit slit 367 (using normalized units for the relative orientation, $\theta/\Delta\theta$.) The computer system 305 fits the set of values represented in graph 524 to obtain, represented in solid line, the amplitude $V(\theta)$ of the modulation of the modulated instances of the probe-light transmitted through the witness sample 309, referenced as 576, as a function of relative orientation between the diffractive element 365 and the exit slit 367. For example, the fit $V(\theta)$ is obtained by interpolating the recorded finite set of values $\{V(\theta_{min}), \ldots, V(-2\Delta\theta), V(-\Delta\theta), V(0), V(+\Delta\theta), V(+2\Delta\theta), \ldots, V(\theta_{max})\}$ for relative orientations between $[\theta_{min}, \theta_{max}]$, and extrapolating the recorded values for relative orientations $\theta<\theta_{min}$, and $\theta>\theta_{max}$.

Figure 5D:
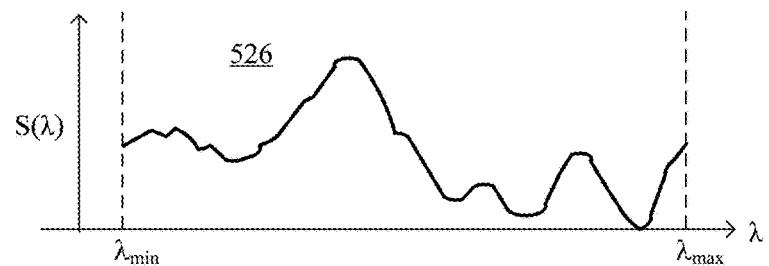

The computer system 305 can correlate angles of the angular range $[\theta_{min}, \theta_{max}]$ of the described step-scan with wavelengths of the measurement spectral range $[\lambda_{min}, \lambda_{max}]$, and further appropriately scale, normalize, etc. the obtained fit $V(\theta)$ to generate a spectrum $S(\lambda;j)$ of probe-light transmitted through the formed layers $L(1), \ldots, L(j)$ of the witness sample 309. FIG. 5D shows a graph 526 in which the generated spectrum $S(\lambda;j)$ is represented in solid line over the measurement spectral range $[\lambda_{min}, \lambda_{max}]$. As noted above, the computer system 305 can use the generated spectrum $S(\lambda;j)$—illustrated in FIG. 5D—along with Fresnel's equations for propagating the probe-light through the formed layers to determine the complex refractive indices and thicknesses of each of the formed layers: $n^{*'}{}_{Si}$, $n^{*'}{}_{SiO2}$, $t'(1), t'(2), \ldots, t'(j-1), t'(j)$.

The in-situ spectroscopies described above in connection with FIGS. 5A-5B use a monochromator operated in step-scan mode in combination with lock-in detection to detect a modulation of spectrally different instances 576 of probe-light transmitted through a witness sample. Here, the modulation is imparted to the instances 572 of probe-light downstream from the monochromator, but upstream from the witness sample 309. Other ways for imparting the modulation to the probe-light are described below.

Pulse-Modulated Emission of Probe-Light Used as Monochromator Input

Figure 6:
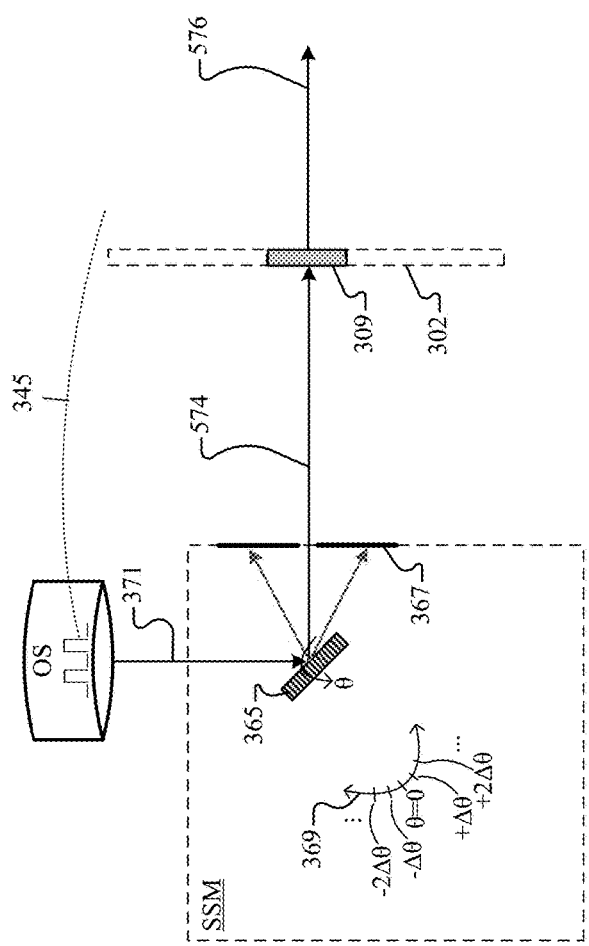
FIG. 6 shows aspects of another implementation of the system for fabricating ICEs that uses the in-situ monochromator-based spectrometer in which the probe-light is emitted as a pulse modulation.

FIG. 6 shows a portion of the optical path of the spectrometer 504 upstream relative to the witness sample 309. Note that the portion illustrated in FIG. 6 represents a modified version of the corresponding portion of FIG. 5A. For example, the optical chopper 340 shown in FIG. 5A is removed from the portion of the optical path shown in FIG. 6. Instead, the source OS outputs modulated probe-light 371 over the wavelength range from $\lambda_{min}$ to $\lambda_{max}$. A timing of the modulation 345 is used as a reference signal by the lock-in detection module 350 as described above in connection with FIGS. 3C-3D.

The modulated probe-light 371 output by the source OS is received by the monochromator. The diffractive element 365 angularly separates the modulated probe-light 371 into its constituent wavelengths from $\lambda_{min}$ to $\kappa_{max}$, and the exit slit 367 passes only a modulated quasi-monochromatic portion 574 of the angularly separated probe-light corresponding to the current relative orientation $\Delta\theta$ between the diffractive element 365 and the exit slit 367. The modulated quasi-monochromatic portion 574 of the angularly separated probe-light passed by the exit slit 367 represents (and is referred to as) a modulated instance 574 of the probe-light output by the monochromator for the current relative orientation $\Delta\theta$ between the diffractive element 365 and the exit slit 367. In this manner, a plurality of modulated instances 574 of the probe-light corresponding to a plurality of relative orientations between the diffractive element 365 and the exit slit 367 can be provided by discretely scanning the angular coordinate of the diffractive element 365 along the rotation stage 369.

FIGS. 6 and 3C show that each modulated instance 574 of the probe-light is directed into the deposition chamber 301 through an input port associated with the spectrometer 504 (not shown in FIGS. 6 and 3C) to illuminate the witness sample 309 supported by the substrate support 302, which is at rest, in this example. Each modulated instance of the probe-light transmitted through the witness sample 309, referenced as 576, is directed outside the deposition chamber 301 through an exit port associated with the spectrometer 504 (not shown in FIGS. 6 and 3C) to be collected by the detector OD. All other aspects of the disclosed technologies described in connection with FIGS. 3C-3D and 5C-5D are applicable in conjunction with the aspects described above in connection with FIG. 6.

The in-situ spectroscopies described above in connection with FIGS. 3A-3B, 4, 5A-5B, 6, 3C-3E and 5C-5D use an interferometer or a monochromator, both operated in step-scan mode, in combination with lock-in detection to detect a modulation 345 of spectrally different instances 376 or 576 of probe-light transmitted through a witness sample. Here, modulated probe-light 371 is emitted by the source OS, or the modulation 345 is imparted to instances 372 or 572 of probe-light downstream from the interferometer or monochromator, but upstream from the witness sample 309. Other ways for imparting a modulation to spectrally different instances 272 of probe-light transmitted through the witness sample 309 and for detecting the differently imparted modulation are described below.

(3.3) System for ICE Fabrication Equipped with an Interferometer-Based Spectrometer Operated in Step-Scan Mode in Combination with Time-Gated Detection Technologies for in-situ monitoring of ICE fabrication using spectra of current instances of ICEs being fabricated are described below, such that the spectra are generated from results of step-scan spectroscopy performed with an interferometer-based spectrometer in combination with time-gated detection.

Figure 7A:
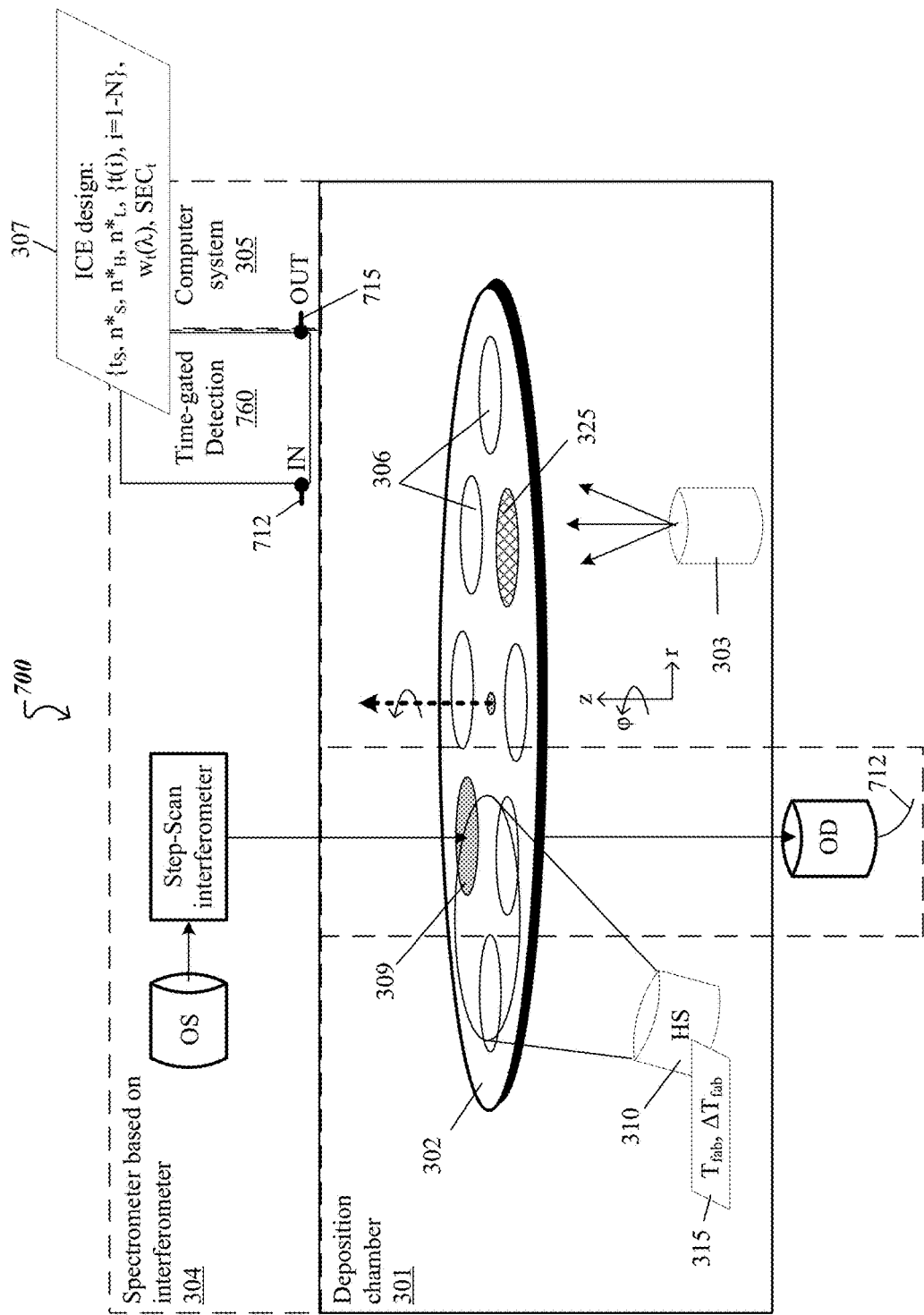
FIGS. 7A-7E show aspects of a system for fabricating ICEs that uses an in-situ interferometer-based spectrometer operated in step-scan mode—to periodically illuminate witness samples with un-modulated probe-light—in combination with a time-gated detection module—that detects a modulation of the probe-light that interacts with the witness samples, the modulation being caused by the periodic illumination—to monitor fabrication of the ICEs.

FIG. 7A shows an example of an ICE fabrication system 700. The ICE fabrication system 700 includes a deposition chamber 301 to fabricate one or more ICEs 306, a spectrometer 304 to acquire spectra of probe-light that interacted with formed layers of the ICEs while the ICEs are being fabricated, and a computer system 305 to control the fabrication of the one or more ICEs based at least in part on the acquired spectra.

The deposition chamber 301 includes one or more deposition sources 303 to provide materials with a low complex index of refraction $n^*{}_L$ and a high complex index of refraction $n^*{}_H$ used to form layers of the ICEs 306. Substrates on which layers of the ICEs 306 will be deposited are placed on a substrate support 302, such that the ICEs 306 are within the field of view of the deposition source(s) 303. The substrates have a thickness $t_S$ and a complex refraction index $n^*{}_S$ specified by a target ICE design 307. A relative orientation of and separation between the deposition source(s) 303 and the substrate support 302 are configured to provide desired deposition rate(s) and spatial uniformity across the ICEs 306 disposed on the substrate support 302. As a spatial distribution of a deposition plume provided by the deposition source(s) 303 is non-uniform along at least a first direction, the substrate support 302 is periodically moved with respect to the deposition source 303 along the first direction (e.g., rotated along an azimuthal direction "ϕ" about an axis laterally offset from the deposition source(s) 303 that passes through the center of the substrate support 302) to obtain reproducibly uniform layer deposition of the ICEs 306 within a batch.

A heating source 310 provides heat to the current instances of the ICEs 306 distributed on the substrate support 302 to maintain their temperature within a target fabrication temperature range $\Delta T_{fab}$ around a target fabrication temperature $T_{fab}$. A process parameter 315 that includes the target fabrication temperature $T_{fab}$ and the target fabrication temperature range $\Delta T_{fab}$ is accessed by the computer system 305 and used to control the temperature of current instances of ICEs 306 during fabrication of ICEs associated with the ICE design 307.

As described above in connection with FIGS. 3A and 5A, power provided to the deposition source(s) 303, its(their) arrangement relative to the one or more substrate supports 302, etc., are used to control deposition rate(s) R of the source(s) 303. The actual complex refractive indices and thicknesses of the deposited layers L(1), . . . , L(j−1), L(j) can be determined when the deposition of the current layer L(j) is interrupted, e.g., with 10% left of the duration T(j), or when the deposition is completed at the end of the duration T(j). The complex refractive indices and thicknesses of the formed layers are determined in near real-time from a spectrum $S(\lambda;j)$ of probe-light that interacted with the formed layers L(1), . . . , L(j−1), L(j) acquired by the spectrometer 304.

The spectrometer 304 includes an optical source (OS) to emit probe-light having a wavelength range from $\lambda_{min}$ to $\lambda_{max}$, and an interferometer to receive the probe-light and to provide spectrally different instances of the probe-light corresponding to different optical path differences of the interferometer. Here, the interferometer is operated in step-scan mode, such that each of the instances of the probe-light is provided for a finite (non-zero) time interval. In this manner, the spectrometer 304 provides un-modulated instances of the probe-light—through an entry port associated with the spectrometer 304—into the deposition chamber 301 to illuminate a witness sample 309. Here, the witness sample 309 is supported on the substrate support 302 along with the ICEs 306 being formed in the deposition chamber 301, so the witness sample 309 experiences the same periodic motion with respect to the deposition source(s) 303 as the ICEs 306 during deposition. In the example implementation illustrated in FIG. 7A, the periodic motion of the substrate support 302, and thus, of the witness sample 309, is maintained while the spectrometer 304 acquires a spectrum $S(\lambda;j)$. Additionally in this example, at least one aperture 325 is disposed on the support substrate 302, spaced apart from the witness sample 309. In the example illustrated in FIG. 7A, the aperture 325 has the same size as the witness sample 309 and is disposed at 12 o'clock on the platen 302, while the witness sample 309 is disposed at 6 o'clock on the platen 302, at the same radius as the aperture 325. In this manner, a current instance of the probe-light provided by the spectrometer 304 into the deposition chamber 301 alternately illuminates the aperture 325 and the witness sample 309. As such, a modulation is imparted to the current instance of the probe-light that propagates downstream from the substrate support 302. Timing of the modulation is based on the periodic motion of the aperture 325 and witness sample 309, and amplitude of the modulation is proportional to attenuation of the current instance of the probe-light transmitted through the witness sample 309. Each of the instances of the probe-light passed through the aperture 325 and alternately transmitted through the witness sample 309 is output from the deposition chamber 301 through an exit port associated with the spectrometer 304.

Further, the spectrometer 304 includes an optical detector (OD) to collect light that exits the deposition chamber through the exit port. The collected light includes the current instance of the probe-light alternately passed through the aperture 325 and transmitted through the witness sample 309, and light emitted by various noise sources, e.g., the heat source(s) 310, from the deposition chamber 310 or elsewhere in the environment of the ICE fabrication system 700. The detector OD converts the collected light to a detector signal 712.

Additionally, the spectrometer 304 includes a time-gated detection module 760—that uses timing of the periodic motion of the aperture 325 and the witness sample 309—to gate (or limit) the detector signal 712. For instance, the time-gated detection module 760 limits the detector signal 712 to portions of the period of the periodic motion of the aperture 325 and the witness sample 309 when the current instance of the probe-light alternately illuminates the moving aperture 325 and the moving witness sample 309. The timing of the periodic motion of the aperture 325 and the witness sample 309 used by the time-gated detection module 760 to time-gate the detector signal 712 is a function of at least the following parameters: a number K≥1 of pairs of aperture 325 and witness sample 309 on the substrate support 302 (in FIG. 7A, K=1), a period $T_0$ with which the substrate support 302 moves relative to the deposition source(s) 303, a size of the aperture 325 and witness sample 309, and a radius of the substrate supports 302 where the aperture 325 and the witness sample 309 are positioned.

Once the detector signal 712 is time-gated by the time-gated detection module 760 in accordance with the timing of the periodic motion of the aperture 325 and the witness sample 309, the time-gated detector signal is processed by the time-gated detection module 760 to output a measurement signal 715. The processing of the time-gated detector signal includes performing one or more of sample-and-hold between consecutive time-gates, peak-finding during each time-gate, fitting signal-peaks found when the instances of the probe-light illuminate the aperture 325 to obtain a first envelope signal, and fitting other signal-peaks found when the instances of the probe-light illuminate the witness sample 309 to obtain a second envelope signal, and the like. For a single pair of aperture 325 and witness sample 309 (K=1), the foregoing fits are performed over a number of periods of the periodic motion, for instance over 5 periods. For a number K≥2 of pairs of aperture 325 and witness sample 309 (not shown in FIG. 7A), fits are performed over the K pairs during a single period of the periodic motion. In either of the above cases, the measurement signal 715 output by the time-gated detection module 760 is proportional to the amplitude of the modulation of the current instance of the probe-light collected by the detector OD. In this manner, the measurement signal 715 represents the attenuation of the current instance of the probe-light due to transmission through the witness sample 309.

The computer system 305 uses a set of values of the measurement signal 715 corresponding to the different spectral instances of the probe-light to generate a spectrum $S(\lambda;j)$ of probe-light transmitted through the formed layers L(1), . . . , L(j−1), L(j) of the witness sample 309. The generated spectrum $S(\lambda;j)$, over the wavelength range from $\lambda_{min}$ to $\lambda_{max}$, can be used by the computer system 305 to determine the complex refractive indices and thicknesses of each of the formed layers in the stack: $n^{*'}_{Si}$, $n^{*'}_{SiO2}$, $t'(1)$, $t'(2)$, . . . , $t'(j−1)$, $t'(j)$. The computer system 305 makes this determination by solving Fresnel's equations for propagating the interacted probe-light through the formed layers in the stack.

Various components of the spectrometer 304 and their corresponding functions are now described in detail.

Figure 7B:
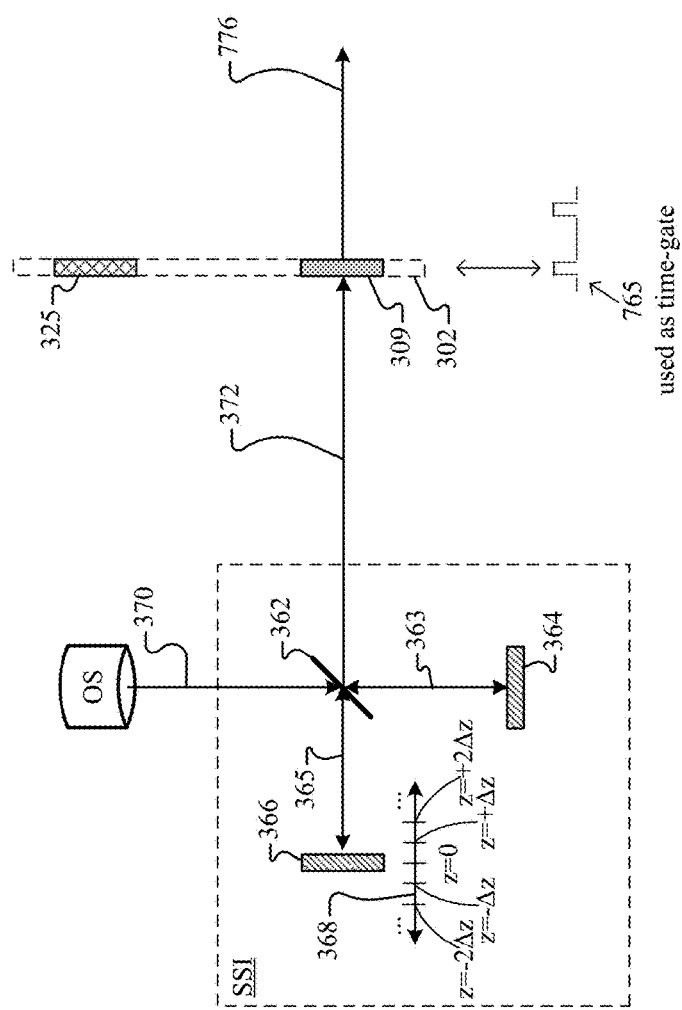
Figure 7C:
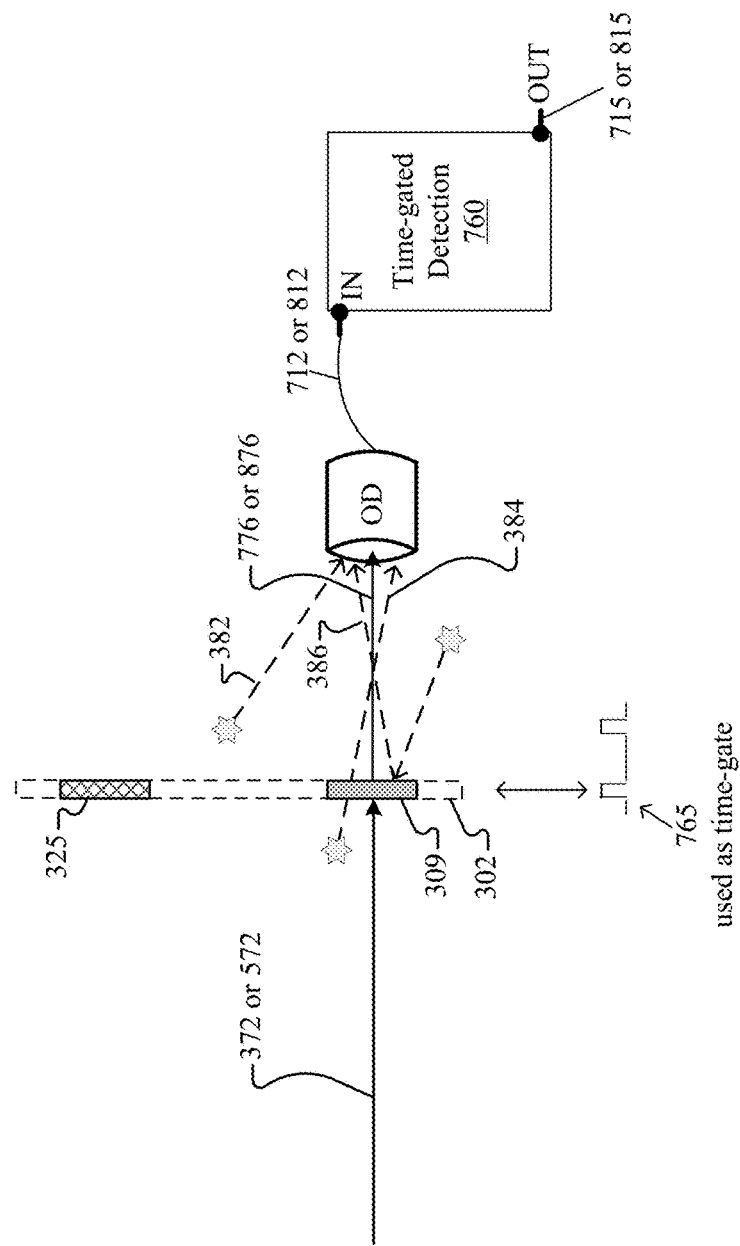

FIG. 7B shows a portion of the optical path of the spectrometer 304 upstream relative to the witness sample 309. Note that the portion illustrated in FIG. 7B represents a corresponding portion of FIG. 7A. The source OS and the interferometer of the spectrometer 304 have been described in detail in connection with FIGS. 3A-3B and 4. A plurality of spectrally-different instances 372-$m$ of the probe-light corresponding to a plurality of different optical path differences $\pm m\Delta z$ of the interferometer, for m=0, ±1, . . . , ±$m_{max}$, can be provided by discretely scanning the location "z" of the second mirror 366 along the translation stage 368. FIGS. 7B and 7C show that each instance 372 of the probe-light is directed into the deposition chamber 301 through an input port associated with the spectrometer 304 (not shown in FIGS. 7B-7C) to alternately illuminate the witness sample 309 supported by and the aperture 325 of the substrate support 302. In this embodiment, the substrate support 302 is periodically moved (e.g., rotated about an axis through the center of the substrate support 302), such that each instance 372 of the probe-light alternately illuminates the witness sample 309 and the aperture 325 based on a timing 765. The timing 765 is used as a time-gate by the time-gated detection module 760 as described in detail below. In this manner, a modulation—having the timing 765 and an amplitude that represents attenuation of each instance 372 of the probe-light transmitted through the witness sample 309—is imparted to the instance 372 of the probe-light that propagates downstream relative to the substrate support 302 to form a modulated instance 776 of the probe-light. Each modulated instance 776 of the probe-light is directed outside the deposition chamber 301 through an exit port associated with the spectrometer 304 (not shown in FIGS. 7B-7C) to be collected by the detector OD.

FIG. 7C shows an optical path of the spectrometer 304 downstream relative to the witness sample 309. Note that the portion illustrated in FIG. 7C represents a corresponding portion of FIG. 7A. In addition to the modulated instance 776 of the probe-light, the detector OD collects light 382, 384 or 386 emitted by noise sources within the deposition chamber (e.g., the heating sources 310 described above) or from elsewhere within the environment of the ICE fabrication system 700, as described above in connection with FIGS. 3C and 5C. The light collected by the detector OD, including the modulated light 776 and the noise light 382, 384 or 386, is converted into detector signal 712. In this manner, the detector signal 712 includes a modulation having the timing 765 and an amplitude proportional to the attenuation of the instance 776 of the probe-light transmitted through the witness sample 309.

The time-gated detection module 760 is time-gated based on the timing 765 of the periodic motion of the witness sample 309 and the aperture 325, and receives as input the detector signal 712. For a current optical path difference $m\Delta z$, where m is one of $0, \pm 1, \pm 2, \ldots, \pm m_{max}$, intensity variation of the detector signal 712 can include the modulation with timing 765 of the modulated instance 776 of the probe-light, and intensity changes of the noise light 382, 384 or 386. A frequency of the timing 765 is selected to be different from frequencies and tones at which the intensity changes of the noise light 382, 384 and 386 can occur. Additionally, a width of the time-gate is chosen to be much smaller than (e.g., less than 10% of) a time scale over which the intensity changes of the noise light 382, 384 and 386 can occur. The frequency of the timing 765 can be of order 0.1 Hz, 1 Hz, or 10 Hz, for instance. Moreover, for the current optical path difference, the amplitude of the modulation of the modulated instance 776 of the probe-light is constant for constant emission of probe-light 370 by the source OS. As such, the output signal 715 of the time-gated detection module 760 (also referred to as the measurement signal 715) is a value of the amplitude of the modulation of the detector signal 712 having the timing 765. In some implementations, the measurement signal 715—for the current optical path difference $m\Delta z$ of the interferometer—represents an average over multiple modulation periods of the intensity of the current modulated instance 776 of the probe-light collected by the detector OD.

Figure 7D:
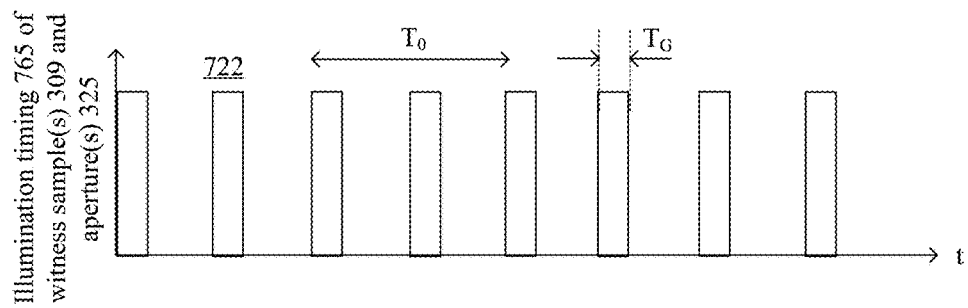

FIG. 7D shows a graph 722 that illustrates an example of an illumination timing 765 of the witness sample 309 and the aperture 325. As described above, the illumination timing 765 is used as a time-gate (the latter also being referenced as 765) by the time-gated detection module 760. Here, the time-gate 765 is a train of $K \geq 1$ pairs of ON/OFF pulses. A period $T_0$ of the time-gate 765 represents a time interval between two consecutive illuminations of the witness sample 309. The period $T_0$ can be of order 0.1 s, 1 s, or 10 s, for instance. A width $T_G$ of the pulses of the time-gate 765 is no longer than a time during which the instance 372 of the probe-light illuminates the witness sample 309 or the aperture 325. A value of the width $T_G$ of the time-gate 765 is a fraction of a value of the period $T_0$ of the time-gate 765, e.g., 20% or 10% of $T_0$. In this example (K=1), the time-gate 765 has a pair of pulses of width $T_G$ over a period $T_0$: one pulse corresponding to a portion of $T_0$ when the current instance of the probe-light is transmitted through the witness sample 309, and the other pulse corresponding to another portion of $T_0$ when the current instance of the probe-light passes through the aperture 325.

Figure 7E:
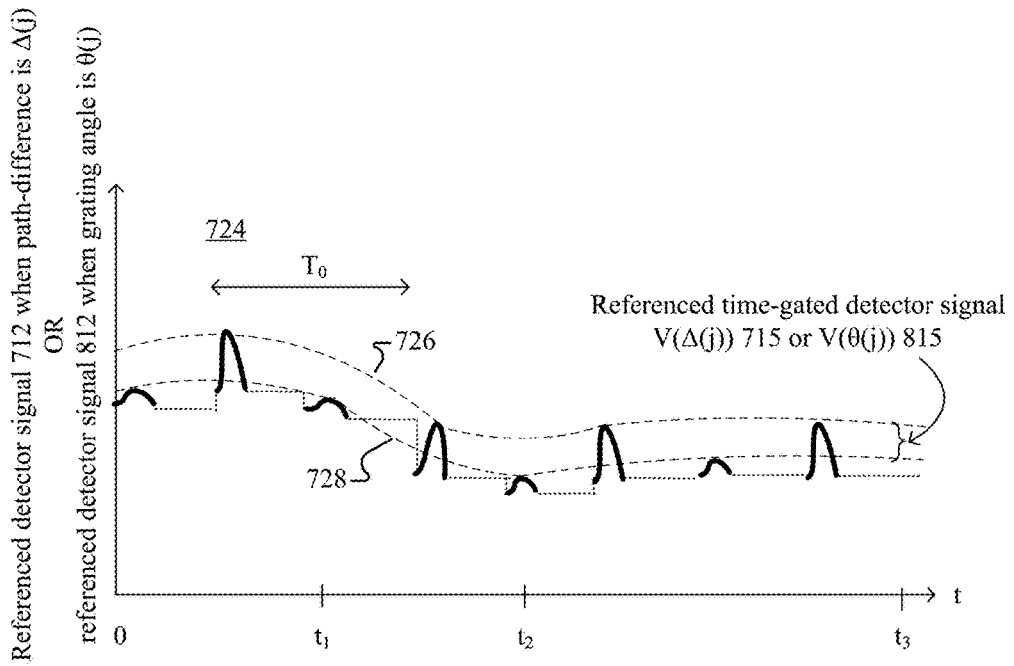

FIG. 7E shows a graph 724 that illustrates the detector signal 712 for a finite time interval $0\text{-}t_3$ (also referred to as the measurement time) over which the optical path difference $m\Delta z$ of the interferometer is maintained constant, where m is one of $0, \pm 1, \pm 2, \ldots, \pm m_{max}$. Note that the detector signal 712 (represented in continuous line) is limited to portions of the period $T_0$ when the time-gate 765 is open, or equivalently, when the current instance of the probe-light is transmitted through the witness sample 309 or passes through the aperture 325. In this example, the time-gated detection module 760 uses sample-and-hold during portions of the period $T_0$ when the time-gate 765 is closed. The detector signal 712 corresponding to such sample-and-hold values are represented in dotted-line. Additionally, the time-gated detection module 760 determines a maximum of the detector signal 712 for each of the pulses corresponding to times when the current instance of the probe-light passes through the aperture 325, and for each of the pulses corresponding to times when the current instance of the probe-light is transmitted through the witness sample 309. A first envelope 726 (represented in dashed line), generated by the time-gated detection module 760, fits a first set of the maxima of the detector signal 712 corresponding to the times when the current instance of the probe-light passes through the aperture 325. A second envelope 728 (also represented in dashed line), generated by the time-gated detection module 760, fits a second set of the maxima of the detector signal 712 corresponding to the times when the current instance of the probe-light is transmitted through the witness sample 309.

The measurement signal 715 output by the time-gated detection module 760—for the current optical path difference $m\Delta z$ of the interferometer—is the amplitude of the modulation of the detector signal 712 determined as the difference between the first 726 and second 728 envelopes. Hence, the measurement signal 715 is a measure of the amplitude of the modulation having the timing 765 of the current modulated instance of the probe-light collected by the detector OD. Although in the example illustrated in FIG. 7E a level of contributions from noise light 382, 384 or 386 remains around a first level before $t_1$, decreases to a lower, second level between $t_1$ and $t_2$, and increases to a different, third level after $t_2$, the amplitude of the modulation of the current modulated instance of the probe-light collected by the detector OD remains relatively constant over the entire measurement interval $0\text{-}t_3$, for the current optical path difference $m\Delta z$ of the interferometer. As such, the measurement signal $V(m\Delta z)$ 715 for the current optical path difference $m\Delta z$ of the interferometer—which is proportional to the amplitude of the modulation of the detector signal 712—is approximately constant over the measurement time interval $0$-$t_3$.

To obtain a new measurement signal $V((m+1)\Delta z)$ 715 for a subsequent optical path difference $(m+1)\Delta z$ of the interferometer, the second mirror 366 of the interferometer is translated on the translation stage 368 to a subsequent location $z_0+(m+1)\Delta z$ to change the optical path difference of the interferometer by $\Delta z$ relative to previous optical path difference $m\Delta z$ maintained during the previous measurement point. The new optical path difference $(m+1)\Delta z$ corresponds to a new instance 372 of the probe-light output by the interferometer that is spectrally different from the instance used to take the previous measurement point. The new instance 372 of the probe-light alternately passes through the aperture 325 and through the witness sample 309 and forms a new modulated instance 776 of the probe-light that has a modulation having the same timing 765 but different amplitude relative to the modulation of the modulated instance used to take the previous measurement point. As such, the new modulated instance 776 of the probe-light is collected with the detector OD, along with the noise light 382, 384 or 386, and converted into a new detector signal 712 corresponding to the new optical path difference $(m+1)\Delta z$ of the interferometer. The new measurement signal $V((m+1)\Delta z)$ 715 for the current optical path difference $(m+1)\Delta z$ of the interferometer is the output of the time-gated detection module 760, time-gated by the time-gate 765 shown in FIG. 7D, and is proportional to the amplitude of the modulation of the detector signal 712 over the measurement time interval $0$-$t_3$.

Using the above step-scan mode, the computer system 305 records a set of values $\{V(-m_{max}\Delta z), \ldots, V(-2\Delta z), V(-\Delta z), V(0), V(+\Delta z), V(+2\Delta z), \ldots, V(+m_{max}\Delta z)\}$ of the measurement signal 715 output by the spectrometer 304 to represent amplitudes of the modulation of the modulated instances 776-$m$ of the probe-light collected by the detector OD, for the corresponding optical path differences $\{-m_{max}\Delta z, \ldots, -2\Delta z, -\Delta z, 0, +\Delta z, +2\Delta z, \ldots, +m_{max}\Delta z\}$ of the interferometer. FIG. 3F shows a graph 324 in which the recorded set of values $\{V(m\Delta z), m=0, \pm 1, \pm 2, \ldots, \pm m_{max}\}$ is represented as open circles as a function of optical path difference (using normalized units for the optical path difference, $z/\Delta z$.) The computer system 305 fits the set of values represented in graph 324 to obtain, represented in solid line, the amplitude $V(z)$ of the modulation of the modulated instances 776 of the probe-light collected by the detector OD as a function of optical path difference of the interferometer. For example, the fit $V(z)$ is obtained by interpolating the recorded finite set of values $\{V(-m_{max}\Delta z), \ldots, V(-2\Delta z), V(-\Delta z), V(0), V(+\Delta z), V(+2\Delta z), \ldots, V(+m_{max}\Delta z)\}$ for optical path differences between $[-m_{max}\Delta z, +m_{max}\Delta z]$, and extrapolating the recorded values for optical path differences $z<-m_{max}\Delta z$, and $z>+m_{max}\Delta z$.

The computer system 305 can Fourier transform the obtained fit $V(z)$ to generate, in k-space (where k is the wave-number), a spectrum $B(k)$ for probe-light—with wavelengths in the measurement spectral range $[\lambda_{min}, \lambda_{max}]$—transmitted through the witness sample 309. FIG. 3G shows a graph 326 in which the generated spectrum $B(k)$ is represented, in solid line, only between a minimum wave-number $k_{min}=2\pi/\lambda_{max}$ and a maximum wave-number $k_{max}=2\pi/\lambda_{min}$ corresponding to respective maximum and minimum bounds of the measurement spectral range $[\lambda_{min}, \lambda_{max}]$. The generated spectrum $B(k)$ can also be expressed as a function of wavelength to obtain the spectrum $S(\lambda;j)$ of the probe-light transmitted through the formed layers $L(1), \ldots, L(j)$ of the witness sample 309.

Additionally, the computer system 305 can use the obtained spectrum $S(\lambda;j)$, over the wavelength range from $\lambda_{min}$ to $\lambda_{max}$, along with Fresnel's equations for propagating the probe-light through the formed layers to determine the complex refractive indices and thicknesses of each of the formed layers: $n^*_{Si}$, $n^*_{SiO2}$, $t'(1), t'(2), \ldots, t'(j-1), t'(j)$.

The in-situ spectroscopies described above in connection with FIGS. 7A-7B use time-gated detection to measure amplitudes of modulation imparted to spectrally different instances 372 of probe-light, such that, for each instance of the probe-light, a modulation is imparted by alternately passing the instance of the probe-light through an aperture 325 or through a witness sample 309. Here, the spectrally different instances 372 of probe-light are provided using an interferometer operated in step-scan mode. Other ways for providing the spectrally different instances 372 of probe-light are described below.

(3.4) System for ICE Fabrication Equipped with a Monochromator-Based Spectrometer Operated in Step-Scan Mode in Combination with Time-Gated Detection Technologies for in-situ monitoring of ICE fabrication using spectra of current instances of ICEs being fabricated are described below, such that the spectra are generated from results of step-scan spectroscopy performed with a monochromator-based spectrometer in combination with time-gated detection.

Figure 8A:
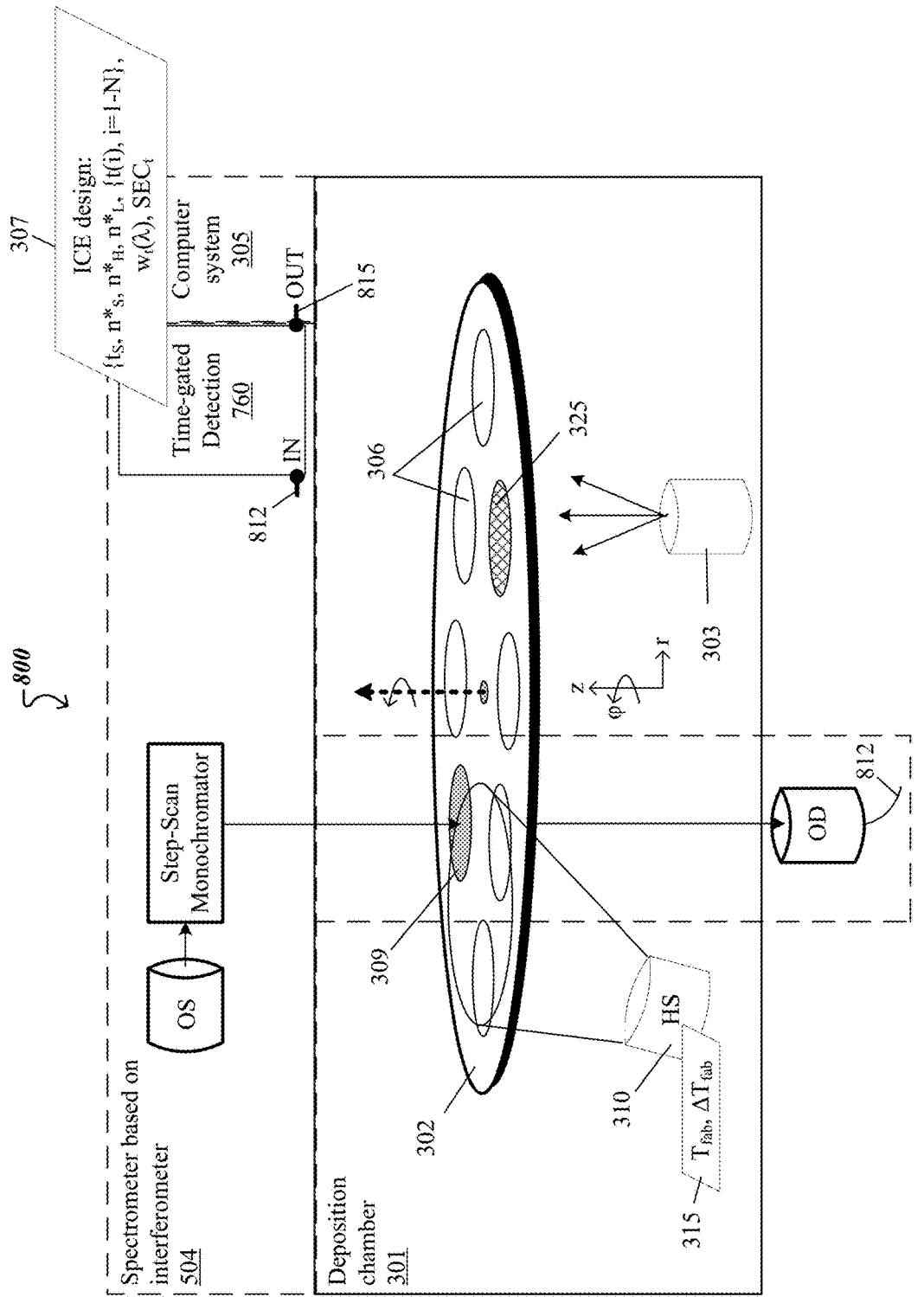
FIGS. 8A-8B show aspects of another system for fabricating ICEs that uses an in-situ monochromator-based spectrometer operated in step-scan mode—to periodically illuminate witness samples with un-modulated probe-light—in combination with the time-gated detection module—that detects the modulation of the probe-light that interacts with the witness samples, the modulation being caused by the periodic illumination—to monitor fabrication of the ICEs.

FIG. 8A shows an example of an ICE fabrication system 800. The ICE fabrication system 800 includes a deposition chamber 301 to fabricate one or more ICEs 306, a spectrometer 504 to acquire spectra of probe-light that interacted with formed layers of the ICEs while the ICEs are being fabricated, and a computer system 305 to control the fabrication of the one or more ICEs based at least in part on the acquired spectra.

The deposition chamber 301 includes one or more deposition sources 303 to provide materials with a low complex index of refraction $n^*_L$ and a high complex index of refraction $n^*_H$ used to form layers of the ICEs 306. Substrates on which layers of the ICEs 306 will be deposited are placed on a substrate support 302, such that the ICEs 306 are within the field of view of the deposition source(s) 303. The substrates have a thickness $t_S$ and a complex refraction index $n^*_S$ specified by a target ICE design 307, e.g., ICE design 145 or 245. The substrate support 302 is periodically moved with respect to the deposition source 303 (e.g., rotated along an azimuthal direction "$\phi$" about an axis laterally offset from the deposition source(s) 303 that passes through the center of the substrate support 302) to obtain reproducibly uniform layer deposition of the ICEs 306 within a batch. A heating source 310 provides heat to the current instances of the ICEs 306 distributed on the substrate support 302 to maintain their temperature within a target fabrication temperature range $\Delta T_{fab}$ around a target fabrication temperature $T_{fab}$. A process parameter 315 that includes the target fabrication temperature $T_{fab}$ and the target fabrication temperature range $\Delta T_{fab}$ is accessed by the computer system 305 and used to control the temperature of current instances of ICEs 306 during fabrication of ICEs associated with the ICE design 307.

As described above in connection with FIG. 5A, power provided to the source(s) 303, its(their) arrangement relative to the one or more substrate supports 302, etc., are used to control deposition rate(s) R of the source(s) 303. The actual complex refractive indices and thicknesses of the deposited layers L(1), . . . , L(j−1), L(j) can be determined when the deposition of the current layer L(j) is interrupted, e.g., with 10% left of the duration T(j), or when the deposition is completed at the end of the duration T(j). The complex refractive indices and thicknesses of the formed layers are determined in near real-time from a spectrum S($\lambda$;j) of probe-light that interacted with the formed layers L(1), . . . , L(j−1), L(j) acquired by the spectrometer 504.

The spectrometer 504 includes an optical source (OS) to emit probe-light having a wavelength range from $\lambda_{min}$ to $\lambda_{max}$, and a monochromator to receive the probe-light and to provide spectrally different instances of the probe-light corresponding to different relative orientations of a wavelength selector and an exit slit of the monochromator. Here, the monochromator is operated in step-scan mode, such that each of the instances of the probe-light is provided for a finite (non-zero) time interval. In this manner, the spectrometer 504 provides un-modulated instances of the probe-light—through an entry port associated with the spectrometer 504—into the deposition chamber 301 to illuminate a witness sample 309 supported by the substrate support 302. In the example illustrated in FIG. 8A, like in FIG. 7A, the periodic motion of the substrate support 302, and thus, of the witness sample 309, is maintained while the spectrometer 304 acquires a spectrum S($\lambda$;j). Also in analogy with FIG. 7A, at least one aperture 325 is disposed on the support substrate 302, spaced apart from the witness sample 309. In this manner, a current instance of the probe-light provided by the spectrometer 504 into the deposition chamber 301 alternately illuminates the aperture 325 and the witness sample 309. As such, a modulation is imparted to the current instance of the probe-light that propagates downstream from the substrate support 302. Timing of the modulation is based on the periodic motion of the aperture 325 and witness sample 309, and amplitude of the modulation is proportional to attenuation of the current instance of the probe-light transmitted through the witness sample 309. Each of the instances of the probe-light alternately passed through the aperture 325 and transmitted through the witness sample 309 is output from the deposition chamber 301 through an exit port associated with the spectrometer 504.

Further, the spectrometer 504 includes an optical detector (OD) to collect light that exits the deposition chamber through the exit port. The collected light includes the current instance of the probe-light alternately passed through the aperture 325 and transmitted through the witness sample 309, and light emitted by various noise sources, e.g., the heat source(s) 310, from the deposition chamber 310 or elsewhere in the environment of the ICE fabrication system 800. The detector OD converts the collected light to a detector signal 812. Additionally, the spectrometer 504 includes a time-gated detection module 760—that uses timing of the periodic motion of the aperture 325 and the witness sample 309—to gate (or limit) the detector signal 812. For instance, the time-gated detection module 760 limits the detector signal 812 to portions of the period of the periodic motion of the aperture 325 and the witness sample 309 when the current instance of the probe-light alternately illuminates the moving aperture 325 and the moving witness sample 309. Once the detector signal 812 is time-gated by the time-gated detection module 760 in accordance with the timing of the periodic motion of the aperture 325 and the witness sample 309, the time-gated detector signal is processed by the time-gated detection module 760 to output a measurement signal 815. Examples of types of processing performed by the time-gated detection module 760 on the time-gated detector signal are described above in connection with FIG. 7A. Moreover, the measurement signal 815 output by the time-gated detection module 760 is proportional to the amplitude of the modulation of the current instance of the probe-light collected by the detector OD. In this manner, the measurement signal 815 represents the attenuation of the current instance of the probe-light due to transmission through the witness sample 309.

The computer system 305 uses a set of values of the measurement signal 815 corresponding to the different spectral instances of the probe-light to generate a spectrum S($\lambda$;j) of probe-light transmitted through the formed layers L(1), . . . , L(j−1), L(j) of the witness sample 309. The generated spectrum S($\lambda$;j), over the wavelength range from $\lambda_{min}$ to $\lambda_{max}$, can be used by the computer system 305 to determine the complex refractive indices and thicknesses of each of the formed layers in the stack: $n^{*'}_{Si}$, $n^{*'}_{SiO2}$, t'(1), t'(2), . . . , t'(j−1), t'(j). The computer system 305 makes this determination by solving Fresnel's equations for propagating the interacted probe-light through the formed layers in the stack.

Various components of the spectrometer 504 and their corresponding functions are now described in detail.

Figure 8B:
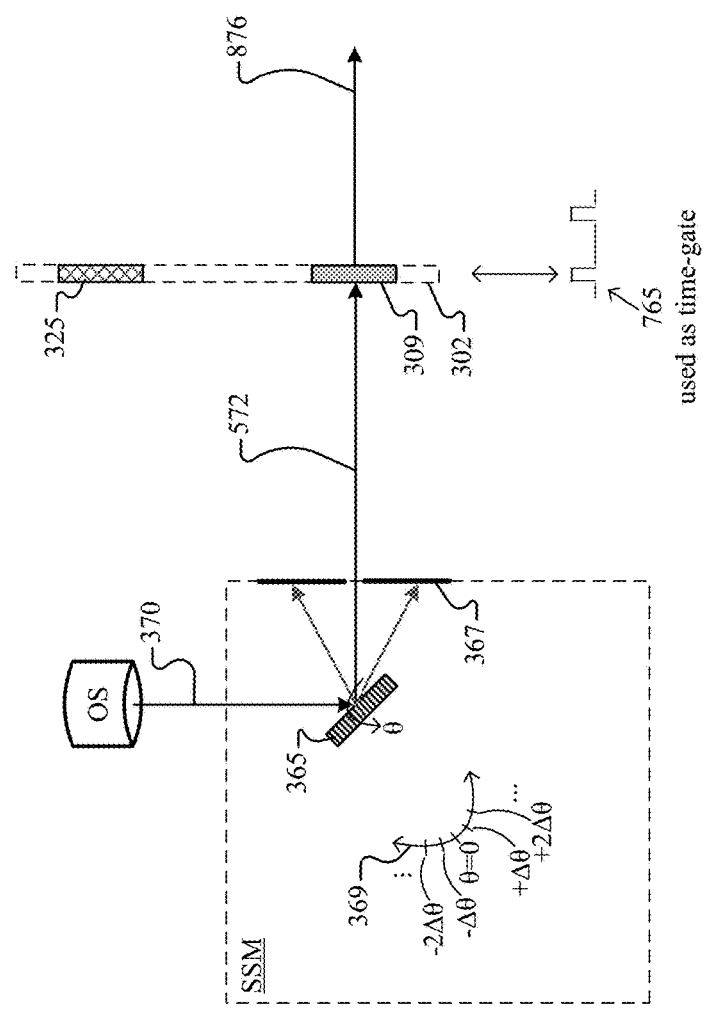

FIG. 8B shows a portion of the optical path of the spectrometer 504 upstream relative to the witness sample 309. Note that the portion illustrated in FIG. 8B represents a corresponding portion of FIG. 8A. The source OS and the monochromator of the spectrometer 504 have been described in detail in connection with FIG. 5A. A plurality of spectrally-different instances 572-*m* of the probe-light corresponding to a plurality of relative angular orientations ±m$\Delta\theta$ between the diffractive element 365 and the exit slit 367 for m=0, ±1, . . . , ±$m_{max}$, can be provided by discretely scanning, along the rotation stage 369, the relative angle $\Delta\theta$ between the diffractive element 365 and the exit slit 367. FIGS. 8B and 7C show that each instance 572 of the probe-light is directed into the deposition chamber 301 through an input port associated with the spectrometer 304 (not shown in FIGS. 8B and 7C) to alternately illuminate the witness sample 309 supported by and the aperture 325 of the substrate support 302. In this embodiment, the substrate support 302 is periodically moved (e.g., rotated about an axis through the center of the substrate support 302), such that each instance 572 of the probe-light alternately illuminates the witness sample 309 and the aperture 325 based on a timing 765. In this manner, a modulation—having the timing 765 and an amplitude that represents attenuation of each instance 572 of the probe-light transmitted through the witness sample 309—is imparted to the instance 572 of the probe-light that propagates downstream relative to the substrate support 302 to form a modulated instance 876 of the probe-light. Each modulated instance 876 of the probe-light is directed outside the deposition chamber 301 through an exit port associated with the spectrometer 304 (not shown in FIGS. 8B and 7C) to be collected by the detector OD.

FIG. 7C shows an optical path of the spectrometer 504 downstream relative to the witness sample 309. Note that the portion illustrated in FIG. 7C represents a corresponding portion of FIG. 8A. In addition to the modulated instance 876 of the probe-light, the detector OD collects light 382, 384 or 386 emitted by noise sources within the deposition chamber (e.g., the heating sources 310 described above) or from elsewhere within the environment of the ICE fabrication system 800, as described above in connection with FIGS. 3C and 5C. The light collected by the detector OD, including the modulated light 876 and the noise light 382, 384 or 386, is converted into detector signal 812. In this manner, the detector signal 812 includes a modulation having the timing 765 and an amplitude proportional to the attenuation of the instance 572 of the probe-light transmitted through the witness sample 309.

The time-gated detection module 760 is time-gated based on the timing 765 of the periodic motion of the witness sample 309 and the aperture 325, and receives as input the detector signal 812. For a current relative orientation mΔθ between the diffractive element 365 and the exit slit 367, where m is one of 0, ±1, ±2, . . . , ±$m_{max}$, intensity variation of the detector signal 812 can include the modulation with timing 765 of the modulated instance 876 of the probe-light, and intensity changes of the noise light 382, 384 or 386. Moreover, for the current relative orientation between the diffractive element 365 and the exit slit 367, the amplitude of the modulation of the modulated instance 876 of the probe-light is constant for constant emission of probe-light 370 by the source OS. As such, the output signal 815 of the time-gated detection module 760 (also referred to as the measurement signal 815) is a value of the amplitude of the modulation of the detector signal 812 having the timing 765. In some implementations, the measurement signal 815—for the current relative orientation mΔθ between the diffractive element 365 and the exit slit 367—represents an average over multiple modulation periods of the intensity of the current modulated instance 876 of the probe-light collected by the detector OD.

FIG. 7D shows a graph 722 that illustrates an example of an illumination timing 765 of the witness sample 309 and the aperture 325. As described above, the illumination timing 765 is used as a time-gate by the time-gated detection module 760. Here, the time-gate 765 is a train of K≥1 pairs of ON/OFF pulses. A period $T_0$ of the time-gate 765 represents a time interval between two consecutive illuminations of the witness sample 309. A width $T_G$ of the pulses of the time-gate 765 is no longer than a time during which the instance 572 of the probe-light illuminates the witness sample 309 or the aperture 325. In this example, the time-gate 765 has a pair of pulses of width $T_G$ over a period $T_0$: one pulse corresponding to a portion of $T_0$ when the current instance of the probe-light is transmitted through the witness sample 309, and the other pulse corresponding to another portion of $T_0$ when the current instance of the probe-light passes through the aperture 325.

FIG. 7E shows a graph 724 that illustrates the detector signal 812 for the measurement time 0-$t_3$ over which the relative orientation mΔθ between the diffractive element 365 and the exit slit 367 is maintained constant, where m is one of 0, ±1, ±2, . . . , *$m_{max}$. Note that the detector signal 812 (represented in continuous line) is limited to portions of the period $T_0$ when the time-gate 765 is open, or equivalently, when the current instance of the probe-light transmits through the witness sample 309 or passes through the aperture 325. In this example, the time-gated detection module 760 determines a maximum of the detector signal 812 for each of the pulses corresponding to times when the current instance of the probe-light passes through the aperture 325, and for each of the pulses corresponding to times when the current instance of the probe-light is transmitted through the witness sample 309. A first envelope 726 (represented in dashed line), generated by the time-gated detection module 760, fits a first set of the maxima of the detector signal 812 corresponding to the times when the current instance of the probe-light passes through the aperture 325. A second envelope 728 (also represented in dashed line), generated by the time-gated detection module 760, fits a second set of the maxima of the detector signal 812 corresponding to the times when the current instance of the probe-light is transmitted through the witness sample 309.

The measurement signal 815 output by the time-gated detection module 760—for the current relative orientation mΔθ between the diffractive element 365 and the exit slit 367—is the amplitude of the modulation of the detector signal 812 determined as the difference between the first 726 and second 728 envelopes. Hence, the measurement signal 815 is a measure of the amplitude of the modulation having the timing 765 of the current modulated instance of the probe-light collected by the detector OD. Although in the example illustrated in FIG. 7E a level of contributions from noise light 382, 384 or 386 remains around a first level before $t_1$, decreases to a lower, second level between $t_1$ and $t_2$, and increases to a different, third level after $t_2$, the amplitude of the modulation of the current modulated instance of the probe-light collected by the detector OD remains relatively constant over the entire measurement interval 0-$t_3$, for the current relative orientation mΔθ between the diffractive element 365 and the exit slit 367. As such, the measurement signal V(mΔθ) 815 for the current relative orientation mΔθ between the diffractive element 365 and the exit slit 367—which is proportional to the amplitude of the modulation of the detector signal 812—is approximately constant over the measurement time interval 0-$t_3$.

To obtain a new measurement signal V((m+1)Δθ) 815 for a subsequent relative orientation mΔθ between the diffractive element 365 and the exit slit 367, the diffractive element 365 of the monochromator is rotated on the rotation stage 369 to a subsequent angular location $θ_0$+(m+1)Δθ to change the relative orientation between the diffractive element 365 and the exit slit 367 by Δθ relative to previous relative orientation mΔθ maintained during the previous measurement point. The new relative orientation mΔθ corresponds to a new instance 572 of the probe-light output by the monochromator that is spectrally different from the instance used to take the previous measurement point. The new instance 572 of the probe-light alternately passes through the aperture 325 and through the witness sample 309 and forms a new modulated instance 876 of the probe-light that has a modulation having the same timing 765 but different amplitude relative to the modulation of the modulated instance used to take the previous measurement point. As such, the new modulated instance 876 of the probe-light is collected with the detector OD, along with the noise light 382, 384 or 386, and converted into a new detector signal 812 corresponding to the new relative orientation (m+1)Δθ between the diffractive element 365 and the exit slit 367. The new measurement signal V((m+1)Δθ) 815 for the current relative orientation (m+1)Δθ between the diffractive element 365 and the exit slit 367 is the output of the time-gated detection module 760, time-gated by the time-gate 765 shown in FIG. 7D, and is proportional to the amplitude of the modulation of the detector signal 812 over the measurement time interval 0-$t_3$.

Using the above step-scan mode, the computer system 305 records a set of values {V(-$m_{max}$Δθ), . . . , V(-2Δθ), V(-Δθ), V(0), V(+Δθ), V(+2Δθ), V(+$m_{max}$Δθ)} of the measurement signal 815 output by the spectrometer 504 to represent amplitudes of the modulation of the modulated instances 876-m of the probe-light collected by the detector OD, for the corresponding relative orientations {-$m_{max}$Δθ, . . . , -2Δθ, -Δθ, 0, +Δθ, +2Δθ, . . . , +$m_{max}$Δθ} between the diffractive element 365 and the exit slit 367. FIG. 5C shows a graph 524 in which the recorded set of values {V($θ_{min}$), . . . , V(-2Δθ), V(-Δθ), V(0), V(+Δθ), V(+2Δθ), . . . , V($θ_{max}$)} is represented as filled circles as a function of relative orientation between the diffractive element 365 and the exit slit 367 (using normalized units for the relative orientation, $\theta/\Delta\theta$.) The computer system 305 fits the set of values represented in graph 524 to obtain, represented in solid line, the amplitude $V(\theta)$ of the modulation of the modulated instances 876 of the probe-light collected by the detector OD as a function of relative orientation between the diffractive element 365 and the exit slit 367. For example, the fit $V(\theta)$ is obtained by interpolating the recorded finite set of values $\{V(\theta_{min}), \ldots, V(-2\Delta\theta), V(-\Delta\theta), V(0), V(+\Delta\theta), V(+2\Delta\theta), \ldots, V(\theta_{max})\}$ for relative orientations between $[\theta_{min}, \theta_{max}]$, and extrapolating the recorded values for relative orientations $\theta<\theta_{min}$, and $\theta>\theta_{max}$.

The computer system 305 can correlate angles of the angular range $[\theta_{min}, \theta_{max}]$ of the described step-scan with wavelengths the measurement spectral range $[\lambda_{min}, \lambda_{max}]$, and further appropriately scale, normalize, etc. the obtained fit $V(\theta)$ to generate a spectrum $S(\lambda;j)$ of probe-light transmitted through the formed layers $L(1), \ldots, L(j)$ of the witness sample 309. FIG. 5D shows a graph 526 in which the generated spectrum $S(\lambda;j)$ is represented in solid line over the measurement spectral range $[\lambda_{min}, \lambda_{max}]$. As noted above, the computer system 305 can use the generated spectrum $S(\lambda;j)$—illustrated in FIG. 5D—along with Fresnel's equations for propagating the probe-light through the formed layers to determine the complex refractive indices and thicknesses of each of the formed layers: $n^{*'}_{Si}$, $n^{*'}_{SiO2}$, $t'(1), t'(2), \ldots, t'(j-1), t'(j)$.

Referring now to any of FIG. 3A, 5A, 7A or 8A, the computer system 305 includes one or more hardware processors and memory. The memory encodes instructions that, when executed by the one or more hardware processors, cause any of the fabrication systems 300, 500, 700 or 800 to perform processes for fabricating the ICEs 306. Examples of such processes are described below in connection with FIGS. 9A-9C. The computer system 305 also includes or is communicatively coupled with a storage system that stores one or more ICE designs 307, aspects of the deposition capability, and other information. The stored ICE designs can be organized in design libraries by a variety of criteria, such as ICE designs used to fabricate ICEs for determining values of a particular characteristic over many substances (e.g. the GOR ratio in crude oil, refined hydrocarbons, mud, etc.), or ICE designs used to fabricate ICEs for determining values of many properties of a given substance (e.g., viscosity, GOR, density, etc., of crude oil.) In this manner, upon receipt of an instruction to fabricate an ICE for measuring a given characteristic of a substance, the computer system 305 accesses such a design library and retrieves an appropriate ICE design 307 that is associated with the given characteristic of the substance.

The retrieved ICE design 307 includes specification of a substrate and a total number N of layers to be formed in the deposition chamber 301 on the substrate; specification of a complex refractive index $n^*_S$ of a material of the substrate, a high complex refractive index $n^*_H$ and a low complex refractive index $n^*_L$ of materials (e.g., Si and $SiO_2$) to form the N layers with adjacent layers having different complex refractive indices; and specification of target thicknesses $\{t_S, t(k), k=1-N\}$ of the substrate and the N layers. Implicitly or explicitly, the ICE design 307 also can include specification of a target optical spectrum $w_t(\lambda)$ associated with the given characteristic; and specification of a target $SEC_t$ representing expected performance of an ICE associated with the retrieved ICE design 307. The foregoing items of the retrieved ICE design 307 were determined, prior to fabricating the ICEs 306, in accordance with the ICE design process 200 described above in connection with FIG. 2. In some implementations, the ICE design 307 can include indication of maximum allowed $SEC_{max}$ caused by fabrication errors. Figures of merit other than the target $SEC_t$ can be included in the retrieved ICE design 307, e.g., SEP, the ICE sensitivity, etc.

The complex refractive indices and target thicknesses $\{t(k), k=1-N\}$ of the N layers, as specified by the retrieved ICE design 307, are used by the computer system 305, in conjunction with aspects of deposition capability of either of the ICE fab systems 300, 500, 700 or 800, to control deposition rate(s) of the deposition source(s) 303 and respective deposition times for forming layers of a plurality of ICEs. Here, the layers of the ICEs being formed are sequentially illuminated with instances of probe-light provided by the measurement system 304 associated with the fabrication systems 300 or 700, or alternatively by the measurement system 504 associated with the fabrication systems 500 or 800. Here, the instances of probe-light provided by each of the measurement systems 304 or 504 are spectrally different from each other within a measurement spectral range. As each of the measurement systems 304 and 504 are operated by the computer system 305 in step-scan mode, each of the instances of probe-light illuminates the formed ICE layers for a finite (non-zero) time interval. For each of the instances of probe-light, the measurement system detects a modulation of probe-light that interacts with (e.g., is transmitted through) the formed ICE layers. The computer system 305 generates a spectrum of the probe-light interacted with the formed ICE layers over the measurement spectral range from a set of values of the detected modulations corresponding to the instances of the probe-light. If necessary, the computer system 305 then instructs the ICE fabrication system 300, 500, 700 or 800 to adjust the forming of ICE layers remaining to be formed based on the generated spectrum.

Figure 9A:
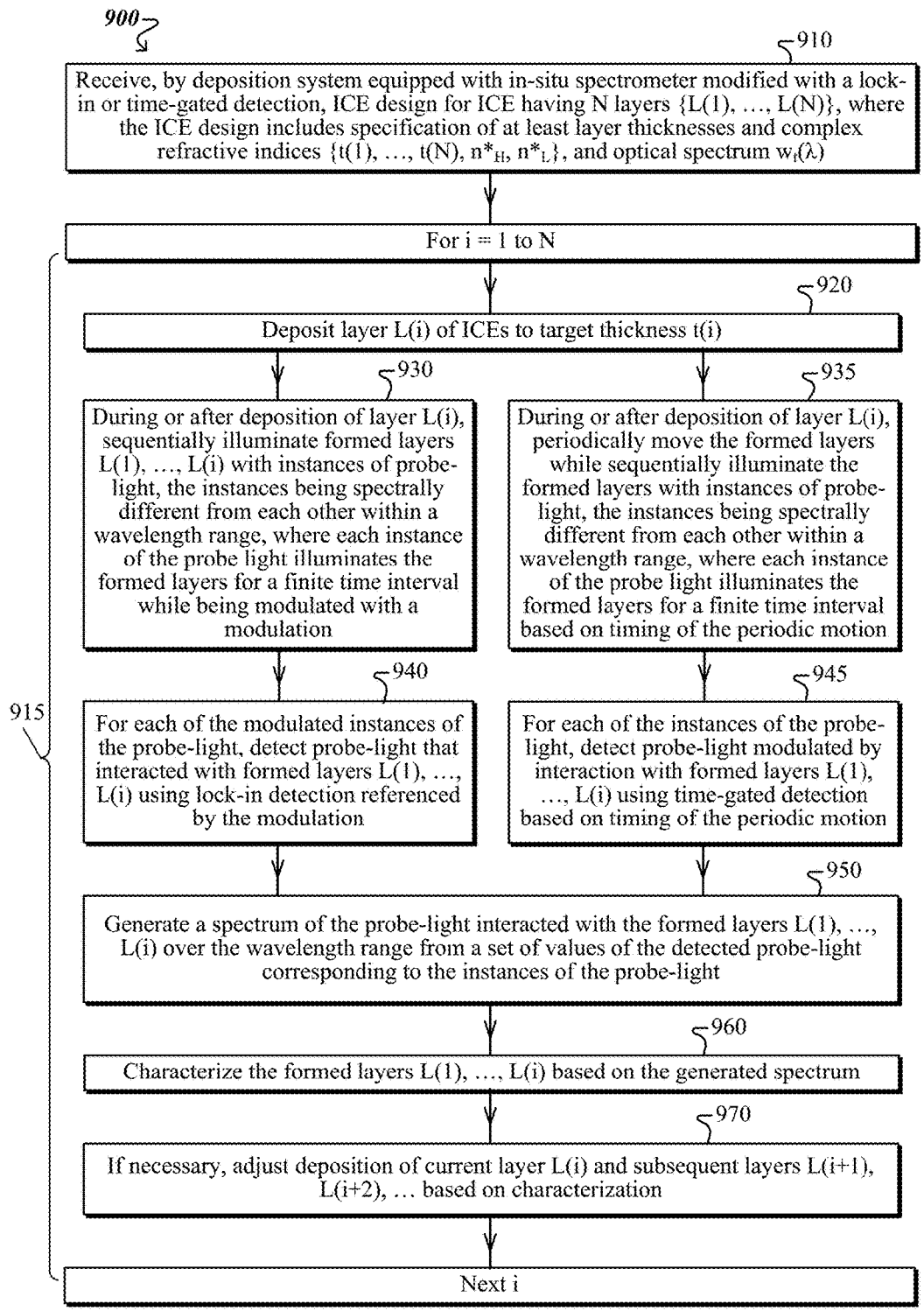
FIG. 9A is a flowchart of an ICE fabrication process that uses in-situ spectroscopy operated in step-scan mode in combination with lock-in or time-gated detection for generating spectra of ICEs being fabricated.

(3.5) Techniques for ICE Fabrication Assisted by In-Situ Monitoring Based on Step-Scan Spectroscopy in Combination with Detection Timed Based on Modulation of Probe-Light Interacted with ICEs being Fabricated FIG. 9A is a flow chart of an example of an ICE fabrication process 900 that uses step-scan spectroscopy in combination with lock-in or time-gated detection to generate a spectrum of ICEs being fabricated. The process 900 can be implemented in conjunction with either of ICE fabrication systems 300, 500, 700 or 800. In such a context, the process 900 can be implemented as instructions encoded in the memory of the computer system 305, such that execution of the instructions, by the one or more hardware processors of the computer system 305, causes the ICE fabrication system 300, 500, 700 or 800 to perform the following operations.

At 910, an ICE design is received. The received ICE design includes specification of a substrate and N layers $L(1), L(2), \ldots, L(N)$, each having a different complex refractive index from its adjacent layers, and specification of target complex refractive indices and thicknesses $t_S$, $t(1)$, $t(2), \ldots, t(N)$. In this manner, an ICE fabricated in accordance with the received ICE design selectively weights, when operated, light in at least a portion of a wavelength range by differing amounts. The differing amounts weighted over the wavelength range correspond to a target optical spectrum $w_t(\lambda)$ of the ICE and are related to a characteristic of a sample. For example, a design process for determining the specified (1) substrate and number N of layers of the ICE, each having a different complex refractive index from its adjacent layers, and (2) complex refractive indices and thicknesses of the substrate and the N layers that correspond to the target optical spectrum $w_t(\lambda)$ of the ICE is described above in connection with FIG. 2. In some implementations, the received ICE design also can include $SEC_t$ as an indication of a target performance of the ICE. The target performance represents an accuracy with which the ICE predicts, when operated, known values of the characteristic corresponding to validation spectra of the sample. Here, predicted values of the characteristic are obtained when the validation spectra weighted by the ICE are respectively integrated. In some implementations, the received ICE design also can include indication of maximum allowed $SEC_{max}$ caused by fabrication errors.

Loop 915 is used to fabricate one or more ICEs based on the received ICE design. Each iteration "i" of the loop 915 is used to form a layer L(i) of a total number N of layers. Here, the total number N of layers can be either specified in the received ICE design or updated during the ICE fabrication. Updates to the received ICE design are performed when necessary for preventing performance of the fabricated ICE to degrade under a threshold value.

At 920, the layer L(i) is formed to a target thickness t(i) while periodically moving the ICEs being fabricated relative to a deposition source. The target thickness t(i) of the layer L(i) can be specified by the received ICE design or updated based on optimization(s) carried out after forming previous one or more of the layers of the ICE. One or more of the ICEs being fabricated can be used as a witness sample.

In some implementations, the periodic motion of the witness sample (and of the ICEs being fabricated) is interrupted after completion of at least a sub-layer of the layer L(i). In this case, attenuation of probe-light interacted with the witness sample is measured at 930 and 940 using lock-in detection.

At 930, a witness sample—that includes formed layers L(1), . . . , L(i)—is sequentially illuminated with instances of probe-light, such that the witness sample is illuminated by a single instance of the probe-light at a time and it is at rest relative to a beam of the instance of the probe-light illuminating the witness sample. The instances of the probe-light, provided by either an interferometer or a monochromator, are spectrally different from each other. As the interferometer or monochromator are operated in step-scan mode to generate the instances of the probe-light, each instance of the probe light illuminates the witness sample for a finite time interval. Moreover, a modulation is imparted to the instances of the probe-light upstream relative to a point of incidence with the witness sample. In this manner, the witness sample is illuminated with modulated instances of the probe-light.

At 940, for each of the modulated instances of the probe-light, probe-light that interacted with the formed layers L(1), . . . , L(i) of the witness sample is detected using lock-in detection referenced by the modulation. Examples of such lock-in detection of the modulated instances of the probe light—provided either with a step-scan interferometer or with a step-scan monochromator—are described above in connection with FIG. 3C. An example of a modulation timing that is used as reference signal by the lock-in detection is described above in connection with FIG. 3D. Attenuation of each instance of the probe-light is proportional to a value of amplitude of the modulation of the instance of probe-light detected with the lock-in detection after interaction with the witness sample, as described above in connection with FIG. 3E. A set of values of the modulation amplitudes corresponding to the instances of probe-light interacted with the witness sample is recorded for use in generating a spectrum of the formed layers L(1), . . . , L(i) of the witness sample.

In other implementations, the periodic motion of the witness sample (and of the ICEs being fabricated) is maintained after completion of at least a sub-layer of the layer L(i). In this case, attenuation of the probe-light interacted with the witness sample is measured at 935 and 945 using time-gated detection.

At 935, a witness sample—that includes formed layers L(1), . . . , L(i)—is sequentially illuminated with instances of probe-light, such that the witness sample is illuminated by a single instance of the probe-light at a time and it is periodically moved relative to a beam of the instance of the probe-light illuminating the witness sample. The instances of the probe-light, provided by either an interferometer or a monochromator, are spectrally different from each other. As the interferometer or monochromator are operated in step-scan mode to generate the instances of the probe-light, each instance of the probe light illuminates the witness sample for a finite time interval. Here, a modulation is imparted to each instance of the probe-light by alternately transmitting the instance of the probe-light through the witness sample and passing the same by the witness sample. Attenuation of each instance of the probe-light is proportional to a value of amplitude of the modulation of the instance of probe-light generated as described above.

At 945, for each of the instances of the probe-light, probe-light modulated by interaction with the formed layers L(1), . . . , L(i) of the witness sample is detected using time-gated detection based on timing of the periodic motion. Examples of such time-gated detection of the instances of the probe light—provided either with a step-scan interferometer or with a step-scan monochromator—after being modulated by transmission through the witness sample are described above in connection with FIG. 7C. An example of a timing of the periodic motion that is used as time-gate by the time-gated detection is described above in connection with FIG. 7D. A value of amplitude of the modulation of the instance of probe-light is output by the time-gated detection, as described above in connection with FIG. 7E. A set of values of the amplitudes of the modulation imparted to the instances of probe-light by interaction with the witness sample is recorded for use in generating a spectrum of the formed layers L(1), . . . , L(i) of the witness sample.

At 950, a spectrum of the probe-light interacted with the formed layers L(1), . . . , L(i) of the witness sample is generated over the wavelength range from a set of values of the detected probe-light corresponding to the instances of the probe-light. The generated spectrum also is referred to as the spectrum of the formed layers. Here, the set of values was recorded either at 940 after using step-scan spectroscopy in combination with lock-in detection, or at 945 after using step-scan spectroscopy in combination with time-gated detection. In implementations where the instances of the probe-light—to which the recorded values correspond—were provided using an interferometer, the spectrum of the probe-light interacted with the witness sample is generated as described above in connection with FIGS. 3E-3F. In implementations where the instances of the probe-light—to which the recorded values correspond—were provided using a monochromator, the spectrum of the probe-light interacted with the witness sample is generated as described above in connection with FIGS. 5C-5D.

Aspects of the step-scan spectroscopy performed with an interferometer-based spectrometer are described below in connection with FIG. 9B, and aspects of the step-scan spectroscopy performed with a monochromator-based spectrometer are described below in connection with FIG. 9C.

Interferometer Based Step-Scan Spectroscopy

Figure 9B:
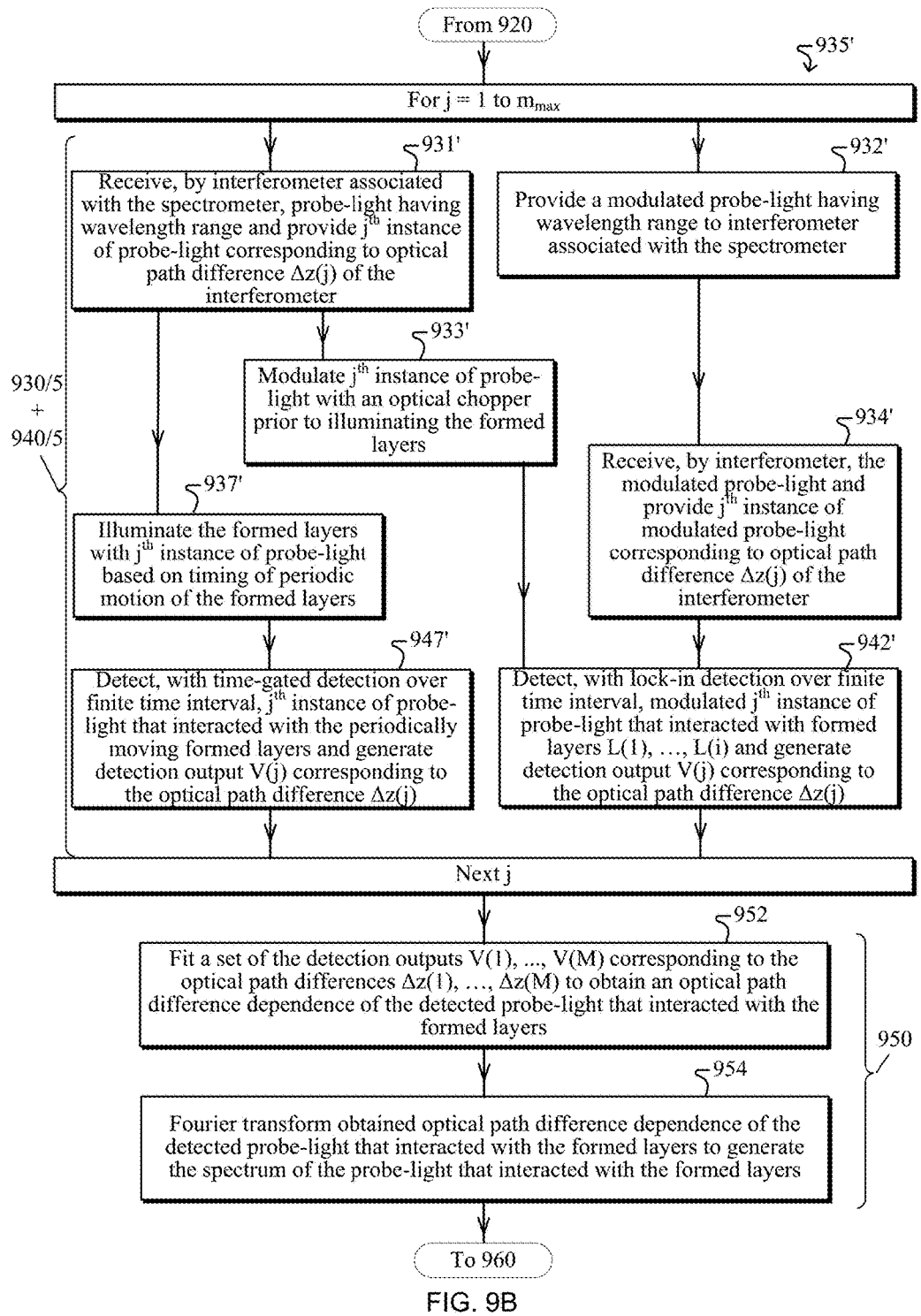
FIG. 9B shows aspects of the ICE fabrication process from FIG. 9A, where the in-situ spectroscopy operated in step-scan mode is performed with an interferometer-based spectrometer.

FIG. 9B is a flowchart of operations performed as part of either of the sequences {930, 940, 950} or {935, 945, 950} of the ICE fabrication process 900. The operations described in connection with FIG. 9B can be implemented in conjunction with either of the ICE fabrication systems 300 or 700, for instance.

A loop 935' is used to perform, after operation 920 of the ICE fabrication process 900, step-scan spectroscopy using an interferometer-based spectrometer. The loop 935' encompasses either of the sequences {930, 940} or {935, 945}.

In some implementations, the loop 935' (corresponding to the sequence {930, 940}) can be performed as a sequence of operations {931', 933', 942'}. Examples of such implementations are described above in connection with FIGS. 3B, 3C, 3D and 3E.

As part of the $j^{th}$ iteration of the loop 935', where j=1 to $m_{max} \geq 2$, at 931', probe-light having a wavelength range (e.g., the measurement spectral range $[\lambda_{min}, \lambda_{max}]$) is received by the spectrometer's interferometer. Additionally, a $j^{th}$ instance of the probe-light corresponding to an optical path difference $\Delta z(j)$ of the interferometer is provided by the interferometer. The provided $j^{th}$ instance of the probe-light includes wavelengths of the measurement spectral range $[\lambda_{min}, \lambda_{max}]$ that interfere constructively for the optical path difference $\Delta z(j)$, and excludes wavelengths of the measurement spectral range $[\lambda_{min}, \lambda_{max}]$ that interfere destructively for the optical path difference $\Delta z(j)$. In the example illustrated in FIG. 3B, the probe-light output by the source OS over the measurement spectral range $[\lambda_{min}, \lambda_{max}]$ is denoted 370, and the $j^{th}$ instance of the probe-light provided by the interferometer is denoted 372.

At 933', the $j^{th}$ instance of the probe-light is modulated with an optical chopper prior to illuminating the layers L(1), . . . , L(i) of the witness sample formed at 920. In the examples illustrated in FIGS. 3B-3C, the $j^{th}$ modulated instance of the probe-light is denoted 374.

At 942', the modulated $j^{th}$ instance of the probe-light that interacts with the formed layers L(1), . . . , L(i) of the witness sample is detected, over a finite time interval, using lock-in detection. An output V(j) of the lock-in detection is proportional to amplitude of the modulation of the detected modulated $j^{th}$ instance of the probe-light that interacts with the witness sample. In this manner, the output V(j) corresponds to the optical path difference $\Delta z(j)$. In the examples illustrated in FIGS. 3C-3E, the $j^{th}$ modulated instance of the probe-light that interacts with the witness sample is denoted 376; the detected modulated $j^{th}$ instance of the probe-light that interacts with the witness sample—which includes the modulation 345—is denoted 312; and the output V(j) corresponding to the optical path difference $\Delta z(j)$ is denoted 315.

In other implementations, the loop 935' (corresponding to the sequence {930, 940}) can be performed as a sequence of operations {932', 934', 942'}. Examples of such implementations are described above in connection with FIGS. 4, 3C, 3D and 3E.

At 932', a modulated probe-light having a wavelength range is provided to the spectrometer's interferometer. In the example illustrated in FIG. 4, the modulated probe-light output by the source OS over the measurement spectral range $[\lambda_{min}, \lambda_{max}]$ is denoted 371.

As part of the $j^{th}$ iteration of the loop 935', where j=1 to $m_{max} \geq 2$, at 934', the modulated probe-light is received by the interferometer. Additionally, a $j^{th}$ instance of the modulated probe-light corresponding to an optical path difference $\Delta z(j)$ of the interferometer is provided by the interferometer. As described above, the provided $j^{th}$ instance of the modulated probe-light includes wavelengths of the measurement spectral range $[\lambda_{min}, \lambda_{max}]$ that interfere constructively for the optical path difference $\Delta z(j)$, and excludes wavelengths of the measurement spectral range $[\lambda_{min}, \lambda_{max}]$ that interfere destructively for the optical path difference $\Delta z(j)$. In the example illustrated in FIG. 4, the $j^{th}$ instance of the modulated probe-light provided by the interferometer is denoted 374.

At 942', the $j^{th}$ instance of the modulated probe-light that interacts with the formed layers L(1), . . . , L(i) of the witness sample is detected, over a finite time interval, using lock-in detection. An output V(j) of the lock-in detection is proportional to amplitude of the modulation of the detected $j^{th}$ instance of the modulated probe-light that interacts with the witness sample. In this manner, the output V(j) corresponds to the optical path difference $\Delta z(j)$. In the examples illustrated in FIGS. 3C-3E, the $j^{th}$ instance of the modulated probe-light that interacts with the witness sample is denoted 376; the detected $j^{th}$ instance of the modulated probe-light that interacts with the witness sample—which includes the modulation 345—is denoted 312; and the output V(j) corresponding to the optical path difference $\Delta z(j)$ is denoted 315.

In some other implementations, the loop 935' (corresponding to the sequence {935, 945}) can be performed as a sequence of operations {931', 937', 947'}. Examples of such implementations are described above in connection with FIGS. 7B, 7C, 7D and 7E.

As part of the $j^{th}$ iteration of the loop 935', where j=1 to $m_{max} \geq 2$, at 931', probe-light having a wavelength range (e.g., the measurement spectral range $[\lambda_{min}, \lambda_{max}]$) is received by the spectrometer's interferometer. Additionally, a $j^{th}$ instance of the probe-light corresponding to an optical path difference $\Delta z(j)$ of the interferometer is provided by the interferometer. The provided $j^{th}$ instance of the probe-light includes wavelengths of the measurement spectral range $[\lambda_{min}, \lambda_{max}]$ that interfere constructively for the optical path difference $\Delta z(j)$, and excludes wavelengths of the measurement spectral range $[\lambda_{min}, \lambda_{max}]$ that interfere destructively for the optical path difference $\Delta z(j)$. In the examples illustrated in FIG. 7B, the probe-light output by the source OS over the measurement spectral range $[\lambda_{min}, \lambda_{max}]$ is denoted 370, and the $j^{th}$ instance of the probe-light provided by the interferometer is denoted 372.

At 937', a witness sample including the formed layers is illuminated with the $j^{th}$ instance of probe-light corresponding to the optical path difference $\Delta z(j)$ of the interferometer using the timing of the periodic motion of the witness sample. In this manner, a modulation is imparted to the $j^{th}$ instance of the probe-light by alternately transmitting the $j^{th}$ instance of the probe-light through the witness sample and passing the same by the witness sample. Attenuation of the $j^{th}$ instance of the probe-light is proportional to a value of amplitude of the modulation of the $j^{th}$ instance of probe-light generated as described above. In the examples illustrated in FIGS. 7B-7C, the modulated probe-light is denoted 776 and a timing of its modulation is denoted 765.

At 947', the $j^{th}$ instance of probe-light that interacts with the periodically moving formed layers is detected, over finite time interval, using time-gated detection. An output V(j) of the time-gated detection is proportional to amplitude of a modulation of the detected $j^{th}$ instance of the probe-light that interacts with the witness sample. In this manner, an output V(j) of the time-gated detection corresponds to the optical path difference $\Delta z(j)$. In the examples illustrated in FIGS. 7C-7E, the $j^{th}$ instance of the probe-light that interacts with the witness sample is denoted 776; the detected $j^{th}$ instance of the probe-light that interacts with the witness sample—which includes the modulation with timing 765—is denoted 712; and the output V(j) corresponding to the optical path difference $\Delta(j)$ is denoted 715.

In general, subsequent iterations of the loop 935' will generate outputs V(j+1), ..., V($m_{max}$) of the lock-in or time-gated detection corresponding to subsequent optical path differences $\Delta z(j+1), \ldots, \Delta z(m_{max})$. As the set of values {V(j), j=1–$m_{max}$} are being acquired, or when their acquisition is completed, the acquired values {V(j), j=1–$m_{max}$} can be represented in plot 324 illustrated in FIG. 3F. Once the entire set of values {V(1), ..., V($m_{max}$)} corresponding to all available optical path differences $\Delta z(1), \ldots, \Delta z(m_{max})$ is recorded, the operations of 950 of the process 900 can be performed.

At 952, a set of the detection outputs {V(1), ..., V($m_{max}$)} corresponding to the optical path differences $\Delta z(1), \ldots, \Delta z(m_{max})$ is fitted to obtain an optical path difference dependence of the detected probe-light that interacts with the formed layers of the ICE. In the example illustrated in FIG. 3F, the obtained optical path difference dependence of the detected probe-light that interacts with the formed layers is denoted V(z), where "z" is the optical path difference.

At 954, the obtained optical path difference dependence of the detected probe-light that interacts with the formed layers is Fourier transformed to generate the spectrum of the probe-light that interacts with the formed layers. In the example illustrated in FIG. 3G, as a first step of the Fourier transformation, a spectrum B(k) of the formed layers is generated in wave-number space. A wave-number is defined as $k=2\pi/\lambda$. As a subsequent step, the spectrum B(k) can be transformed into the desired spectrum S($\lambda$;i) of the formed layers L(1), ..., L(i) of the witness sample in wavelength space.

The spectrum generated at 954—as a result of performing the step-scan spectroscopy that uses an interferometer-based spectrometer—is provided to the process 900 as input to one or more operations to be carried out at 960. Prior to describing the operations carried out at 960, generating the spectrum of the formed layers of the witness sample as a result of step-scan spectroscopy that uses a monochromator-based spectrometer is described below.

Monochromator Based Step-Scan Spectroscopy

Figure 9C:
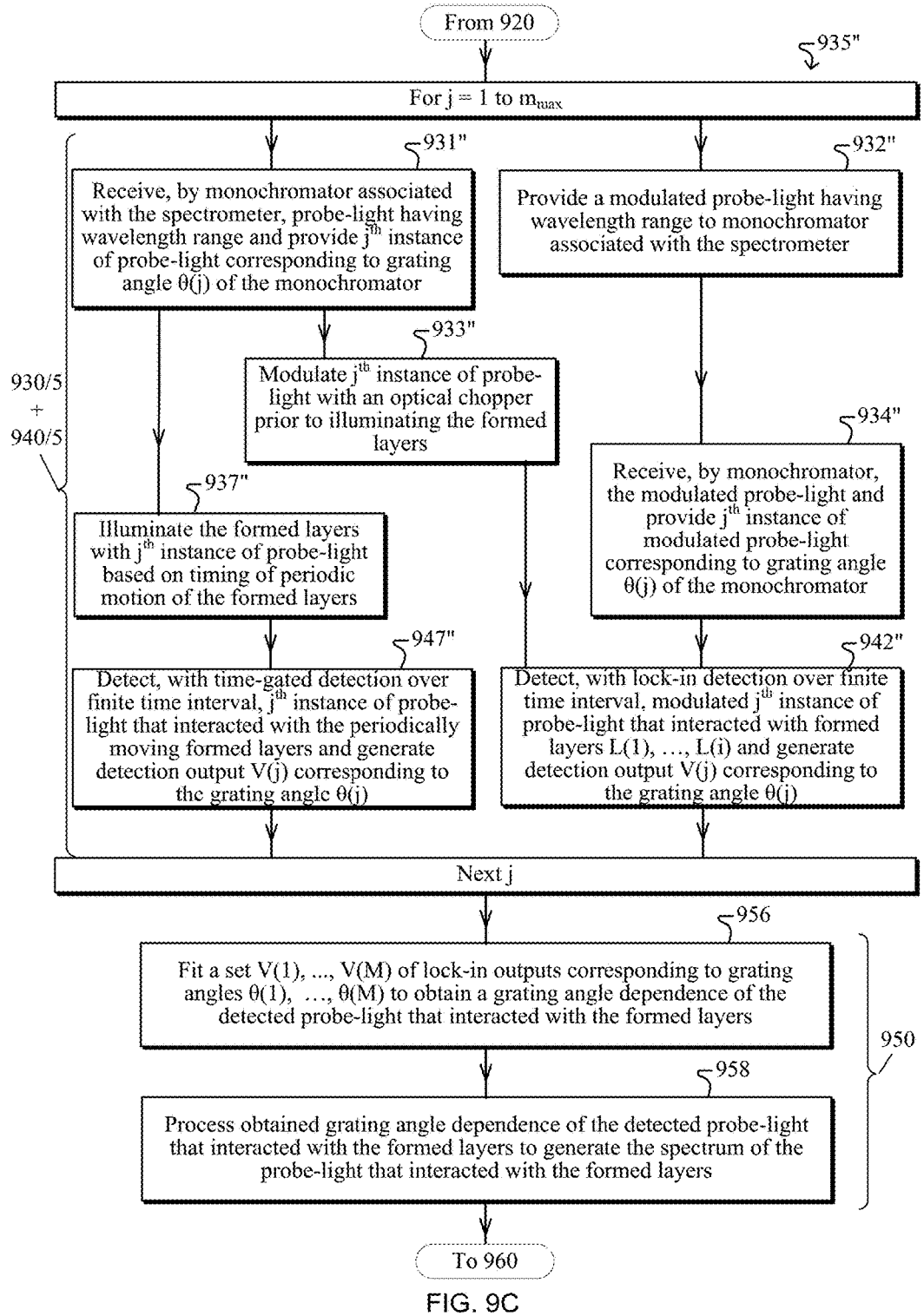
FIG. 9C shows aspects of the ICE fabrication process from FIG. 9A, where the in-situ spectroscopy operated in step-scan mode is performed with a monochromator-based spectrometer.

FIG. 9C is a flowchart of operations performed as part of either of the sequences {930, 940, 950} or {935, 945, 950} of the ICE fabrication process 900. The operations described in connection with FIG. 9C can be implemented in conjunction with either of the ICE fabrication systems 500 or 800, for instance.

A loop 935" is used to perform, after operation 920 of the ICE fabrication process 900, step-scan spectroscopy using a monochromator-based spectrometer. The loop 935" encompasses either of the sequences {930, 940} or {935, 945}.

In some implementations, the loop 935" (corresponding to the sequence {930, 940}) can be performed as a sequence of operations {931", 933", 942"}. Examples of such implementations are described above in connection with FIGS. 5B, 3C, 3D and 3E.

As part of the $j^{th}$ iteration of the loop 935", where j=1 to $m_{max} \geq 2$, at 931", probe-light having a wavelength range (e.g., the measurement spectral range [$\lambda_{min}, \lambda_{max}$]) is received by the spectrometer's monochromator. Additionally, a $j^{th}$ instance of the probe-light corresponding to a relative orientation $\Delta\theta(j)$ between a diffractive element and an exit slit is provided by the monochromator. The provided $j^{th}$ instance of the probe-light is quasi-monochromatic, because it includes wavelengths centered on a particular wavelength of the measurement spectral range [$\lambda_{min}, \lambda_{max}$] corresponding to a relative angular orientation $\Delta\theta(j)$ between the diffractive element and the exit slit, and a narrow wavelength range, $\Delta\lambda << |\lambda_{max} - \lambda_{min}|$. In the examples illustrated in FIG. 5B, the probe-light output by the source OS over the measurement spectral range [$\lambda_{min}, \lambda_{max}$] is denoted 370, and the $j^{th}$ instance of the probe-light provided by the monochromator is denoted 572.

At 933", the $j^{th}$ instance of the probe-light is modulated with an optical chopper prior to illuminating the layers L(1), ..., L(i) of the witness sample formed at 920. In the examples illustrated in FIGS. 5B and 3C, the $j^{th}$ modulated instance of the probe-light is denoted 574.

At 942", the modulated $j^{th}$ instance of the probe-light that interacts with the formed layers L(1), ..., L(i) of the witness sample is detected, over a finite time interval, using lock-in detection. An output V(j) of the lock-in detection is proportional to amplitude of the modulation of the detected modulated $j^{th}$ instance of the probe-light that interacts with the witness sample. In this manner, the output V(j) corresponds to the relative orientation $\Delta\theta(j)$ between the diffractive element and the exit slit. In the examples illustrated in FIGS. 3C-3E, the $j^{th}$ modulated instance of the probe-light that interacts with the witness sample is denoted 576; the detected modulated $j^{th}$ instance of the probe-light that interacts with the witness sample—which includes the modulation 345—is denoted 512; and the output V(j) corresponding to the relative orientation $\Delta\theta(j)$ between a diffractive element and an exit slit is denoted 515.

In other implementations, the loop 935" (corresponding to the sequence {930, 940}) can be performed as a sequence of operations {932", 934", 942"}. Examples of such implementations are described above in connection with FIGS. 6, 3C, 3D and 3E.

At, 932", a modulated probe-light having a wavelength range is provided to the spectrometer's monochromator. In the example illustrated in FIG. 6, the modulated probe-light output by the source OS over the measurement spectral range [$\lambda_{min}, \lambda_{max}$] is denoted 371.

As part of the $j^{th}$ iteration of the loop 935", where j=1 to $m_{max} \geq 2$, at 934", the modulated probe-light is received by the monochromator. Additionally, a $j^{th}$ instance of the modulated probe-light corresponding to a relative orientation $\Delta\theta(j)$ between a diffractive element and an exit slit is provided by the monochromator. As described above, the provided $j^{th}$ instance of the modulated probe-light is quasi-monochromatic, because it includes wavelengths centered on a particular wavelength of the measurement spectral range [$\lambda_{min}, \lambda_{max}$] corresponding to the current relative angular orientation $\Delta\theta(j)$ between the diffractive element and the exit slit, and a narrow wavelength range, $\Delta\lambda << |\lambda_{max} - \lambda_{min}|$. In the example illustrated in FIG. 6, the $j^{th}$ instance of the modulated probe-light provided by the monochromator is denoted 574.

At 942", the $j^{th}$ instance of the modulated probe-light that interacts with the formed layers L(1), ..., L(i) of the witness sample is detected, over a finite time interval, using lock-in detection. An output V(j) of the lock-in detection is proportional to amplitude of the modulation of the detected $j^{th}$ instance of the modulated probe-light that interacts with the witness sample. In this manner, the output V(j) corresponds to the relative orientation Δθ(j) between the diffractive element and the exit slit. In the examples illustrated in FIGS. 3C-3E, the $j^{th}$ instance of the modulated probe-light that interacts with the witness sample is denoted 576; the detected $j^{th}$ instance of the modulated probe-light that interacts with the witness sample—which includes the modulation 345—is denoted 512; and the output V(j) corresponding to the relative orientation Δθ(j) between a diffractive element and an exit slit is denoted 515.

In some other implementations, the loop 935" (corresponding to the sequence {935, 945}) can be performed as a sequence of operations {931", 937", 947"}. Examples of such implementations are described above in connection with FIGS. 8B, 7C, 7D and 7E.

As part of the $j^{th}$ iteration of the loop 935", where j=1 to $m_{max}$≥2, at 931", probe-light having a wavelength range (e.g., the measurement spectral range [$\lambda_{min},\lambda_{max}$]) is received by the spectrometer's monochromator. Additionally, a $j^{th}$ instance of the probe-light corresponding to a relative orientation Δθ(j) between a diffractive element and an exit slit is provided by the monochromator. The provided $j^{th}$ instance of the probe-light is quasi-monochromatic, because it includes wavelengths centered on a particular wavelength of the measurement spectral range [$\lambda_{min},\lambda_{max}$] corresponding to the relative angular orientation Δθ(j) between the diffractive element and the exit slit, and a narrow wavelength range, $\Delta\lambda<<|\lambda_{max}-\lambda_{min}|$. In the examples illustrated in FIG. 8B, the probe-light output by the source OS over the measurement spectral range [$\lambda_{min}, \lambda_{max}$] is denoted 370, and the $j^{th}$ instance of the probe-light provided by the monochromator is denoted 572.

At 937", a witness sample including the formed layers is illuminated with the $j^{th}$ instance of probe-light corresponding to the relative orientation Δθ(j) between a diffractive element and an exit slit using the timing of the periodic motion of the witness sample. In this manner, a modulation is imparted to the $j^{th}$ instance of the probe-light by alternately transmitting the $j^{th}$ instance of the probe-light through the witness sample and passing the same by the witness sample. Attenuation of the $j^{th}$ instance of the probe-light is proportional to a value of amplitude of the modulation of the $j^{th}$ instance of probe-light generated as described above. In the examples illustrated in FIGS. 8B and 7C, the modulated probe-light is denoted 876 and a timing of its modulation is denoted 765.

At 947", the $j^{th}$ instance of probe-light that interacts with the periodically moving formed layers is detected, over finite time interval, using time-gated detection. An output V(j) of the time-gated detection is proportional to amplitude of a modulation of the detected $j^{th}$ instance of the probe-light that interacts with the witness sample. In this manner, an output V(j) of the time-gated detection corresponds to the relative orientation Δθ(j) between the diffractive element and the exit slit. In the examples illustrated in FIGS. 7C-7E, the $j^{th}$ instance of the probe-light that interacts with the witness sample is denoted 876; the detected $j^{th}$ instance of the probe-light that interacts with the witness sample—which includes the modulation with timing 765—is denoted 812; and the output V(j) corresponding to the relative orientation Δθ(j) between the diffractive element and the exit slit is denoted 815.

In general, subsequent iterations of the loop 935" will generate outputs V(j+1), . . . , V($m_{max}$) of the lock-in or time-gated detection corresponding to subsequent relative orientations Δθ(j+1), . . . , Δθ($m_{max}$). As the set of values {V(j), j=1−$m_{max}$} are being acquired, or when their acquisition is completed, the acquired values {V(j), j=1−$m_{max}$} can be represented in plot 524 illustrated in FIG. 5C. Once the entire set of values {V(1), . . . , V($m_{max}$)} corresponding to all available optical path differences Δθ(1), . . . , Δθ($m_{max}$) is recorded, the operations of 950 of the process 900 can be performed.

At 956, a set of the detection outputs {V(1), . . . , V($m_{max}$)} corresponding to the relative orientations Δθ(1), . . . , Δθ($m_{max}$) is fitted to obtain a relative orientation dependence of the detected probe-light that interacts with the formed layers of the ICE. In the example illustrated in FIG. 5C, the obtained relative orientation dependence of the detected probe-light that interacts with the formed layers is denoted V(θ), where "θ" is the relative orientation between the diffractive element and the exit slit.

At 958, the obtained relative orientation dependence of the detected probe-light that interacts with the formed layers of the witness sample is processed to generate the spectrum of the probe-light that interacted with the formed layers. The processing of the obtained relative orientation dependence of the detected probe-light that interacts with the witness sample includes correlating relative orientations of a range [Δθ(1), Δθ(M)] with wavelengths of the measurement spectral range [$\lambda_{min},\lambda_{max}$] in conjunction with appropriately scaling/normalizing the relative orientation dependence of the detected probe-light that interacts with the witness sample. A result of the processing performed at 958 on the obtained grating angle dependence of the detected probe-light that interacts with the witness sample is represented in the plot 526 (illustrated in FIG. 5D) as a spectrum S(λ;i) of the formed layers L(1), . . . , L(i) of the witness sample over the measurement spectral range [$\lambda_{min},\lambda_{max}$].

The spectrum generated at 958—as a result of performing the step-scan spectroscopy that uses a monochromator-based spectrometer—or at 954—as a result of performing the step-scan spectroscopy that uses an interferometer-based spectrometer—is provided to the process 900 as input to one or more operations to be carried out at 960.

Referring again to FIG. 9A, at 960, the layers L(1), L(2), . . . , L(i−1) formed during previous and current iterations of the loop 915 are characterized based on the spectrum of the interacted probe-light generated at 950. Such characterization of the witness sample's layers is performed in near real-time. For instance, the spectrum of the interacted probe-light (generated at 950) is used to determine complex refractive indices $n*_H$ and $n*_L$ and thicknesses t'(1), t'(2), . . . , t'(i−1), t'(i) of the layers L(1), L(2), . . . , L(i−1), L(i) formed in previous and current iterations of the loop 915.

At 970, deposition of current layer L(i) and of subsequent layers L(i+1), L(i+2), . . . of the ICE(s) being fabricated along with the witness sample is adjusted, if necessary, based on determined complex refractive indices $n*_H$, $n*_L$ and thicknesses t'(1), t'(2), . . . , t'(i−1), t'(i) of formed layers L(1), L(2), . . . , L(i−1), L(i). For example, a deposition rate used to form the layer L(i) currently being formed and other layers L(i+1), L(i+2), . . . remaining to be formed can be adjusted in real-time based on a comparison between values of the complex refractive indices and thicknesses of the layers of the current instance of the ICEs and their respective target values. Alternatively or additionally, complex refractive indices corresponding to the layer L(i) being current formed and other layers L(i+1), L(i+2), . . . remaining to be formed can be adjusted in real-time based on a comparison between values of the complex refractive indices and thicknesses of the layers of the current instance of the ICEs and their respective target values.

Further, in order to determine whether target thicknesses of the layers L(i+1), L(i+2), ..., L(N) remaining to be formed should be updated, the following verification is performed when deposition of the current layer L(i) is completed. An SEC(i) of the ICE is predicted to represent the ICE's performance if the ICE were completed to have the formed layers L(1), L(2), ..., L(i) with the determined thicknesses t'(1), t'(2), ..., t'(i), and layers L(i+1), L(i+2), ..., L(N) remaining to be formed with target thicknesses t(i), t(i), ..., t(N). Here, the predicted SEC(i) of the ICE is caused by deviations of the determined complex refractive indices and thicknesses of the formed layers from their respective target complex refractive indices and thicknesses specified by the current ICE design. If the predicted SEC(i) does not exceed a maximum allowed $SEC_{max}$, SEC(i)$\leq SEC_{max}$, then a next iteration of the loop 915 will be triggered to form the next layer L(i+1) to its target thickness t(i+1).

If, however, the predicted SEC(i;N) exceeds the maximum allowed $SEC_{max}$, SEC(i;N)>$SEC_{max}$, then target thicknesses of the layers L(i+1), L(i+2), ..., L(N) remaining to be formed are modified based on the determined complex refractive indices and thicknesses of the formed layers L(1), L(2), ..., L(i). This optimization may change the total number of layers of the ICE from the specified total number N of layers to a new total number N' of layers, but constrains the thicknesses of the layers L(1), L(2), ..., L(i) (of the current instance of the ICE) to the determined thicknesses t'(1), t'(2), ..., t'(i). In this manner, the optimization obtains, in analogy with the process 200 described above in connection with FIG. 2, new target thicknesses t"(i+1), ..., t"(N') of the layers L(i+1), ..., L(N') remaining to be formed, such that a new target SEC'$_t$(i;N') of the ICE—for the ICE having the first layers L(1), L(2), ..., L(i) formed with the determined thicknesses t'(1), t'(2), ..., t'(i), and the layers L(i+1), ..., L(N') remaining to be formed with the new target thicknesses t"(i+1), ..., t"(N')—is minimum and does not exceed the maximum allowed $SEC_{max}$, SEC'$_t$(i;N')$\leq SEC_{max}$.

Once the previous instance of the ICE design is updated with specification of the new total number of layers N' and the new target thicknesses t"(i+1), ..., t"(N')—which are used to form the remaining layers L(i+1), ..., L(N') and correspond to the new target SEC'$_t$(i;N')—a next iteration of the loop 915 will be triggered to form the next layer L(i+1) from the new total number of layers N' to its new target thickness t"(i+1). In this manner, the remaining layers of the ICE will be formed based on the updated ICE design, at least until another update is performed.

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. A method comprising:
   receiving, by a fabrication system, a design of an integrated computational element (ICE), the ICE design comprising specification of a substrate and a plurality of layers, their respective target thicknesses and complex refractive indices, wherein complex refractive indices of adjacent layers are different from each other, and wherein a notional ICE fabricated in accordance with the ICE design is related to a characteristic of a sample;
   forming, by the fabrication system, at least some of the layers of a plurality of ICEs in accordance with the ICE design;
   sequentially illuminating, by a measurement system associated with the fabrication system, the formed layers with instances of probe-light provided by the measurement system, the instances being spectrally different from each other within a measurement spectral range, such that each of the instances of the probe-light illuminates the formed layers for a finite time interval;
   detecting, by the measurement system for each of the instances of the probe-light, a modulation of probe-light that interacts with the formed layers;
   generating, by the measurement system, a spectrum of the probe-light interacted with the formed layers over the measurement spectral range from a set of values of the detected modulations corresponding to the instances of the probe-light; and
   adjusting, by the fabrication system, said forming based on the generated spectrum.

2. The method of claim 1, further comprising generating the modulation of the instances of probe-light that interacted with the formed layers prior to said illuminating the formed layers.

3. The method of claim 2, wherein the instances of the probe-light are modulated with an optical chopper.

4. The method of claim 3, wherein the optical chopper is placed within an optical path starting at an optical source that emits the probe-light and ending at the formed layers.

5. The method of claim 3, wherein the optical chopper comprises one of a shutter or an acousto-optic modulator.

6. The method of claim 2, further comprising emitting, by an optical source that spans the measurement spectral range, the probe-light as a train of pulses, wherein the instances of the probe-light are modulated by the train of pulses.

7. The method of claim 2, wherein the formed layers are at rest, while performing said detection is performed, relative to a location where the modulated instances of the probe-light illuminate the formed layers.

8. The method of claim 2, further comprising:
receiving, by an interferometer of the measurement system, probe-light provided by an optical source that spans the measurement spectral range; and
for each optical path difference of a plurality of optical path differences of the interferometer, providing, by the interferometer, an instance of the probe-light associated with the optical path difference.

9. The method of claim 8, wherein each of the optical path differences is maintained at least for a duration of the finite time interval.

10. The method of claim 8, wherein the measurement system associated with the fabrication system comprises an FTIR spectrometer.

11. The method of claim 8, wherein said detecting is synchronized with the modulation and is performed using a lock-in detector referenced by the modulation.

12. The method of claim 11, wherein the finite time interval during which each of the modulated instances is detected comprises a specified number of time constants of the lock-in detector.

13. The method of claim 12, wherein the specified number of time constants of the lock-in detector is between five and ten.

14. The method of claim 11, further comprising for each optical path difference of a plurality of optical path differences of the interferometer, detecting, by the lock-in detector, the modulation of the instance of the probe-light that interacted with the formed layers as a lock-in detector signal corresponding to the optical path difference.

15. The method of claim 14, wherein said generating the spectrum of the probe-light that interacted with the formed layers over the measurement spectral range comprises
fitting a set of values of lock-in detector signals corresponding to the plurality of optical path differences to obtain an optical path difference dependence of the detected modulation, and
processing the obtained optical path difference dependence of the detected probe-light to generate the spectrum.

16. The method of claim 15, wherein said processing the obtained optical path difference dependence of the detected probe-light comprises Fourier transforming the obtained optical path difference dependence of the detected probe-light.

17. The method of claim 2, further comprising:
receiving, by a monochromator of the measurement system, probe-light provided by an optical source that spans the measurement spectral range, wherein the monochromator includes a wavelength selector and an output port; and
for each relative orientation of a plurality of relative orientations between the wavelength selector and the output port of the monochromator, providing, by the monochromator, an instance of the probe-light associated with the relative orientation.

18. The method of claim 17, wherein each of the relative orientations between the wavelength selector and the output port of the monochromator is maintained at least for a duration of the finite time interval.

19. The method of claim 17, wherein
said detecting is synchronized with the modulation and is performed using a lock-in detector referenced by the modulation, and
the method further comprises for each relative orientation of a plurality of relative orientations between the wavelength selector and the output port of the monochromator detecting, by the lock-in detector, the modulation of the instance of the probe-light that interacted with the formed layers as a lock-in detector signal corresponding to the relative orientation.

20. The method of claim 19, wherein said generating the spectrum of the probe-light that interacted with the formed layers over the measurement spectral range comprises
fitting a set of values of the lock-in detector signals corresponding to the plurality of relative orientations between the wavelength selector and the output port of the monochromator to obtain a wavelength selector orientation dependence of the detected probe-light, and
processing the obtained wavelength selector orientation dependence of the detected probe-light to generate the spectrum.

21. The method of claim 20, wherein said processing comprises correlating the plurality of relative orientations between the wavelength selector and the output port of the monochromator with corresponding wavelengths of the measurement spectral range.

22. The method of claim 1, further comprising generating the modulation of the instances of probe-light that interacted with the formed layers by periodically moving the formed layers in-and-out of a beam spot of the instances of probe-light, such that the modulation corresponds to timing of the periodic motion.

23. The method of claim 22, further comprising:
receiving, by an interferometer of the measurement system, probe-light provided by an optical source that spans the measurement spectral range; and
for each optical path difference of a plurality of optical path differences of the interferometer, providing, by the interferometer, an instance of the probe-light associated with the optical path difference.

24. The method of claim 23, wherein each of the optical path differences is maintained at least for a duration of the finite time interval.

25. The method of claim 23, wherein the measurement system associated with the fabrication system comprises an FTIR spectrometer.

26. The method of claim 23, wherein said detecting is performed using a time-gated detector timed by the modulation.

27. The method of claim 26, wherein
a support has one or more apertures, wherein the ICEs are supported on the support such that at least two of the ICEs have an aperture between them, and
for each optical path difference of a plurality of optical path differences of the interferometer, said detecting the modulation of the instance of the probe-light that interacted with the formed layers comprises
moving the support such that the instance of the probe-light illuminates a current instance of the formed layers,
collecting, by the time-gated detector, the instance of the probe-light transmitted through the current instance of the formed layers illuminated with the instance of the probe-light,
recording a first detector signal from the collected instance of probe-light transmitted through the current instance of the formed layers when the instance of the probe-light illuminates the current instance of the formed layers,
moving the support such that the instance of the probe-light illuminates an aperture of the support, collecting, with the time-gated detector, the instance of probe-light that passes through the aperture without being transmitted through the current instance of the formed layers, recording a reference detector signal when the instance of the probe-light illuminates the aperture, and obtaining, by the time-gated detector, a referenced time-gated detector signal corresponding to the optical path difference based on the first detector signal and the reference detector signal.

28. The method of claim 27, wherein said generating the spectrum of the probe-light that interacted with the formed layers over the measurement spectral range comprises fitting a set of values of referenced time-gated detector signals corresponding to the plurality of optical path differences to obtain an optical path difference dependence of the detected modulation, and processing the obtained optical path difference dependence of the detected probe-light to generate the spectrum.

29. The method of claim 28, wherein said processing the obtained optical path difference dependence of the detected probe-light comprises Fourier transforming the obtained optical path difference dependence of the detected probe-light.

30. The method of claim 22, further comprising:

receiving, by a monochromator of the measurement system, probe-light provided by an optical source that spans the measurement spectral range, wherein the monochromator includes a wavelength selector and an output port; and for each relative orientation of a plurality of relative orientations between the wavelength selector and the output port of the monochromator, providing, by the monochromator, an instance of the probe-light associated with the relative orientation.

31. The method of claim 30, wherein each of the relative orientations between the wavelength selector and the output port of the monochromator is maintained at least for a duration of the finite time interval.

32. The method of claim 30, wherein said detecting is performed using a time-gated detector timed by the modulation, a support has one or more apertures, wherein the ICEs are supported on the support such that at least two of the ICEs have an aperture between them, and for each relative orientation of a plurality of relative orientations between the wavelength selector and the output port of the monochromator, said detecting the modulation of the instance of the probe-light that interacted with the formed layers comprises moving the support such that the instance of the probe-light illuminates a current instance of the formed layers, collecting, by the time-gated detector, the instance of the probe-light transmitted through the current instance of the formed layers illuminated with the instance of the probe-light, recording a first detector signal from the collected instance of probe-light transmitted through the current instance of the formed layers when the instance of the probe-light illuminates the current instance of the formed layers, moving the support such that the instance of the probe-light illuminates an aperture of the support, collecting, with the time-gated detector, the instance of probe-light that passes through the aperture without being transmitted through the current instance of the formed layers, recording a reference detector signal when the instance of the probe-light illuminates the aperture, and obtaining, by the time-gated detector, a referenced time-gated detector signal corresponding to the relative orientation between the wavelength selector and the output port of the monochromator based on the first detector signal and the reference detector signal.

33. The method of claim 32, wherein said obtaining the spectrum of the probe-light that interacted with the formed layers over the measurement spectral range comprises fitting a set of values of the referenced time-gated detector signals corresponding to the plurality of relative orientations between the wavelength selector and the output port of the monochromator to obtain a wavelength selector orientation dependence of the detected probe-light, and processing the obtained wavelength selector orientation dependence of the detected probe-light to generate the spectrum.

34. The method of claim 33, wherein said processing comprises correlating the plurality of relative orientations between the wavelength selector and the output port of the monochromator with corresponding wavelengths of the measurement spectral range.

35. The method of claim 1, wherein the modulation has a frequency that is specified to be different from frequencies or tones of sources emitting stray light that can be detected by the measurement system, where wavelengths of the stray light are within the measurement spectral range.

36. The method of claim 1, wherein the probe-light interacted with the formed layers comprises one of transmitted light, scattered light, or emitted light.

37. The method of claim 1, wherein said adjusting comprises characterizing the formed layers based on the generated spectrum.

38. The method of claim 37, further comprising updating a deposition rate used to form layers remaining to be formed based on results of said characterizing the formed layers.

39. The method of claim 37, further comprising modifying refractive indices of the layers remaining to be formed based on results of said characterizing the formed layers.

40. The method of claim 37, further comprising modifying target thicknesses of the layers remaining to be formed based on results of said characterizing the formed layers.

41. The method of claim 37, wherein said adjusting comprises changing a total number of layers specified by the ICE design to a new total number of layers.

42. A system comprising:

a deposition chamber;

one or more deposition sources associated with the deposition chamber to provide materials from which layers of one or more integrated computational elements (ICEs) are formed;

a spectrometer associated with the deposition chamber to measure in-situ one or more spectra of the layers of the ICEs, wherein the spectra are measured using timing of a modulation of instances of probe-light that sequentially interacted with the ICE layers, the instances being spectrally different from each other within a measurement spectral range; and one or more supports disposed inside the deposition chamber, at least partially, within a field of view of the deposition source(s) and another field of view of the spectrometer to support the ICE layers while they are formed and their spectra are measured, respectively;

a computer system in communication with at least some of the one or more deposition sources, the support(s) and the spectrometer, wherein the computer system comprises one or more hardware processors and non-transitory computer-readable medium encoding instructions that, when executed by the one or more hardware processors, cause the system to form the layers of the ICEs by performing operations comprising:

receiving an ICE design comprising specification of a substrate and a plurality of layers, their respective target thicknesses and complex refractive indices, wherein complex refractive indices of adjacent layers are different from each other, and wherein a notional ICE fabricated in accordance with the ICE design is related to a characteristic of a sample;

forming at least some of the layers of a plurality of ICEs in accordance with the ICE design;

measuring, by the spectrometer during said forming, spectra of the layers of the ICEs; and adjusting said forming based on the measured spectra.

43. The system of claim 42, wherein the spectrometer further comprises an interferometer arranged to receive probe-light from a light source, the interferometer further to provide the instances of probe-light that illuminate the ICEs, each of the instances of probe-light corresponding to an associated optical path difference of the interferometer.

44. The system of claim 42, wherein
the spectrometer further comprises a monochromator that includes a wavelength selector and an output port, and the monochromator to receive probe-light from a light source and to provide the instances of probe-light that illuminate the ICEs, each of the instances of probe-light corresponding to an associated relative orientation between the wavelength selector and the output port of the monochromator.

45. The system of claim 42, wherein the spectrometer further comprises a lock-in detection module to detect the modulation of the instances of probe-light that interacted with the ICE layers, such that the lock-in detection module is referenced by the modulation.

46. The system of claim 45, wherein the spectrometer further comprises an optical chopper—placed in a path of the instances of probe-light that illuminate the ICEs—to provide the modulation to the instances of probe-light that illuminate the ICEs.

47. The system of claim 45, wherein
the spectrometer further comprises an optical source to emit probe-light that is pulse-modulated with the modulation, and
the pulse-modulated probe-light is used to provide modulated instances of probe-light that illuminate the ICEs, such that the provided modulation is used as a reference signal for the lock-in detection module.

48. The system of claim 42, wherein the spectrometer further comprises a time-gated detection module to detect the modulation of the instances of probe-light that interact with the ICE layers, such that the time-gated detection module is timed by the modulation.

49. The system of claim 48, wherein
the support(s) has(ve) one or more apertures, wherein the ICEs are supported on the supports such that at least two of the ICEs have an aperture between them,
the modulation is generated by alternately transmitting the instances of probe-light through the ICE layers and through the aperture(s).

* * * * *

UNITED STATES PATENT AND TRADEMARK OFFICE
CERTIFICATE OF CORRECTION

PATENT NO. : 9,727,052 B2  
APPLICATION NO. : 14/414653  
DATED : August 8, 2017  
INVENTOR(S) : James M. Price, Aditya B. Nayak and David L. Perkins Page 1 of 1

It is certified that error appears in the above-identified patent and that said Letters Patent is hereby corrected as shown below:

In the Claims

In Claim 41, Column 56, Line 49, after "claim" delete "37" and insert --40--

Signed and Sealed this  
Sixteenth Day of January, 2018

Joseph Matal  
*Performing the Functions and Duties of the*  
*Under Secretary of Commerce for Intellectual Property and*  
*Director of the United States Patent and Trademark Office*